US008084424B2

(12) United States Patent
Kishore et al.

(10) Patent No.: US 8,084,424 B2
(45) Date of Patent: Dec. 27, 2011

(54) COMPOSITIONS AND METHODS RELATED TO ERYTHROPOIETIN

(75) Inventors: Bellamkonda Kishore, Sandy, UT (US); Christof Westenfelder, Salt Lake City, UT (US); Jorge Issac, Murray, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1374 days.

(21) Appl. No.: 10/552,568

(22) PCT Filed: Apr. 9, 2004

(86) PCT No.: PCT/US2004/011003
§ 371 (c)(1),
(2), (4) Date: Aug. 2, 2006

(87) PCT Pub. No.: WO2004/091495
PCT Pub. Date: Oct. 28, 2004

(65) Prior Publication Data
US 2007/0078084 A1    Apr. 5, 2007

Related U.S. Application Data

(60) Provisional application No. 60/461,941, filed on Apr. 9, 2003.

(51) Int. Cl.
*A61K 38/18* (2006.01)
(52) U.S. Cl. .......... 514/7.7; 514/1.1; 514/7.6; 514/15.4; 514/15.5
(58) Field of Classification Search ............... 514/7.7, 514/7.6, 15.5, 1.1, 15.4
See application file for complete search history.

(56) References Cited

U.S. PATENT DOCUMENTS

| | | | |
|---|---|---|---|
| 4,526,888 A | 7/1985 | Williams et al. | |
| 4,667,016 A | 5/1987 | Lai et al. | |
| 4,703,008 A | 10/1987 | Lin | |
| 4,935,350 A | 6/1990 | Patel et al. | |
| 4,987,121 A | 1/1991 | Baertschi et al. | |
| 5,032,507 A | 7/1991 | Yu et al. | |
| 5,104,653 A | 4/1992 | Michalevicz | |
| 5,106,760 A | 4/1992 | Egrie | |
| 5,354,934 A | 10/1994 | Pitt et al. | |
| 5,476,653 A | 12/1995 | Pitt et al. | |
| 5,482,924 A | 1/1996 | Royet et al. | |
| 5,547,933 A | 8/1996 | Lin | |
| 5,597,562 A | 1/1997 | Nomura et al. | |
| 5,618,698 A | 4/1997 | Lin | |
| 5,621,080 A | 4/1997 | Lin | |
| 5,661,125 A | 8/1997 | Strickland | |
| 5,756,349 A | 5/1998 | Lin | |
| 5,830,705 A | 11/1998 | Souza | |
| 5,885,574 A | 3/1999 | Elliott | |
| 5,919,464 A * | 7/1999 | Mann et al. | 424/278.1 |
| 5,955,422 A | 9/1999 | Lin | |
| 6,080,557 A * | 6/2000 | Sims et al. | 435/69.1 |
| 6,221,397 B1 | 4/2001 | Russell-Jones et al. | |
| 6,319,499 B1 | 11/2001 | Elliott | |
| 6,784,154 B2 | 8/2004 | Westenfelder | |
| 2001/0038859 A1 * | 11/2001 | Maskiewicz et al. | 424/499 |
| 2003/0108556 A1 * | 6/2003 | Mekalanos et al. | 424/184.1 |
| 2003/0109452 A1 * | 6/2003 | Owen | 514/13 |
| 2003/0219407 A1 * | 11/2003 | Ding et al. | 424/93.2 |

FOREIGN PATENT DOCUMENTS

| | | |
|---|---|---|
| FR | 2321898 | 3/1977 |
| WO | WO 0027997 | 5/2000 |
| WO | WO 01/66149 A2 | 9/2001 |

OTHER PUBLICATIONS

Sigma Catalog (1998) p. 2105.*
Kurtz A, Jelkmann W, Pfeilschifter J, Bauer C. (1986) Erythropoietin Production in Cultures of Rat Renal Mesangial Cells. *Contr. Nephrol.*, 50: 175-87.
Kurtz A, Jelkmann W, Pfuhl A, Malmstrom K, Bauer C. (1986) Erythropoietin Production by Fetal Mouse Liver Cells in Response to Hypoxia and Adenylate Cyclase Stimulation. *Endocrinology*, 118 (2): 567-72.
Masuda S, Chikuma M, Sasaki R. (1997) Insulin-Like Growth Factors and Insulin Stimulate Erythropoietin Production in Primary Cultured Astrocytes. *Brain Res.*, 746(1-2): 63-70.
Wang MD, Yang M, Huzel N, Butler M. (2002) Erythropoietin Production from CHO Cells Grown by Continuous Culture in a Fluidized-bed Bioreactor. *Biotechnology Bioeng.*, 77(2): 194-203.
Abbate, M., et al., "Proteinuria as a mediator of tubulointerstitial injury," Kidney Blood Press Res 22:37-46, 1999.
Anagnostou, A., et al., "Factors which affect erythropoiesis in partially nephrectomized and sham-operated rats," Blood 48:425-433, 1976. Bachmann, S., et al., "Co-localization of erythropoietin messenger RNA and ecto-5'-nucleotidase immunoreactivity in peritubular cells of rat renal cortex indicates that fibroblasts produce erythropoietin," J. Histochem Chytochem 41:335-341, 1993.
Bellizzi, V., et al., The impact of early normalization of haematocrit by erythropoietin on renal damage in the remnant kidney model, Nephrol Dial. Transplant 13:2210-2215, 1998.
Browne, et al., "Erythropoietin: Gene cloning, protein structure, and biological properties," Cold Spring Harbor Symposia on Quantitative Biology, L1:693-702, 1986.
Burton, C., et al., "The role of proteinuria in the progression of chronic renal failure," Am. J. Kidney Dis. 27:765-775, 1996.
Carlini, R., et al., "Recombinant human erythropoietin stimulates angiogenesis in vitro," Kidney, Int. 47:740-745, 1995.

(Continued)

*Primary Examiner* — Susan Hanley
(74) *Attorney, Agent, or Firm* — Ballard Spahr LLP

(57) ABSTRACT

Disclosed are methods and compositions related to the production of erythropoietin. The disclosed compositions comprise a poly amino acid. The production of erythropoietin by the disclosed compositions and methods can take place in vivo, in which the proliferation of a subject's erythropoietin-producing cells leads to an increased level of production of erythropoietin, in vitro, in which increased proliferation of cultured erythropoietin-producing cells leads to an increased production of erythropoietin, ex vivo, in which cells or tissues harvested from a subject produce erythropoietin. The disclosed compositions can be administered to a subject or applied to cells or tissues to stimulate increased production of erythropoietin. The disclosed compositions and methods can be used, for example, to treat anemia, such as anemia associated with diseases and disorders such as chronic renal failure, end stage renal disease, malignancies, HIV infections and AIDS, rheumatoid arthritis, myeloma, and myeloplastic syndrome, and other diseases and disorders.

25 Claims, 31 Drawing Sheets

OTHER PUBLICATIONS

Dendorfer, U., "Molecular biology of cytokines, Art. Organs," 20:437-444, 1996.

Donnelly, S., "Why is erythropoietin made in the kidney? The kidney functions as a critmeter," Am J. Kidney Dis. 38:415-425, 2001.

Eddy, A.A., "Interstitial nephritis induced by protein overlaod proteinuria," Am. J. Pathol. 135:719-733, 1989.

Eddy, A.A., "Molecular basis of renal fibrosis," Pediatr. Nephrol. 15:290-301, 2000.

Eddy, A.A., "Role of cellular infiltrates in response to proteinuria," Am. J. Kidney Dis., 37:S25-S29, 2001.

Ferrara, N., Molecuar and biological properties of vascular endothelial growth factor, J. Mole. Med. 77:527-543, 1999.

Gandi, R., et al., "Immunolocalization of ecto-5'-nucleotidase in the kidney by a monoclonal antibody," Histochemistry 95:165-174, 1990.

Ghielli, M., et al., "Inflammatory cells in renal pathology," Néphrologie 19:59-67, 1998.

Gleadle, J.M. et al., "Induction of hypoxia-inducible factor-1 erythropoietin, vascular endothelial growth factor and glucose transporter-1 by hypoxia: evidence against a regulatory role for Src kinase," Blood 89:503-509, 1997.

Ivan, M., et al., "HIF alpha targeted for VHL-mediated destruction by praline hydroxylation: implications for $O_2$ sensing," Science 292:464-468, 2001.

Jaakkola, P., et al., "Targeting of HIF alpha to the von Hippel-Lindau urbiquitylation complex by $O_2$ regulated prolyl hydroxylation," Science 292:468-472, 2001.

Jelkmann, W., "Erythropoietin: structure, control of production, and function," Physio. Rev. 72:449-489, 1992.

Johnson, D.W., "Human renal fibroblasts modulate proximal tubule cell growth and transport via the IGF-1 axis," Kidney Int. 52:1486-1496, 1997.

Kaissling, B., Morphology of interstitial cells in the healthy kidney, Anat. Embryol. 193:303-318, 1996.

Keane, W.F., Proteinuria: its clinical importance and role in progressive renal disease, AM. J. Kidney Dis. 35:S97-S105, 2000.

Kendall, R.G., "Erythropoietin," Clin. Lab. Hematol. 23:71-80, 2001.

Kishore, B.K., "Mechanism of the thesaurismosis and altered lysosomal dynamics induced by poly-D-glutamic acid in kidney proximal tubular cells," Lab. Invest. 74:1025-1037, 1996.

Kishore, B.K., et al., "Expression of renal aquaporins 1, 2, and 3 in a rat model of cisplatin-induced polyuria," Kidney Int. 58:701-711, 2000.

Kishore, B.K., et al., "Mechanism of protection afforded by polyaspartic acid against gentamicin-induced phospholipidosis II. Comparative in vitro and in vivo studies with poly-L-aspartic, poly-L-glutamic and poly-D-glutamic acids," J. Pharmacol. Exp. Ther. 255:875-885, 1990.

Kishore, B.K., et al., "Poly-D-glutamic acid induces an acute lysosomal thesaurismosis of proximal tubules and a marked proliferation of interstitium in rat kidney," Lab. Invest. 74:1013-1023, 1996.

Koury, S., et al., "Localization of erythropoietin synthesizing cells in murine kidneys by in situ hybridization," Blood 71:524-527, 1988.

Koury, S., et al., "Quantitation of erythropoietin-producing cells in kidneys of mice by in situ hybridization. Correlation with hamtocrit, renal erythropoietin mRNA and serum erythropoietin concentration," Blood 74:645-651, 1989.

Krantz, S., "Erythropoietin," Blood 77:419-434, 1991.

Lacombe, C., et al., The molecular biology of erythropoietin, Nephrol. Dial. Transplant 14:22-28, 1999.

Lando, D.F., et al., "Aspargine hydroxylation of HIF alpha transactivation domain: a hypoxic switch," Science 295:858-861, 2002.

Le Hir, et al., "Distribution of 5'-nuclleotides in the renal interstitium of the rat," Cell Tissue Res. 258:177-182, 1989.

Maxwell, et al., The interstitial response to renal injury: fibroblast-like cells show phenotypic changes and have reduced potential for erythropoietin gene expression, Kidney Int., 52:715-724, 1997.

Maxwell, et al., "Identification of the renal erythropoietin producing cells using transgenic mice," Kidney Int. 44:1149-1162, 1993.

Priyadarshi, A., et al., "Effects of reduction of renal mass on renal oxygen tension and erythropoietin production in the rate," Kidney Int. 61:542-546, 2002.

Ribatti, D., "Human erythropoietin induces a pro-angiogenic phenotype in cultered endothelial cells and stimulates neovascularization in vivo," Blood 93:2627-2636, 1999.

Schena, F.P, Cytokine network and resident renal cells in glomerular diseases. Nephol. Dial. Transplant 14 [Suppl 1]:22-26, 1992.

Schuster, S., et al., "Cellular sites of extra renal and renal erythropoietin production in anaemic rats," Brit. J. Hemat. 81:153-159, 1992.

Shih, S.C., et al., "Hypoxia-mediated regulation of gene expression in mammalian cells," Int. J. Exp. Pathol. 79:347-357, 1998.

Todd, et al. Poly-L-Aspartic Acid Protects Cultured Human Proximal Tubule Cells Against Aminoglycoside-Induced Electrophysiological Alterations, Toxicology Lett. vol. 90, Nos. 2 and 3:217-221, see Figures 1 and 2, 1997.

von Kooten, C., et al., "Role of tubular cells in progressive renal disease," Kidney Blood Press. Res. 22:53-61, 1999.

Westenfelder, C., "Unexpected renal actions of erythropoietin," Exp. Nephrol. 10:294-298, 2002.

Westenfelder, C., et al., "Erythropoietin stimulates proliferation of human renal carcinoma cells," Kidney Int. 58:647-657, 2000.

Westenfelder, C., et al., Erythropoietin treatment ameliorates ischemic acute renal failure in rats by its anti-apoptotic, motogenic and mitogenic actions, J. Am. Soc. Nephrol 12:793A, 2001.

Westenfelder, C.,et al., "Human, rat and mouse kidney cells express functional erythropoietin receptors," Kidney Int. 55:808-820, 1999.

Westenfelder, C., et al., Dual roles of NFkB in ischemic acuture renal fauilure in rats: (1) mediates maladaptive suppression of erythropoietin (EPO) gene, (2) mediate EPO's anti-apoptotic effects in proximal tubular cells. Abstract #T323 accepted for presentation at the World Congress of Nephrology, Berlin, Jun. 8-12, 2003.

Wolf, G., et al., Molecular mechanisms of tubulointerstitial hypertrophy and hyperplasia, Kidney Int. 39:401-420, 1991.

Youssoufian, H., et al., "Structure, function, and activation of the erythropoietin receptor," Blood 81:2223-2236, 1993.

Zoja, C., et al.,"Protein overload activates proximal tubular cells to release vasoactiove and inflammatory mediators," Exp. Nephrol. 7:420-428, 1999.

Parke et al. Multiple organ dysfunction syndrome. Inflammopharmacology, vol. 11, No. 1, pp. 87-95 (2003).

Gabriel et al. High-dose recombinant human EPO stimulates reticulocyte production in patients with multiple organ dysfunction syndrome. J. of Trauma 44(2):361-7 (Feb. 1998).

Office Action (U.S. Appl. No. 11/791,287), Mailed Aug. 18, 2010.

Final Office Action issued on Feb. 23, 2011 for U.S. Appl. No. 11/791,287, filed May 27, 2007 (Inventor—Westenfelder).

* cited by examiner

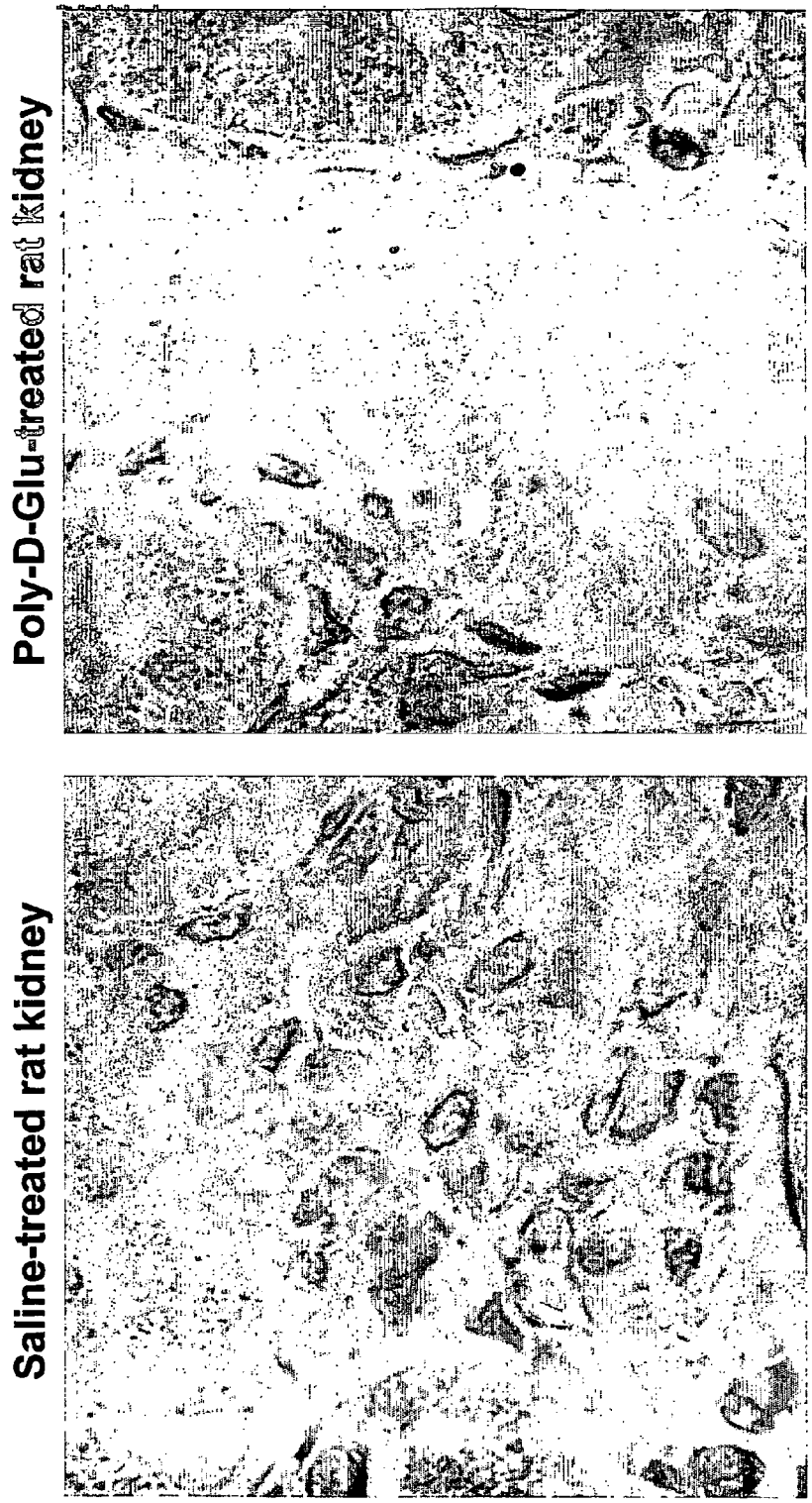

COMPOSITIONS AND METHODS RELATED TO ERYTHROPOIETIN

This application is a national stage entry of PCT/US04/11003, filed Apr. 9, 2004, which claims priority to U.S. provisional application 60/461,941, filed Apr. 9, 2003, which is incorporated herein in its entirety by reference.

STATEMENT REGARDING FEDERALLY SPONSORED RESEARCH

This invention was made possible with funds from Western Institute for Biomedical Research (WIBR), a non-profit organization incorporated in the State of Utah and affiliated with the Veterans Affairs Salt Lake City Health Care System, Salt Lake City, Utah, and with the facilities and resources at the VA Salt Lake City Health Care System. Therefore, the United States Government may have certain rights in this invention.

FIELD

The disclosed compositions and methods generally in the field of erythropoietin production and treatment of disease and conditions involving erythropoietin.

BACKGROUND

Erythropoietin is a natural glycoprotein hormone produced predominantly by the peritubular interstitial cells in the kidney, and transported via the blood to the bone marrow, where it regulates and promotes the maturation of erythroid cells into mature red blood cells. Fibroblast-like cells in the cortical interstitium of the kidney synthesize erythropoietin while tubular cells do not. The former specialized cells express 5'-nucleotidase or CD73 on their surface and are strategically located so as to facilitate erythropoietin secretion into peritubular capillaries, which, in turn, carry erythropoietin past most nephron segments, into the systemic circulation. Significantly, erythropoietin producing cells are in direct contact with the basolateral aspects of proximal tubular and outer medullary cells. This anatomic relationship facilitates bidirectional signaling between tubular and fibroblast-like cells. This is exemplified by paracrine erythropoietin signaling in erythropoietin-receptor-expressing adjacent tubular cells, where signals that originate in proximal tubular cells affect the function of adjacent peritubular fibroblast-like cells.

Decreased production of erythropoietin results in fewer circulating red blood cells or anemia, often associated with end stage renal disease, malignancies, HIV infection and AIDS, rheumatoid arthritis, myeloma and myeloplastic syndrome as well as other diseases and disorders. Currently, the only therapeutic option for erythropoietin-responsive anemia or disorders is the administration of recombinant human erythropoietin (rHuEpo). Disclosed are compositions and methods for the production of erythropoietin.

SUMMARY

Disclosed are methods and compositions related to production of erythropoietin.

BRIEF DESCRIPTION OF THE DRAWINGS

The accompanying drawings, which are incorporated in and constitute a part of this specification, illustrate several embodiments and together with the description illustrate the disclosed compositions and methods.

FIGS. 21A and 21B show that the cells are resident fibroblasts. Having excluded the possibility that the interstitial cells in poly-D-glutamic acid treated rats are not infiltrating blood cells, the possibility that these cells may be resident fibroblasts was examined. CD73 or 5'-nucleotidase is a surface marker protein specific for the resident fibroblasts in kidney. Using a specific antibody to CD73 surface antigen, it was confirmed that the proliferating interstitial cells in the poly-D-glutamic acid treated rats are in deed resident fibroblasts. (See FIG. 21A) The saline treated rat kidneys also show the labeling for resident fibroblasts, which is expected. (See FIG. 21A) Positive labeling is identified as brownish color around the nuclei of the cells. (See FIG. 21A) FIG. 21B shows a negative control for immunohistochemical staining, where primary antibody was omitted from the incubation.

FIG. 22B is a kidney section from a Poly-D-Glu treated rat, immunohistochemically labeled for EPO, using an EPO-specific antibody followed by peroxidase-labeled secondary antibody. All proliferating peritubular interstitial cells in Poly-D-Glu treated rats labeled with EPO antibody showing EPO production. (See FIG. 22A, second panel)

FIG. 27 shows profiles from a saline-treated rat probed with sense riboprobe (Panel A; negative control) or with an anti-sense riboprobe (Panel B). Panel C is from a Poly-D-Glu-treated rat kidney probed with a sense riboprobe (negative control), whereas panel D is from a Poly-D-Glu-treated rat kidney probed with anti-sense riboprobe. The sites of hybridization are seen as lighter color in the peritubular region in panels B and D (arrows).

DETAILED DESCRIPTION

Figure 1:
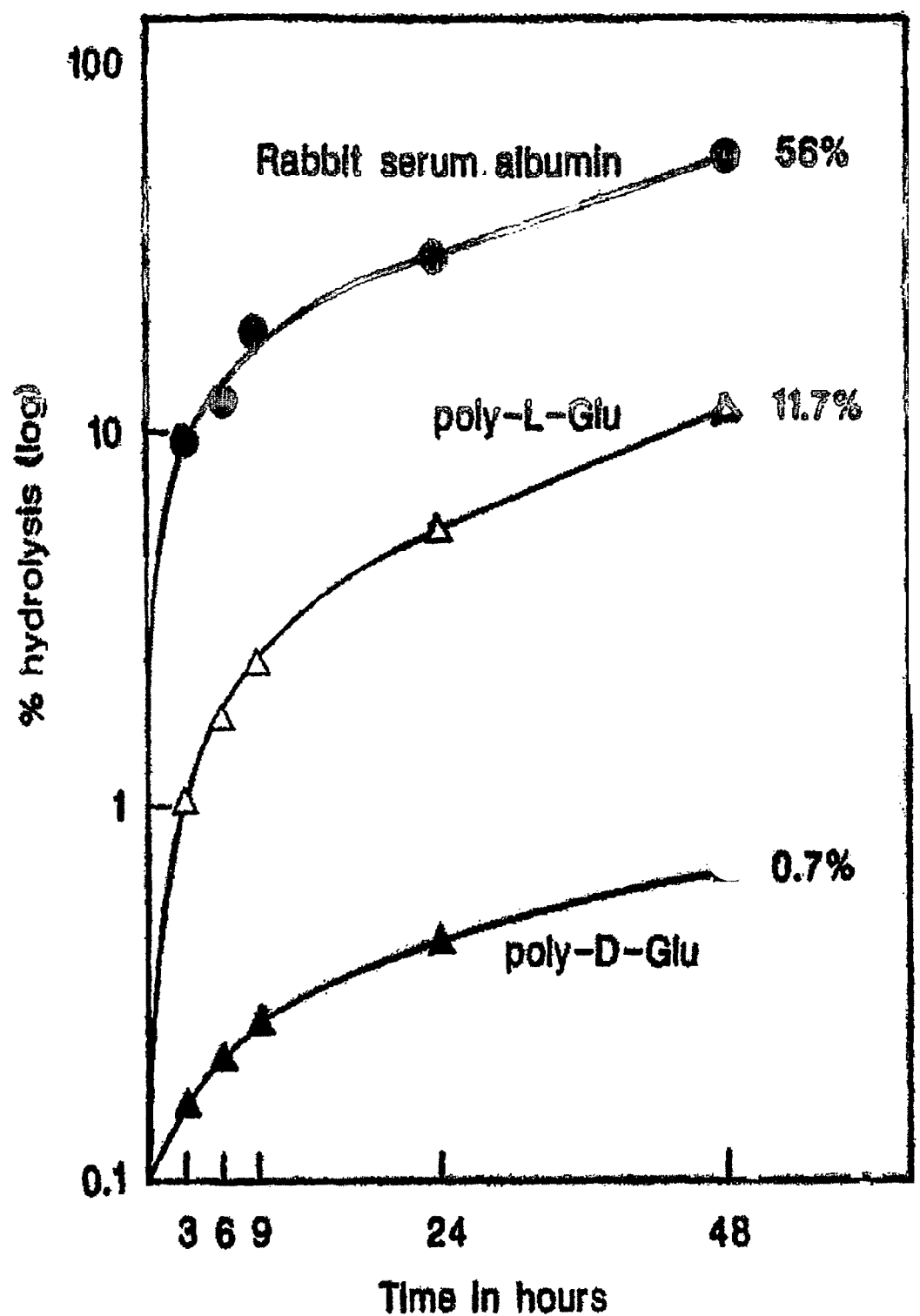
FIG. 1 shows the differences in hydrolysis or degradation rates of poly-L-glutamic and poly-D-glutamic acids. Time-dependent degradation of poly-L-glutamic and poly-D-glutamic acids and rabbit serum albumin by purified lysosomal extracts in vitro in the presence of Cl ions, an activator of cathepsin C. The quantity of the trichloroacetic acid-soluble free amino groups are expressed as percentage of the initial concentration in the incubation, assuming an average MW of 100 for each amino acid residue in serum albumin.
Figure 2:
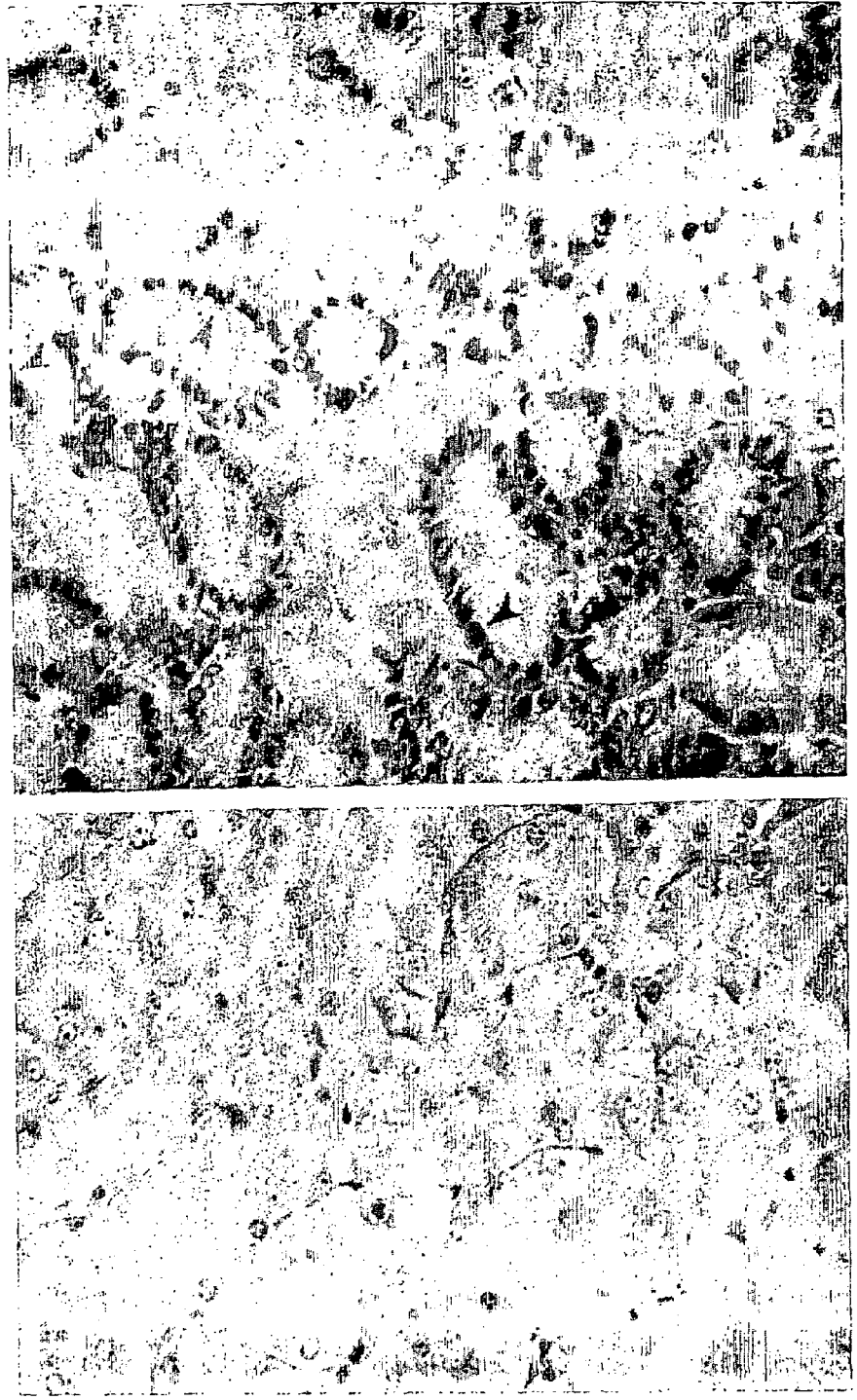
FIG. 2 shows Giemsa staining of paraffin sections of kidneys from a control rat treated with saline and from a rat treated with poly-D-glutamic acid. Female rats were treated for 2 days with saline (A) or poly-D-glutamic acid (B). Arrowheads point to dark inclusions at the basal poles of proximal tubular cells, in the kidney cortex of a poly-D-glutamic acid treated animal. Distal tubules appear to be unaffected.
Figure 3:
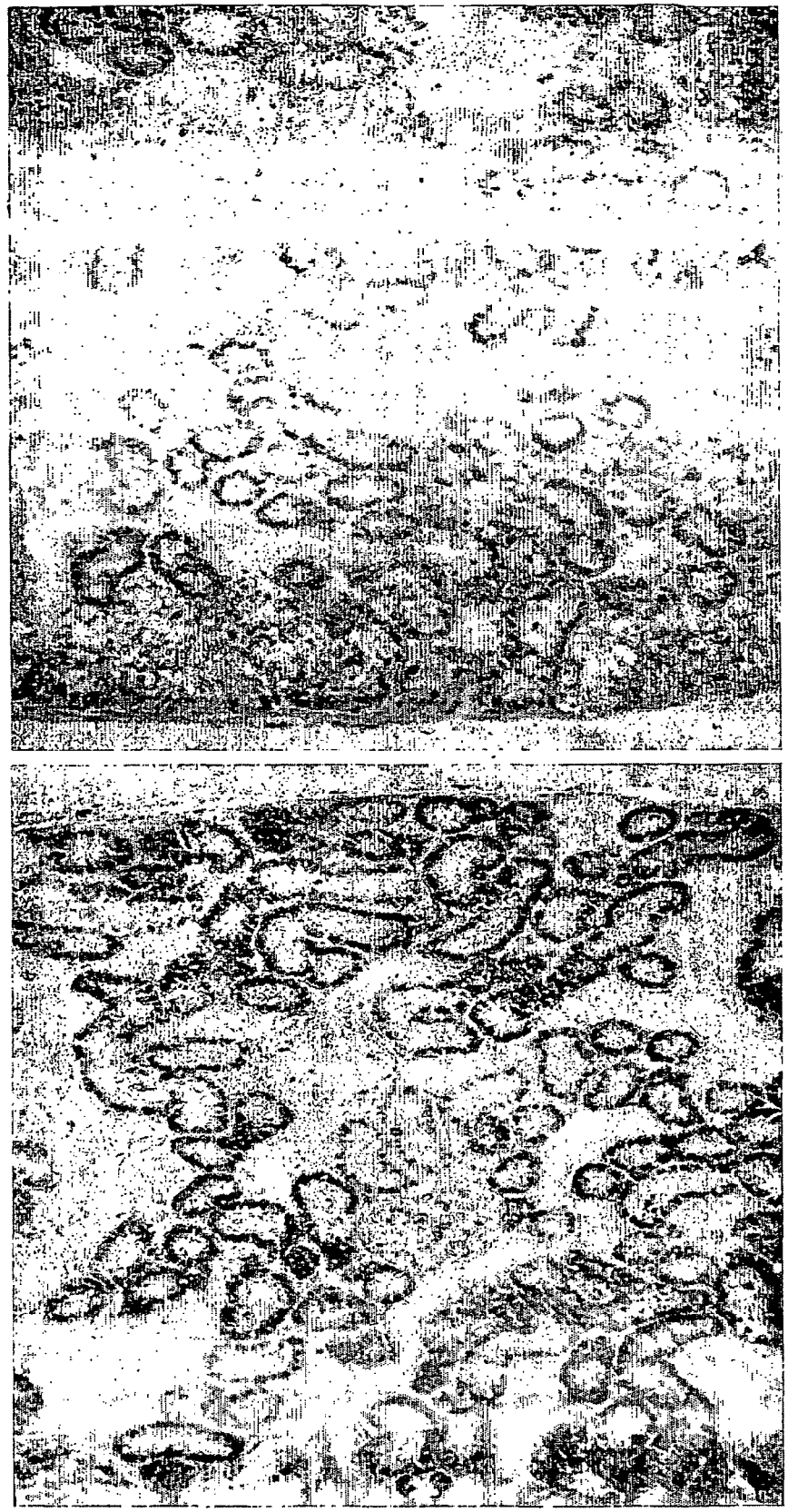
FIG. 3 shows (panel (A)) Giemsa stained paraffin sections of kidney from a rat treated with poly-D-glutamic acid. Panel (B) shows Giemsa stained paraffin sections of kidney from a rat treated with Suramin, a generalized inhibitor of several lysosomal enzymes. This verifies that darkly stained structures in poly-D-glutamic acid treated rat kidneys were lysosomes.
Figure 4:
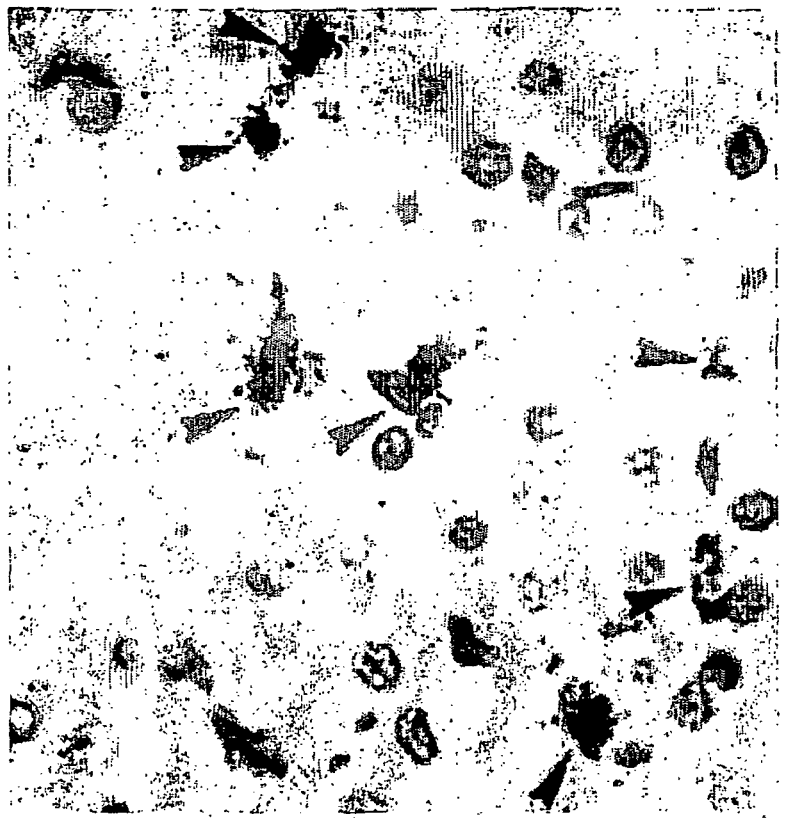
FIG. 4 shows histoautoradiography. Female rats were treated for 2 days with saline (A) or with poly-D-glutamic acid (B). One hour before death, $^3$H-thymidine was injected intraperitoneally. Sections covered with photographic emulsion were exposed for 2 to 3 weeks and counterstained with hematoxylin and eosin. A sparse labeling was found in the control animal, mostly in tubular cells. Poly-D-glutamic acid treatment considerably increased the interstitial cell labeling (B). There was also interstitial infiltration in (B). Magnification is ×425.
Figure 4:
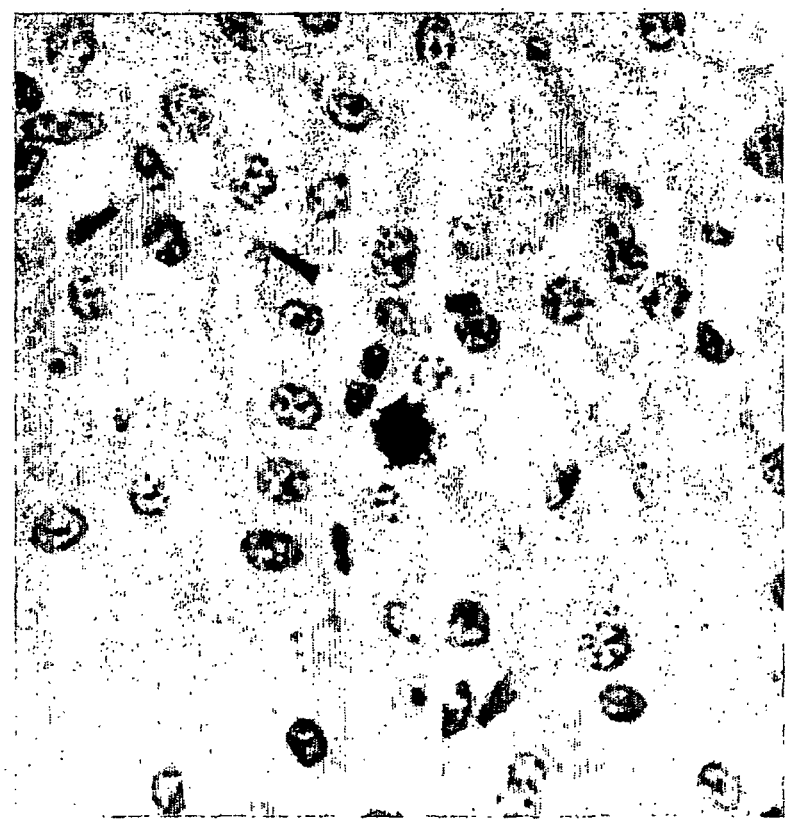
Figure 5:
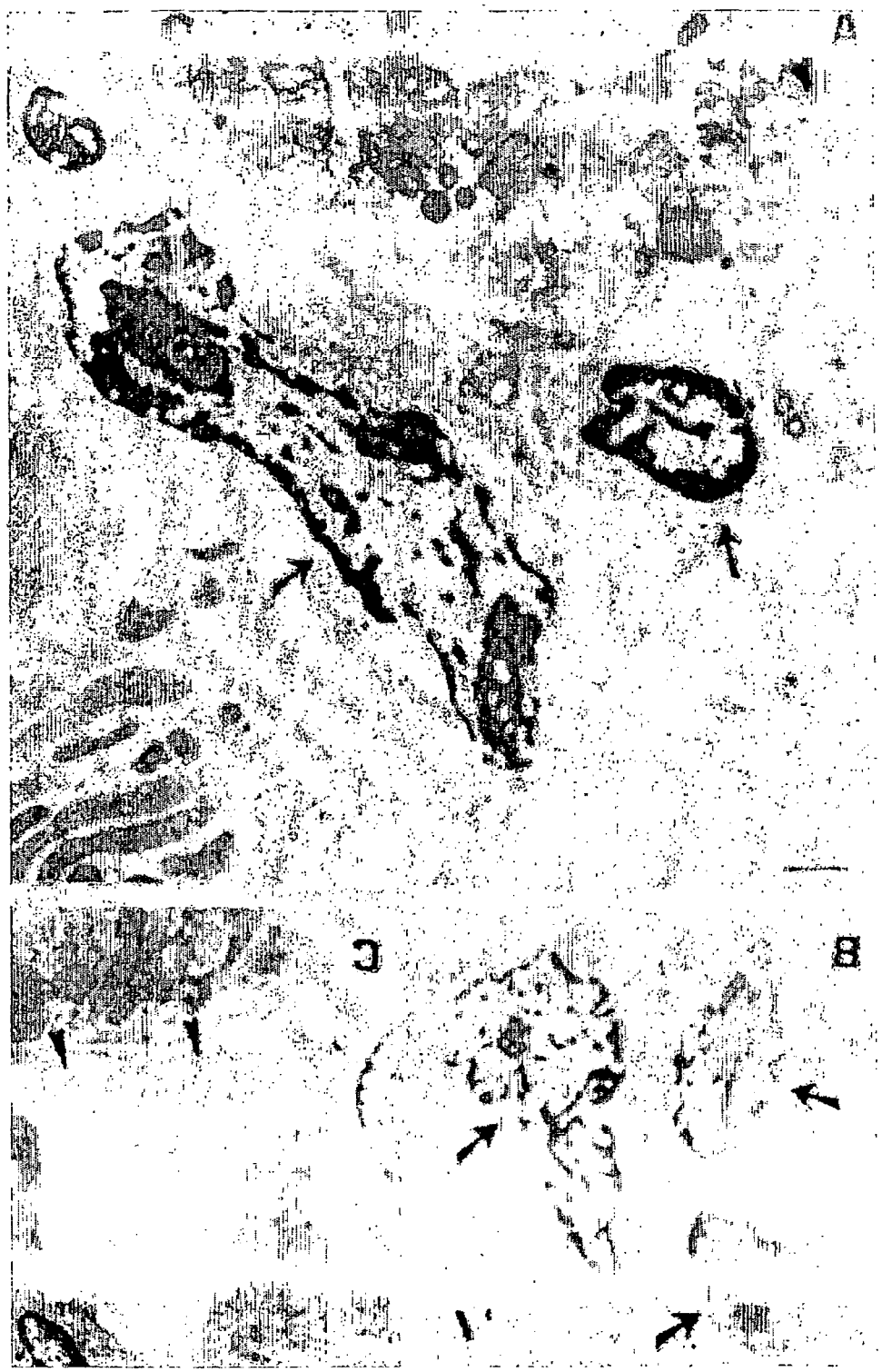
FIG. 5 shows electron micrograph of interstitial cell hyperplasia induced by poly-D-glutamic acid in rat kidney. Female rats were treated for 1 to 2 days with poly-D-glutamic acid, in panel (A), darkly stained round structures considered as normal lysosomes are seen, as well as more distorted and darkly stained inclusions; arrowheads indicate interstitial cell hyperplasia. Panels (B) and (C) show the granular contents of the distorted thesaurismotic (storage) bodies.
Figure 6:
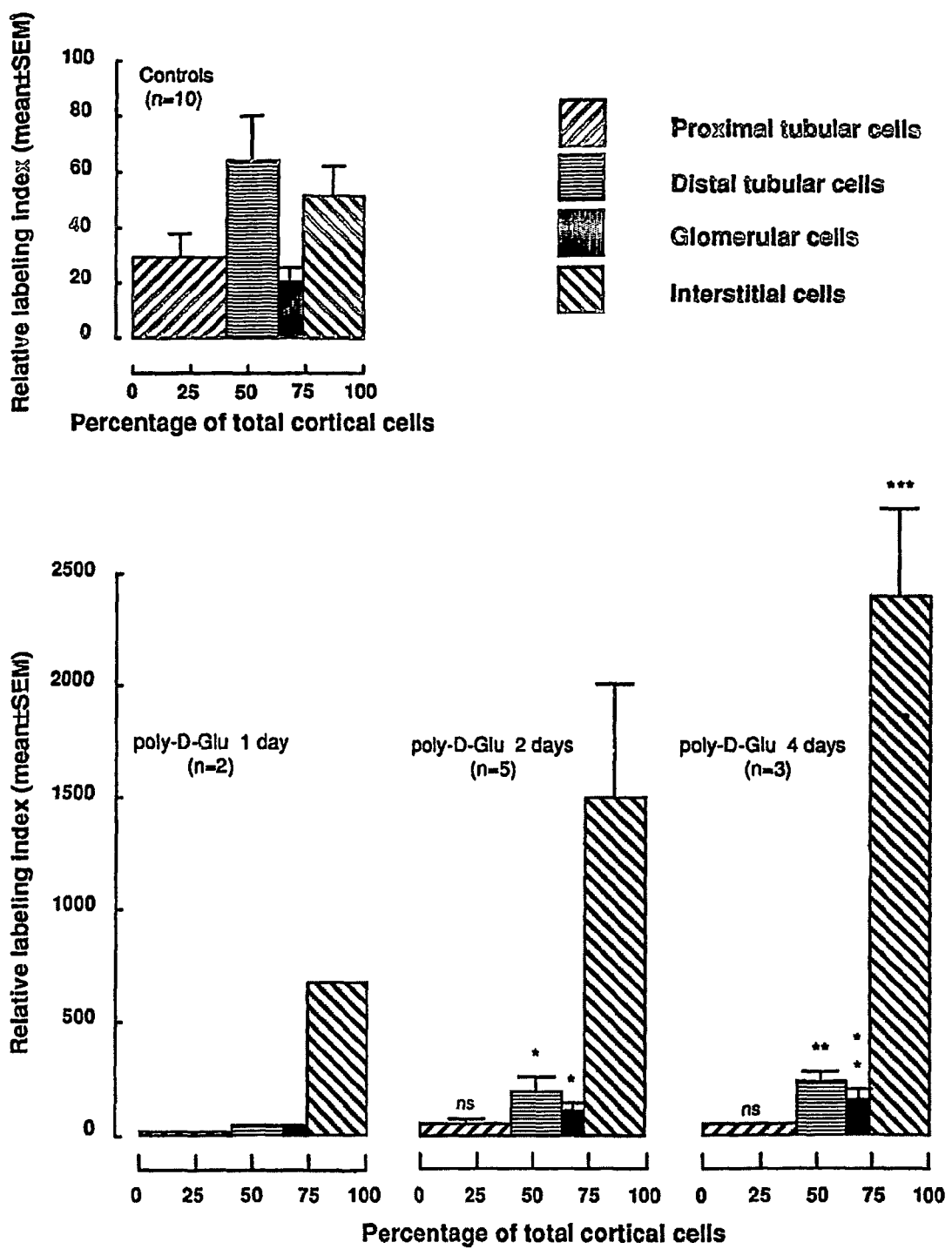
FIG. 6 shows distribution of labeled nuclei. Data were obtained from quantitative analysis of tissue samples collected and processed. Each major cell type is represented by a rectangular block that spans a distance on the abscissa that is equivalent to its proportion among the various cortical cells ($\Delta N_i = N_i / \Sigma N_i$, where $N_i$=the number of nuclei of a given cell type, and $\Sigma N_i$=the sum of the nuclei of all cell types) and displays a height on the ordinate that corresponds to the relative labeling index of these cells (number of labeled nuclei per $\Delta N_i$, mean±SEM). Thus, the area of each block is equivalent to the absolute number of labeled nuclei for that cell type, whereas the total area of blocks in each group of animals is equivalent to the global labeling of that group; *$p<0.05$, $p<0.01$, *$p<0.001$ when compared with the corresponding control values, ns, not significantly different from the corresponding control values. The proliferation of the different cell types at Day 4 was not significantly different from those at Day 2.
Figure 7:
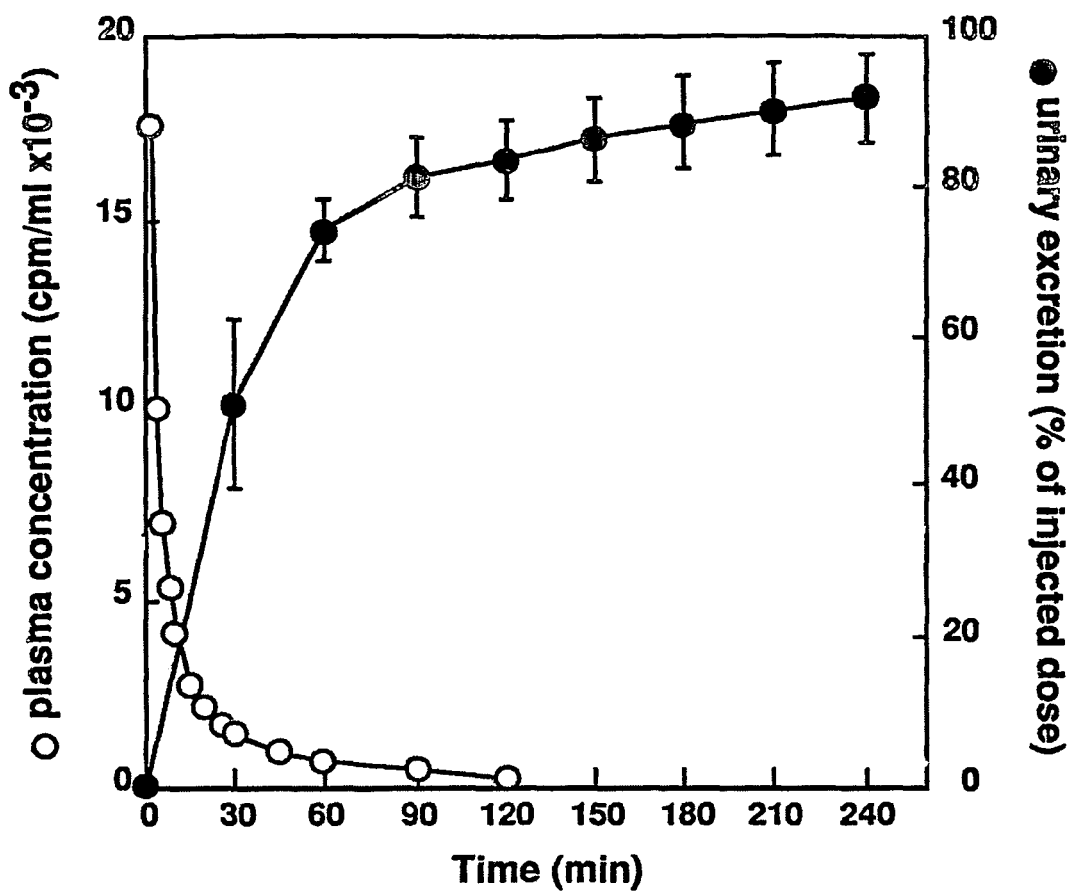
FIG. 7 shows time course of plasma clearance (open circles) and urinary excretion (filled circles) of $^{14}$C-poly-D-glutamic acid in rats after a single intravenous injection of 4 μCi (approximately 12 mg)/kg body weight. Results are given as means+/−SD for three animals.

Before the present compounds, compositions, articles, devices, and/or methods are disclosed and described, it is to be understood that they are not limited to specific methods unless otherwise specified, or to particular reagents unless otherwise specified, as such may, of course, vary. It is also to be understood that the terminology used herein is for the purpose of describing particular embodiments only and is not intended to be limiting.

A. Definitions

Abbreviations: Erythropoietin (EPO).

As used in the specification and the appended claims, the singular forms "a," "an" and "the" include plural referents unless the context clearly dictates otherwise. Thus, for example, reference to "a composition" includes a plurality of such compositions, reference to "the EPIP" is a reference to one or more EPIPs and equivalents thereof known to those skilled in the art, and so forth.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

Throughout the description and claims of this specification, the word "comprise" and variations of the word, such as "comprising" and "comprises," means "including but not limited to," and is not intended to exclude, for example, other additives, components, integers or steps.

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The following are incorporated by reference: U.S. Pat. No. 4,703,008, DNA sequences encoding erythropoietin. U.S. Pat. No. 4,667,016, processes of purifying erythropoietin from fluid. U.S. Pat. No. 5,106,760, a monoclonal antibody specifically immunoreactive with erythropoietin and an immunoassay for quantitative detection of erythropoietin. U.S. Pat. No. 5,597,562, an oral dosage form comprising erythropoietin. U.S. Pat. No. 5,476,653, polyoxymethylene-oxymethylene copolymers in conjunction with biomolecules, including erythropoietin. U.S. Pat. No. 4,935,350, materials and methods for controlling plasmid copy number and stability using a vector, wherein the vector comprises a gene encoding erythropoietin. U.S. Pat. No. 5,756,349, production of erythropoietin using vertebrate cells which can be propagated in vitro and which are capable of growth in culture. U.S. Pat. No. 5,621,080, an isolated erythropoietin glycoprotein having the in vivo biological activity of causing bone marrow cells to increase production of reticulocytes and red blood cells. U.S. Pat. No. 5,618,698, a process for the preparation of an in vivo biologically active erythropoietin product. U.S. Pat. No. 5,955,422, a pharmaceutical composition comprising a therapeutically active amount of erythropoietin. U.S. Pat. No. 5,441,868, a process for the production of a glycosylated erythropoietin polypeptide having the in vivo biological property of causing bone marrow cells to increase production of reticulocytes and red blood cells. U.S. Pat. No. 6,319,499, methods for activating an erythropoietin receptor using antibodies. U.S. Pat. No. 5,354,934, pulmonary administration of erythropoietin. U.S. Pat. No. 5,547,933, a non-naturally occurring erythropoietin glycoprotein product and a method of administering it. U.S. Pat. No. 5,661,125, stable and preserved erythropoietin compositions. U.S. Pat. No. 5,885,574, antibodies which activate an erythropoietin receptor. U.S. Pat. No. 5,830,705, method for recombinant production of human pluripotent granulocyte colony stimulating factor. U.S. Pat. No. 5,856,298, is forms of erythropoietin and methods of preparing such.

Variables such as $R^1$-$R^4$, L, M, X, and carbon as used throughout the application are the same variables as defined herein unless stated to the contrary.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "alkoxy" as used herein is an alkyl group bound through a single, terminal ether linkage; that is, an "alkoxy" group can be defined as —OR where R is alkyl as defined above. A "lower alkoxy" group is an alkoxy group containing from one to six carbon atoms.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" is defined as an aryl group having an alkyl, alkynyl, or alkenyl group as defined above attached to the aromatic group. An example of an aralkyl group is a benzyl group.

The term "hydroxyalkyl group" is defined as an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "carbonate group" is represented by the formula —OC(O)OR, where R can be hydrogen, an alkyl, alkenyl, alkynyl, aryl, aralkyl, cycloalkyl, halogenated alkyl or heterocycloalkyl group described above.

The term "carboxylic acid" is represented by the formula —C(O)OH.

The term "aldehyde" is represent the formula —C(O)H.

The term "keto group" is represented by the formula —C(O)R, where R is alkyl, alkenyl, alkynyl, aryl, aralkyl, cycloalkyl, halogenated alkyl, or heterocycloalkyl group described above.

The term "polyalkylene group" as used herein is a group having two or more CH2 groups linked to one another. The polyalkylene group can be represented by the formula —(CH2)$_n$-, where n is an integer of from 2 to 25.

The term "polyether group" as used herein is a group having the formula —[(CHR)$_n$O]$_m$—, where R is hydrogen or a lower alkyl group, n is an integer of from 1 to 20, and m is an integer of from 1 to 100. Examples of polyether groups include, polyethylene oxide, polypropylene oxide, and polybutylene oxide.

The term "polythioether group" as used herein is a group having the formula —[(CHR)$_n$S]$_m$—, where R is hydrogen or a lower alkyl group, n is an integer of from 1 to 20, and m is an integer of from 1 to 100.

The term "polyimino group" as used herein is a group having the formula —[(CH)$_n$NR]$_m$—, where each R is, independently, hydrogen or a lower alkyl group, n is an integer of from 1 to 20, and m is an integer of from 1 to 100.

The term "polyester group" as used herein is a group that is produced by the reaction between a compound having at least two carboxylic acid groups with a compound having at least two hydroxyl groups.

The term "polyamide group" as used herein is a group that is produced by the reaction between a compound having at least two carboxylic acid groups with a compound having at least two unsubstituted or monosubstituted amino groups.

The term "pro-drug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

The term "metabolite" refers to active derivatives produced upon introduction of a compound into a biological milieu, such as a patient.

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. Compositions and Methods

Disclosed are methods and compositions that are related to the production of erythropoietin and the proliferation of peritubular fibroblast-like cells (PTFBLC), as well as methods involving cell therapy. The production erythropoietin can take place, for example, in vitro, in which increased proliferation of cultured erythropoietin-producing cells, such as PTFBLC, leads to an increased production of erythropoietin, in vivo, in which the proliferation of a subject's erythropoietin-producing cells leads to an increased level of production of erythropoietin, ex vivo, in which cells or tissues harvested from a subject produce erythropoietin.

The disclosed composition can be used to treat any disorder associated with or causing the loss of erythropoietin and any of the symptoms or conditions associated with this loss. For example, the disclosed compositions and methods can be used to treat anemia, such as anemia associated with diseases and disorders such as chronic renal failure, end stage renal disease, malignancies, HIV infections and AIDS, rheumatoid arthritis, myeloma, and myeloplastic syndrome, and other diseases and disorders. In particular, the disclosed compositions and methods can be used to treat any erythropoietin-responsive anemia. The disclosed compositions and methods can also be used to treat Crohn's Disease or ulcerative colitis. The disclosed compositions and methods can also be used to induce angiogenesis in the kidney. The disclosed compositions and methods can also be used to treat organ or tissue transplantation subjects, or to enhance wound healing.

The compositions and methods can be used to stimulate erythropoietin production by inducing the proliferation of PTFBLC. These fibroblasts are capable of producing erythropoietin. Erythropoietin, in turn, stimulates erythropoiesis, or the production of red blood cells. Erythropoiesis is a very precisely controlled physiological mechanism enabling sufficient numbers of red blood cells to be available in the blood for proper tissue oxygenation. The formation of red blood cells occurs in the bone marrow.

The stimulation of erythropoietin can be a direct or indirect effect of the disclosed compounds. A direct effect is an effect on the erythropoietin-producing cells directly by the disclosed compounds. An indirect effect is an effect on erythropoietin-producing cells resulting from the effect of the disclosed compounds on other cells. For example, the compounds can stimulate proximal tubular cells to release certain molecules that stimulate the production of erythropoietin producing PTFBLC in a paracrine fashion. A lysosomal storage condition in the proximal tubular cells caused by the compounds disclosed herein has been shown to cause proliferation of PTFBLC.

Figure 28:
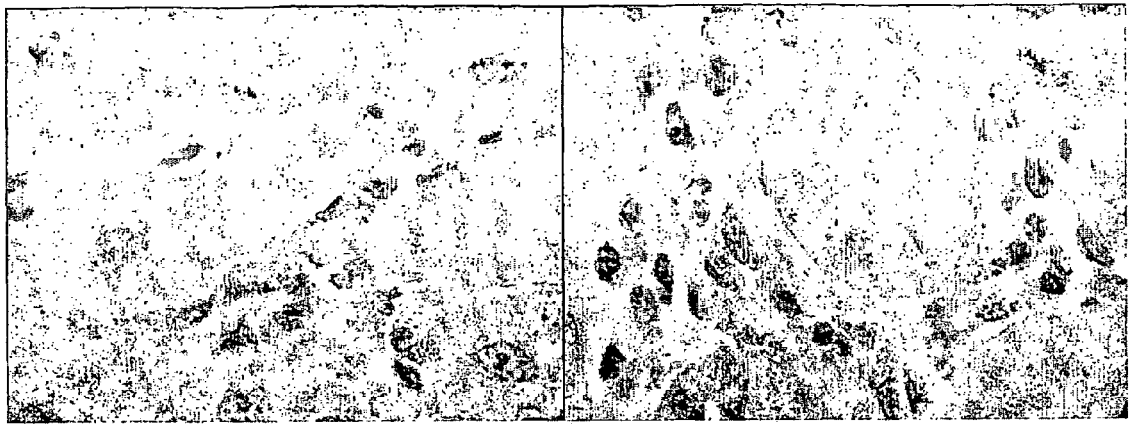
FIG. 28 shows the persistence of EPO-producing peritubular interstitial cells in rat kidney even after the cessation of Poly-D-glutamic acid treatment Groups of rats were treated with either saline (N=2) or with Poly-D-Glu (250 mg/kg/day for 4 consecutive days, sc; N=3), and were sacrificed six days after the cessation of treatment. Formalin fixed and paraffin-embedded kidneys from these rats were immunohistichemically labeled with EPO antibody. Panel A shows a representative profile from a saline treated control rat. Panel B shows a representative profile from a Poly-D-Glu-treated rat. The sites of EPO protein localization are visualized as brown coloration (marked with arrows in panel A). All Poly-D-Glu-treated rats in this series (N=3) showed consistent labeling of peritubular cells, which in turn was comparable to the labeling in the other two series of rats that were sacrificed one day after the cessation of Poly-D-Glu administration (FIGS. 23 and 24).

Disclosed are corn positions that induce fibroblasts to produce erythropoietin even after the cessation of administration of the disclose compounds. (FIG. 28, Example 5). Cells isolated from subjects that are induced to produce erythropoietin even after cessation of administration of the disclosed compounds can be further refined and manipulated in the laboratory to develop into "cell lines' that perpetually produce erythropoietin either in vivo or in vitro when infused or transplanted into another subject.

The induction of cells to produce erythropoietin can also be achieved by in vitro approaches. In such an approach, the PTFBLC are conditioned in vitro either by co-culture technique or by conditioned media or both.

Also disclosed are systems and methods which can be used to identify molecules which are capable of stimulating erythropoietin production. For example, administration of the disclosed compounds to a subject or exposure of cells or tissues to the disclosed compounds can produce signal molecules that mediate proliferation of erythropoietin-producing cells and induction of increased erythropoietin production. For example, the disclosed compounds can stimulate proximal tubular cells, thereby producing a non-lethal lysosomal storage condition. The cells then release signal molecules that can stimulate the proliferation of EPO-producing PTFBLC. The disclosed compounds can be used to identify such signal molecules by, for example, monitoring changes in the types and levels of molecules when the disclosed compounds are administered or applied. Also disclosed are systems and methods of identifying compounds that can modulate production of erythropoietin. For example, signal molecules involved in erythropoietin production identified using the disclosed methods can be blocked or stimulated by compounds. Such compounds can be identified by, for example, administering to a subject, or exposing cells or tissues to, one or more of the disclosed compounds and a test compound in combination and comparing the effect on erythropoietin production with the effect on erythropoietin production when only the same disclosed compositions are administered or applied.

In some forms, the disclosed methods can involve bringing into contact cells in culture and one or more of the disclosed compositions and harvesting erythropoietin from the cells. In some forms, the disclosed methods can involve administering one or more of the disclosed compositions to a subject, harvesting erythropoietin-producing cells from the subject, and harvesting erythropoietin from the cells. In some forms, the disclosed methods can involve administering one or more of the disclosed compositions to a subject, harvesting proximal tubular cells from the subject, incubating the proximal tubular cells with cells in culture (such as PTFBLC or other fibroblast cells), and harvesting erythropoietin from the erythropoietin producing cells. In some forms, the disclosed methods can involve administering one or more of the disclosed compositions to a subject, harvesting proximal tubular cells from the subject, harvesting signal molecules from the proximal tubular cells, bringing into contact erythropoietin producing cells in culture and the signal molecules, and harvesting erythropoietin from the cells. In some forms, the disclosed methods can involve bringing into contact one or more of the disclosed compositions and a co-culture of proximal tubular cells and fibroblasts, and harvesting erythropoietin from the cells.

Also disclosed are cells exposed to one or more of the disclosed compositions. Such cells can be, for example, cells in culture, cells harvested from a subject, or cells harvested from a subject to which a disclosed composition has been administered. Such cells can be used for any purpose, including use in the disclosed method and as research tools. These cells can be fibroblasts, such as peritubular interstitial cells or proximal tubular cells, or any cells capable of directly or indirectly stimulating the production or erythropoietin. These cells can be continuously or routinely exposed to the compounds disclosed herein, or can be transformed or modified by the disclosed compounds such that they continue to proliferate or produce erythropoietin without after contact with the disclosed compounds or compositions without the need for continuous or multiple contacts.

Also disclosed are methods of making cells that produce erythropoietin comprising administering to the cells an effective amount of an EPIP. The EPIP can be administered directly to the cell producing erythropoietin, or can be indirectly used to stimulate the erythropoietin producing cell by, for example, administering the EPIP to a cell that then stimulates the erythropoietin producing cell to produce erythropoietin. An example of such a cell is a proximal tubular cell that when stimulated by EPIP produces a non-lethal lysosomal storage condition. The cells then release signal molecules that stimulates the proliferation of EPO-producing peritubular cells. The cells generated by this method can be continuously or regularly exposed to the EPIP or, alternatively, can continue to produce erythropoietin after exposure to EPIP. The cells can continue to produce erythropoietin after 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days, or longer, after exposure to the EPIP. Also disclosed are cells produced by the method disclosed above.

Also disclosed are tissues exposed to one or more of the disclosed compositions. Such tissues can be, for example, tissues harvested from a subject or tissues harvested from a subject to which a disclosed composition has been administered. Examples of tissues expressing erythropoietin include, but are not limited to, kidney and liver tissues. Such tissues can be used for any purpose, including use in the disclosed method and as research tools. Also disclosed are non-human animals exposed to one or more of the disclosed compositions.

Also disclosed are recombinant, transfected, or transgenic cells producing one or more of the disclosed poly amino acids from an introduced construct encoding the poly amino acids. Some such cells can be administered to a subject as a method of treatment. Also disclosed are transgenic non-human animals producing one or more of the disclosed poly amino acids from one or more introduced constructs (e.g., transgenes) encoding the poly amino acids. Such transgenic non-human animals can, but need not, be capable of germline transmission of the introduced constructs.

1. Compositions
i. Erythropoietin Production Inducing Peptides

Disclosed are Erythropoietin Production Inducing Peptides (EPIPs). EPIPs are peptides that are capable of directly or indirectly stimulating proliferation of fibroblasts, which in turn produce erythropoietin. Some forms of EPIPs have a structure which comprises at least two residues having the formula I or II:

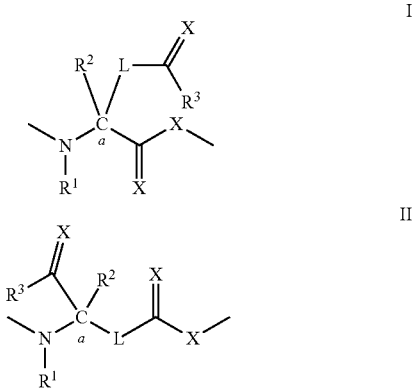

wherein each X can be, independently, oxygen or sulfur; L is not present or when L is present, L can be (1) oxygen, (2) $NR^4$, or (3) a substituted or unsubstituted polyalkylene group, polyether group, polyamide group, polyester group, polyimino group, aryl group, or polythioether group; $R^1$, $R^2$, $R^3$ and $R^4$ can be, independently, hydrogen, halide, alkyl, alkenyl, alkynyl, aryl, cycloalkyl, aralkyl, alkoxy, hydroxyalkyl, alkoxyalkyl, a keto group, an ester group, a carbonate group, an aldehyde group, or a carboxylic acid group; and the stereochemistry at carbon a is substantially R, substantially S, or a mixture thereof of R and S; wherein the residues having the formula I and II are neutral or ionic, wherein each of the residues can have the formula I each of the residues can have the formula II, or the residues can be a mixture of formulae I and II.

Depending upon the techniques used to prepare the peptide and the groups present in the residue precursors of I and II, amide formation can occur at two possible sites during peptide synthesis, which are represented in formulae I and II. For example, in glutamic acid, two carboxylic groups are present. By varying reaction conditions or modifying one of the carboxylic groups so that it is inert, amide formation can occur at either carboxylic group. Alternatively, amide formation can occur at both carboxylic groups. In one aspect, the peptide contains at least two residues having only the formula I. In another aspect, the peptide contains at least two residues having only the formula II. In further aspect, the peptide contains at least one residue having only the formula I and at least one residue having the formula II. It should be noted that Erythropoietin Production Inducing Peptides include, but are not limited to "peptides" as that term is understood in the art. For example, EPIPs containing residues of formula II may not be considered a traditional peptide. The term Erythropoietin Production Inducing Peptide is used merely as a convenient way of referring to useful forms of the disclosed compositions.

The residues having the formulae I and II can be optically active (D or L) or racemic (D and L). The stereochemistry at carbon a in formulae I and II can vary. In one aspect, the stereochemistry at carbon a is substantially R, substantially S, or a mixture of R and S with varying amounts of the R and S enantiomers. The terms "R" and "S" with respect to the stereochemistry at carbon a are also referred to in the art as "D" and "L," respectively. The term "substantially" with respect to the stereochemistry at carbon a refers to greater than 90%, 92%, 94%, 95%, 96%, 97%, 98%, or 99% of one enantiomer with respect to the other enantiomer. Using techniques known in the art, it is possible to vary the stereochemistry at carbon a of the residue precursor prior to peptide synthesis.

The variable L in formulae I and II, which is a linker or tether, is optional. When L is not present, carbon a is bonded directly to $C(X)R^3$ in formula I and $C(X)X$ in formula II. In one aspect, when L is present in formulae I and II, L can be a polyalkylene group having the formula $—(CH_2)_n—$, where n is an integer of from 1 to 20, 2 to 10, 2 to 8, 2 to 6, or 2 to 4.

In one aspect, in formulae I and II, (1) each X is oxygen, (2) $R^1$ and $R^2$ are hydrogen, (3) L is a polyalkylene group, (4) $R^3$ is hydroxyl, alkoxy, or OM, and M is a cation, or any combination of (1)-(4). In another aspect, in formulae I and II, each X is oxygen, $R^1$ and $R^2$ are hydrogen, $R^3$ is hydroxyl or OM, wherein M is a cation, L is $CH_2CH_2$, and the stereochemistry at carbon a is substantially R or substantially S. In this aspect, when $R^3$ is a hydroxyl group, the residue is neutral. Conversely, when $R^3$ is OM, the residue is ionic due to the presence of the cation M.

Depending upon the application, the residues having the formulae I and II can be neutral or ionic (i.e., cationic or anionic). In one aspect, when formulae I and II are ionic, they can encompass any pharmaceutically-acceptable salt. In one aspect, pharmaceutically acceptable salts are prepared by treating the free acid with an appropriate amount of a pharmaceutically acceptable base to produce the corresponding anionic compound. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. In another aspect, the cationic forms of the residues having the formula I and II can be prepared by treating the peptide with an acid such as, for example, an organic acid. In this aspect, the lone pair electrons of one or more amino groups can be protonated. The degree of protonation or deprotonation of the peptide will vary depending upon the amount of acid or base, respectively, that is used.

In another aspect, the peptide is composed of only residues having the formula I, residues having the formula II, or a mixture of residues having the formulae I and II. In this aspect, the peptide contains no other residues other than those depicted in formulae I and/or II. For example, the peptide can be poly-D-glutamic acid, poly-L-glutamic acid, poly-D-aspartic acid, poly-L-aspartic acid, or a mixture thereof. In one aspect, the peptide can also be poly-D-aspartic acid, or a mixture of poly-D-aspartic acid and poly-D-glutamic acid and/or poly-L-glutamic acid.

The molecular weight of the peptide can vary. In one aspect, the peptide can be from 1 kDa to 200 kDa. In another aspect, the peptide can be from 10 kDa to 7 kDa, 10 kDa to 60 kDa, 10 kDa to 50 kDa, 10 kDa to 40 kDa, 10 kDa to 30 kDa, or 15 kDa to 25 kDa. The peptides containing the residues having the formula I and/or II can be prepared using techniques known in the art, such as by the Merrifield solid phase method.

ii. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis).

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of *Proteins by Native Chemical Ligation. Science,* 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with fall biological activity (deLisle Milton R C et al., Techniques in Protein Chemistry IV. Academic Press, New York, pp. 257-267 (1992)).

Alternatively, peptides containing D-amino acids can be linearly linked by alternating with short or long pieces of L-amino acid containing peptides, to yield large synthetic peptides. These large synthetic peptides, upon administration to subjects, are cleaved by proteolytic enzymes at the L-amino acid containing portions, leaving the D-amino acid containing peptides intact, which enter the bloodstream circulation and thus reach the target organs such as the kidney.

iii. Erythropoietin

Erythropoietin is a 30,400 M.W. glycoprotein produced primarily in the kidneys in adults and only to a small extent in the liver. The erythropoietin gene is also expressed in the brain and some other tissues, but its physiologic role in these locations has not been established. The gene for erythropoietin is present as a single copy on chromosome 7. The erythropoietin gene is highly conserved on an evolutionary basis with over 90% homology between human and simian genes and an 80% homology between human and rodent erythropoietin genes. The structure and other aspects of erythropoietin are known and are described in, for example, Browne et al., "Erythropoietin: Gene Cloning, Protein Structure, and Biological Properties," Cold Spring Harbor Symposia on Quantitative Biology, L1, 693-702 (1986); and U.S. Pat. No. 5,106,954 (Fibi et al.) "Erythropoietin *Peptides*," which are hereby incorporated by reference at least for material related to the structure of erythropoietin and its gene.

The amino acid sequence of full length human erythropoietin is found in SEQ ID NO: 1 (Accession No. X02158):

```
MGVHECPAWLWLLLSLLSLPLGLPVLGAPPRLICDSRVLQRYLLEAKEAE

NITTGCAEHCSLNENITVPDTKVNFYAWKRMEVGQQAVEVWQGLALLSEA

VLRGQALLVNSSQPWEPLQLHVDKAVSGLRSLTTLLRALGAQKEAISPPD

AASAAPLRTITADTFRKLFRVYSNFLRGKLKLYTGEACRTGDR
```

The corresponding nucleotide sequence of full length human erythropoietin is found in SEQ ID NO: 2:

```
agcttctggg cttccagacc cagctacttt gcggaactca gcaacccagg catctctgag tctccgccca agaccgggat gccccccagg aggtgtccgg gagcccagcc tttcccagat agcagctccg ccagtcccaa gggtgcgcaa ccggctgcac tcccctcccg cgacccaggg cccgggagca gcccccatga cccacacgca cgtctgcagc agcccgtca gccccggagc ctcaacccag gcgtcctgcc cctgctctga ccccgggtgg ccctaccc tggcgacccc tcacgcacac agcctctccc ccaccccac ccgcgcacgc acacatgcag ataacagccc cgaccccgg ccagagccgc agagtccctg ggccacccg gccgctcgct gcgctgcgcc gcaccgcgct gtcctccgg agccggaccg gggccaccgc gcccgctctg ctccgacacc gcgcccctg gacagccgcc ctctcctcca ggcccgtggg gctggccctg caccgccgag cttcccggga tgagggcccc cggtgtggtc acccggcgcc ccaggtcgct gagggacccc ggccaggcgc ggagatgggg gtgcacggtg agtactcgcg ggctgggcgc tcccgcccgc ccgggtccct gtttgagcgg ggatttagcg ccccggctat tggccaggag gtggctgggt tcaaggaccg gcgacttgtc aaggaccccg gaaggggag ggggtgggg cagcctccac gtgccagcgg ggacttgggg gagtccttgg ggatggcaaa aacctgacct gtgaagggga cacagtttgg gggttgaggg gaagaaggtt tgggggttc tgctgtgcca gtggagagga agctgataag ctgataacct gggcgctgga gccaccactt atctgccaga ggggaagcct ctgtcacacc aggattgaag tttggccgga gaagtggatg ctggtagcct ggggtgggg tgtgcacacg gcagcaggat tgaatgaagg ccagggaggc agcacctgag tgcttgcatg gttggggaca ggaaggacga gctggggcag agacgtgggg atgaaggaag ctgtccttcc acagccaccc ttctccctcc ccgcctgact ctcagcctgg ctatctgttc tagaatgtcc tgcctggctg tggcttctcc tgtccctgct gtcgctccct ctgggcctcc cagtcctggg cgccccacca cgcctcatct gtgacagccg agtcctgcag aggtacctct tggaggccaa ggaggccgag aatatcacgg tgagacccct tccccagcac attccacaga actcacgctc agggcttcag ggaactcctc ccagatccag gaacctggca cttggtttgg ggtggagttg ggaagctaga cactgccccc ctacataaga ataagtctgg tggccccaaa ccatacctgg
```

```
-continued
aaactaggca aggagcaaag ccagcagatc ctacgcctgt ggccagggcc agagccttca
gggacccttg actccccggg ctgtgtgcat ttcagacggg ctgtgctgaa cactgcagct
tgaatgagaa tatcactgtc ccagacacca aagttaattt ctatgcctgg aagaggatgg
aggtgagttc ctttttttt ttttttcctt tcttttggag aatctcattt gcgagcctga
ttttggatga aagggagaat gatcgaggga aaggtaaaat ggagcagcag agatgaggct
gcctgggcgc agaggctcac gtctataatc ccaggctgag atggccgaga tgggagaatt
gcttgagccc tggagtttca gaccaaccta ggcagcatag tgagatcccc catctctaca
aacatttaaa aaaattagtc aggtgaagtg gtgcatggtg gtagtcccag atatttggaa
ggctgaggcg ggaggatcgc ttgagcccag gaatttgagg ctgcagtgag ctgtgatcac
accactgcac tccagcctca gtgacagagt gaggccctgt ctcaaaaag aaaagaaaaa
agaaaaataa tgagggctgt atggaatacg ttcattattc attcactcac tcactcactc
attcattcat tcattcattc aacaagtctt attgcatacc ttctgtttgc tcagcttggt
gcttgggct gctgagggc aggagggaga gggtgacatc cctcagctga ctcccagagt
ccactccctg taggtcgggc agcaggccgt agaagtctgg cagggcctgg ccctgctgtc
ggaagctgtc ctgcggggcc aggccctgtt ggtcaactct tcccagccgt gggagcccct
gcagctgcat gtggataaag ccgtcagtgg ccttcgcagc ctcaccactc tgcttcgggc
tctgggagcc caggtgagta ggagcggaca cttctgcttg ccctttctgt aagaagggga
gaagggtctt gctaaggagt acaggaactg tccgtattcc ttcccttct gtggcactgc
agcgacctcc tgtttctcc ttggcagaag gaagccatct cccctccaga tgcggcctca
gctgctccac tccgaacaat cactgctgac actttccgca aactcttccg agtctactcc
aatttcctcc ggggaaagct gaagctgtac acagggagg cctgcaggac aggggacaga
tgaccaggtg tgtccacctg ggcatatcca ccacctccct caccaacatt gcttgtgcca
caccctcccc cgccactcct gaacccgtc gaggggctct cagctcagcg ccagcctgtc
ccatggacac tccagtgcca ccaatgacat ctcaggggcc agaggaactg tccagagagc
aactctgaga tctaaggatg tcacagggcc aacttgaggg cccagagcag gaagcattca
gagagcagct ttaaactcag ggacagaccc atgctgggaa gacgcctgag ctcactcggc
accctgcaaa attgatgcca ggacacgctt tggaggcgat ttacctgttt tcgcacctac
catcagggac aggatgacct ggagaactta ggtggcaagc tgtgacttct ccaggtctca
cgggcatggg cactcccttg gtggcaagag ccccttgac accggggtgg tgggaaccat
gaagacagga tgggggctgg cctctggctc tcatggggtc caacttttgt gtattcttca
acctcattga caagaactga aaccaccaat atgactcttg gcttttctgt tttctgggaa
cctccaaatc ccctggctct gtcccactcc tggcagca
```

There are numerous variants of the erythropoietin protein that are known and herein contemplated. In addition, to the known functional erythropoietin strain variants there are derivatives of the erythropoietin proteins which also function in the disclosed methods and compositions, as well as recombinant erythropoietins that also function in the disclosed methods. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isolelucine | Ile | I |
| leucine | Leu | L |
| lysine | Lys | K |
| phenylalanine | Phe | F |
| proline | Pro | P |
| serine | Ser | S |
| threonine | Thr | T |
| tyrosine | Tyr | Y |
| tryptophan | Trp | W |
| valine | Val | V |

TABLE 2

Amino Acid Substitutions
Original Residue Exemplary Conservative
Substitutions, others are known in the art.

Ala and Ser
Arg and Lys, Gln
Asn and Gln, His
Asp and Glu
Cys and Ser
Gln and Asn, Lys
Glu and Asp
Gly and Pro
His and Asn, Gln
Ile and Leu, Val
Leu and Ile, Val
Lys and Arg; Gln
Met and Leu, ile
Phe and Met, Leu, Tyr
Ser and Thr
Thr and Ser
Trp and Tyr
Tyr and Trp, Phe
Val and Ile, Leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., fysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of erythropoietin. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad.

Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad: Sci. USA* 86:7706-7710, 1989, Jaeger et al. *Methods Enzymol* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO: 1 is set forth in SEQ ID NO: 2. It is understood that while no amino acid sequence indicates what particular DNA sequence encodes that protein within an organism, where particular variants of a disclosed protein are disclosed herein, the known nucleic acid sequence that encodes that protein in the particular area from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino, acid into a peptide chain in a site specific way (Thorson et al., Methods in Molec. Biol. 77:43-73 (1991), Zoller, Current Opinion, in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Any form of erythropoietin can be used in or with the disclosed compositions and methods. For example, recombinant erythropoietin and variant erythropoietins can be used. Recombinant erythropoietin is any form of erythropoietin produced using recombinant or transgenic technology. For example, recombinant erythropoietin can be derived from the expression of an exogenous DNA sequence that has been transfected into a non-human eukaryotic host cell, as described in Lin et al. (U.S. Pat. No. 4,703,008), herein incorporated in its entirety by reference. Recombinant erythropoietin can have the same or a different structure and function from any naturally occurring erythropoietin. Naturally occurring erythropoietin is glycosylated. The glycosylation of recombinant erythropoietin is either limited or different from it's natural counterpart or both.

iv. Cells

Also disclosed are cells, wherein the cells can be propagated in vitro and which are capable upon growth in culture of producing erythropoietin when said cells are exposed to a composition as described herein. The cells can be kidney cells, proximal tubular cells or PTFBIC. The cells can be induced to proliferate fibroblast cells which in turn produce erythropoietin, or can be directly stimulated to produce erythropoietin. The cells can be continuously or routinely exposed to the compounds described herein, or they can be exposed for a period of time and then transformed or phenotypically altered to perpetually produce erythropoietin. The cells can be maintained in culture and the erythropoietin can be harvested from the cells, or the cells can be transplanted or infused into a subject to increase the erythropoietin production of the subject. The cells can be in the form of ex vivo tissues or organs, such as the kidney.

v. Erythropoietin Production

Erythropoietin production can be monitored using, for example, radioimmunoassay (RIA), Western Blot Anaysis, SDS polyacrylamide gel electrophoresis (PAGE), Northern hybridization analysis, immunocytochemistry, enzyme-linked immunosorbant assay (ELISA), enzyme-immunoassay (EIA), or in situ hybridization or appropriate biological assay that measures the activity of erythropoietin using a self-contained biological system. The cells can produce 1 U to 1000 U of erythropoietin per $10^6$ cells in 48 hours. The cells can produce from 1 U to 500 U of erythropoietin per $10^6$ cells in 48 hours. The cells can produce from 1 U to 100 U of erythropoietin per $10^6$ cells in 48 hours.

vi. Administration

The disclosed compositions can be administered to cells, tissues and subjects in different amounts, depending on the amount of erythropoietin to be produced, the cell type, and other factors. EPIPs can be administered in the amount of 1 mg to 10,000 mg a day. EPIPs can be administered in the amount of 10 mg to 1000 mg a day. EPIPs can be administered in the amount of 100 mg to 500 mg a day. EPIPs can be administered in the amount of 500 mg a day.

The cells producing erythropoietin can also be administered to the subject by methods known in the art regarding cell therapy, such as those taught in Schiendhelm et al., Ex Vivo Cell Therapy, Academic Press, Los Angeles, Cali., 1999, herein incorporated in it's entirety by reference for the teachings applicable to cell therapy. The cells are stimulated to produce erythropoietin in culture, administered to a subject, where they continue to produce erythropoietin. Cells for therapeutic purposes can be delivered in various ways. For example, they may be infused, injected at various sites or surgically implanted in aggregated form or along with solid supports or encapsulating materials. Any matrices, fibers, beads, or other materials which are used in addition to the cells including excipients, additional active components, or medical devices.

Methods of culturing and administering cells for cell therapy can be found in the FDA Guide "Guidance for Human Somatic Cell Therapy and Gene Therapy", U.S. Department of Health and Human Services Center for Biologics Evaluation and Research, March 1998, available online at www.fda.gov/cber/gdlns/somgene.pdf.

vii. Compositions Identified by Screening with Disclosed Compositions

The disclosed compositions can be used as targets for any technique to identify molecules or macromolecular molecules that interact with proximal tubular cells in a desired way, such as proliferation of PTFBLC. The EPIPs disclosed herein can be used in screening methods to identify proliferating fibroblasts, as well as in comparison assays. Also disclosed are the compositions that are identified through such screening techniques in which the compositions disclosed herein or portions thereof.

It is understood that when using the disclosed compositions in screening methods, molecules, such as macromolecular molecules, will be identified that have particular desired properties such as proliferation of PTFBLC. The molecules identified and isolated when using the disclosed compositions, such as, proliferating PTFBLC, are also disclosed. Thus, the products produced using the screening approaches that involve the disclosed compositions, such as proliferating cells, are also considered herein disclosed.

2. Methods of Using the Compositions i. Pharmaceutical Carriers/Delivery of Pharmaceutical Products The disclosed compositions can be used in, for example, methods of treatment. For this purpose, the compositions can contain erythropoietin, EPIP, or a combination of both. The disclosed compositions for use in methods of treatment can be referred to as pharmaceutical compositions. The erythropoietin can be naturally occurring erythropoietin, or recombinant or synthetic erythropoietin. Variant forms of erythropoietin can also be used.

The disclosed methods can be used to treat anemia, associated with diseases and disorders such as chronic renal failure, end stage renal disease, malignancies, HIV infections and AIDS, rheumatoid arthritis, myeloma, and myeloplastic syndrome, and other diseases and disorders. The disclosed compositions and methods can also be used to treat Crohn's Disease or ulcerative colitis. The disclosed compositions and methods can also be used to cause angiogenesis in the kidney. The disclosed compositions and methods can also be used to treat organ or tissue transplantation subjects, or to enhance wound healing. The disclosed compositions and methods can also be used to enhance athletic and other physical performances including life enhancement supplement to increase the energy level of subjects.

The compositions can be administered orally, rectally, subcutaneously, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying or droplet mechanism, or through aerosolization. Administration of the compositions by inhalant can be through the nose or mouth via delivery by a spraying or droplet, mechanism. Delivery can also be directly to any area of the respiratory system (e.g., lungs) via intubation or inhalation. The compositions can also be delivered by an implantable drug delivery system, such as an osmotic pump. The osmotic pump can be an osmotic mini-pump, and can be implanted subcutaneously for constant release, and can be implanted subcutaneously for constant release. The drug delivery system can also be external to the subject. The exact amount (e.g., dosage) of the compositions required will vary from subject to subject, depending on the species, age, weight and general condition of the subject, the severity of the disorder being treated, the mode of administration and the like. Thus, it is not possible to specify an exact amount for every composition for every use. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991).

In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a. Pharmaceutically Acceptable Carriers

The compositions can be used therapeutically in combination with a pharmaceutically acceptable carrier. By "pharmaceutically acceptable" is meant a material that is not biologically or otherwise undesirable, i.e., the material can be administered to a subject along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers can be more preferable depending upon for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like. The compositions can also include fatty acids, surfactants, or enteric material, alone or in combination. The compositions can also be mixed in liquid phase and lyophilized.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration, which can be referred to as oral dosage forms or a composition, include powders or granules, suspensions or solutions in water or non-aqueous media, capsules, sachets, or tablets. Thickeners, flavorings, diluents, emulsifiers, dispersing aids or binders may be desirable.

Pulmonary delivery of pharmaceutical compositions intended for systemic administration to patients can involve the deposition of a therapeutically active substance from a reservoir containing that active ingredient to an area of the patient's lungs capable transferring that substance, either actively or passively, to the patient's blood. The deposition is best accomplished by propelling a preparation comprised of an aqueous aerosol or solid particles containing the active ingredient into the lungs of the patient.

Particle size is an important consideration in achieving particle deposition in the distal lung regions. Porush et al., reported that to reach the alveoli, small particles should be 0.5 μm to 7 μm in diameter [(1960) Amer. Pharm. Assoc. Sci. Ed., vol. 49, p. 70]. Later, the preferred particle size for such deposition was reported to be less than 5 μm in diameter [Newman et al., (1983) Thorax, vol. 38, p. 881]. Along these lines, Utsumi et al. (PCT Patent Application No. WO 91/16038) disclosed the preparation of an aerosol composition comprised of solid, micronized human interferon or interleukin for pulmonary administration. In their preparation, the particles ranged from 0.5 μm to 10 μm in median diameter.

Devices capable of depositing aerosolized compositions comprising an EPIP formulation in the alveoli of a patient include nebulizers, metered dose inhalers, and powder inhalers. Other devices suitable for directing pulmonary administration are also known in the art. All such devices require the use of formulations suitable for the dispensing of a composition comprising an EPIP in an aerosol. Such aerosols can be comprised of either solutions (both aqueous and non-aqueous) or solid particles. Nebulizers are useful in producing aerosols from solutions, while metered dose inhalers, dry powder inhalers, etc. are effective in generating small particle aerosols. Typically, each formulation is specific to the type of device employed and can involve the use of an appropriate propellant material, in addition to the usual diluents, adjuvants and/or carriers useful in EPO therapy. As used herein, a "diluent" is any substance used to dilute the composition. As used herein, an "adjuvant" is any compound, composition substance, or structure that, when combined or used with a compound or composition, potentiates or enhances an effect of the composition.

b. Nebulizer Formulation

Formulations suitable for use with a nebulizer, either jet or ultrasonic, will typically comprise the composition dissolved in water. The formulation can also include a buffer and a simple sugar (e.g., for protein stabilization and regulation of osmotic pressure), and/or human serum albumin ranging in concentration from 0.1 to 10 mg/ml. Examples of buffers which can be used are sodium acetate, citrate and glycine. Preferably, the buffer will have a composition and molarity suitable to adjust the solution to a pH in the range of 5 to 7. Generally, buffer molarities of from 2 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation can also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for use with the disclosed compositions and methods is polyoxyethylene sorbitan monooleate.

Two specific examples of commercially available nebulizers suitable for the practice of the disclosed methods and for use with the disclosed compositions are the Ultravent nebulizer, manufactured by Mallinckrodt, Inc., St. Louis, Mo., and the Acorn II nebulizer, manufactured by Marquest Medical Products, Englewood, Colo.

c. Metered Dose Inhaler Formulation

Formulations for use with a metered dose inhaler device will generally comprise a finely divided powder. This powder can be produced by lyophilizing and then milling a liquid formulation and can also contain a stabilizer such as human serum albumin (HSA). Typically, more than 0.5% (w/w) HSA is added. Additionally, one or more sugars or sugar alcohols can be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the composition present. Such formulations are then lyophilized and milled to the desired particle size.

The properly sized particles are then suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant. This mixture is then loaded into the delivery device. An example of a commercially available metered dose inhaler suitable for use in the disclosed methods and with the disclosed compositions is the Ventolin metered dose inhaler, manufactured by Glaxo Inc., Research Triangle Park, N.C.

d. Powder Inhaler Formulation

Such formulations will comprise a finely divided dry powder containing the composition and can also include a bulking agent, such as lactose, sorbitol, sucrose, or mannitol in amounts which facilitate dispersal of the powder from the device, e.g., 50% to 90% by weight of the formulation. The composition should most advantageously be prepared in particulate form with an average particle size of less than about 10 µm (or micrometers), most preferably 1 to 5 µm, for most effective delivery to the distal lung.

An example of a powder inhaler suitable for use in accordance with the teachings herein is the Spinhaler powder inhaler, manufactured by Fisons Corp., Bedford, Mass.

The preservatives useful in the disclosed compositions are those preservatives compatible with erythropoietin and/or EPIPs so that the compositions are stable. Particular preservatives contemplated for use include benzyl alcohol, parabens, phenol, phenol derivatives, benzalkonium chloride and mixtures thereof. Depending on the particular preservative utilized, the amount of preservative could vary. In a preferred embodiment, benzyl alcohol is used in the amount of 0.6-2.0%, and most preferably, about 1%. At this concentration, benzyl alcohol provides the preservative and the local anesthetic capacities without unduly affecting the stability of the erythropoietin.

Among the parabens, the ones preferred for use in the disclosed compositions are methyl paraben, propyl paraben, and butyl paraben. The parabens can be used as a preservative singly or, in a most preferred embodiment, as a mixture of methyl and propyl paraben. The total content of parabens is preferably within the range 0.05-0.3%, more preferably with an amount of about 0.2% being most preferred. A most preferred paraben preservative is about 0.15-0.20% methyl paraben in combination with about 0.01-0.03% propyl paraben. Among the examples shown below is a combination of 0.18% methyl paraben with 0.02% propyl paraben. The use of a mixture of parabens and 0.5% benzyl alcohol as a preservative is also illustrated in the examples.

Concerning the use of phenol as a preservative, it can be used in amounts ranging from 0.2% to 0.5% with 0.3% being preferred. Other derivatives of phenol, in addition to the ones mentioned above, also can be used as preservatives. As examples of such derivatives, metacresol (m-cresol) and chlorocresol are used in compositions shown below, but the accelerated stability data with these compounds showed more rapid decay of the rEPO than was observed with the other preservatives mentioned above.

The disclosed compositions preferably include a buffering agent to maintain the pH of the solution within a desired range. Preferred agents include various salt, acidic, or basic forms of the following anions: citrate, phosphate, tartrate, succinate, adipate, maleate, lactate, acetate, bicarbonate, and carbonate. Representative salts of these buffers which can be used are the sodium and potassium forms, as long as the salt and the amount are physiologically compatible with the composition. Mixtures of these buffering agents can also be used. Among these agents, citrate and phosphate buffers are the most preferred.

The amount of buffering agent useful in the pharmaceutical compositions depends largely on the particular buffer used and the pH of the solution. For example, citrate is a more efficient buffer at pH 6 than at pH 7 so less citrate can be used in a solution at pH 6 than at pH 7. The preferred pH range for She solutions is 5-8 with 6-7 being more preferred, and a pH of about 6 being most preferred. Over these pH values, the amount of buffers will generally range from about 1 mM to about 30 mM. In a preferred embodiment, the amount of citrate buffer ranges from 1 mM to about 20 mM, and is preferably about 2-5 mM for a pH of about 6.

The disclosed compositions can further include an isotonicity-adjusting agent to render the solution isotonic and more compatible for injection. The preferred agents include sodium chloride, glycerol, mannitol, sucrose, sorbitol and mixtures thereof. The most preferred agent is sodium chloride.

The amount of isotonicity adjusting agent needed to render the solution isotonic varies with the particular agent but generally falls within the range of 0.1-10%.

The disclosed compositions can further include an anti-adsorbent which acts to reduce the loss of the composition by adsorption to the walls of the container and to other surfaces the product will contact, such as syringes and needles. Various surfactants and protein compounds such as albumin or gelatin can be used. The preferred anti-adsorbents are human serum albumin (HSA) and gelatin. These anti-adsorbents should be used in an amount sufficient to reduce the adsorption of the composition to surfaces thereby increasing the stability in solution without otherwise negatively affecting stability of erythropoietin and EPIP, e.g., causing aggregation or decomposition. A preferred amount of HSA is about 0.25%.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

e. Therapeutic Uses

Effective dosages and schedules for administering the compositions can be determined empirically, and making such determinations is within the skill in the art. The dosage ranges for the administration of the compositions are those large enough to produce the desired effect in which the symptoms or disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. For example, guidance in selecting appropriate doses for erythropoietin can be found in the literature on therapeutic uses of erythropoietin (Bamias et al., Oncology 2003; 64(2):102-10; Cody et al., Cochrane Database Syst Rev 2002; (4):CD003895). Dosage levels of the order of between about 1 EPO unit/kg and about 5,000 EPO units/kg body weight are useful for all methods of use disclosed herein. The dosage level can also be between about 50 EPO unit/kg and 300 unit/kg. The dosage level can also be between about 75 unit/kg and 250 unit/kg.

Guidance in selecting appropriate doses for EPIP derivatives can be found in the literature on therapeutic uses of EPIP derivatives. (See, for example, U.S. Pat. No. 4,526,888.) A typical daily dosage of the EPIP used alone can range from about 1 mg/kg to up to 600 mg/kg of body weight or more per day, or from 50 mg/kg to 500 mg/kg per day, or from 200 mg/kg to 400 mg/kg or from 150 to 300 mg/kg per day, depending on the factors mentioned above. The dosage can be administered once, or from 1-30 days, or from 1-10 days, or from 14 days.

Following administration of a disclosed composition, such as EPIP, for treating, inhibiting, or preventing anemia for example, the efficacy of the therapeutic EPIP can be assessed in various ways well known to the skilled practitioner. For instance, one of ordinary skill in the art will understand that a composition, such as EPIP, disclosed herein is efficacious in treating or inhibiting anemia, for example, in a subject by observing that the composition stimulates erythropoiesis and thereby improves the anemic condition.

The effectiveness of treatment using the disclosed compositions can be determined by assays which are known in the art. The erythropoietin immunoassay, for example, has proven to be useful in the detection of erythropoietin in a subject because the plasma clearance of erythropoietin is independent of its plasma concentration, is very slow relative to that of other hematopoietic growth factors and is not at all influenced by the size of the erythroid progenitor cell pool. Importantly, erythropoietin is biochemically unique and bears little homology to any other circulating protein. Erythropoietin production on a constitutive basis is uninfluenced by either age or gender and for a given individual, the circulating erythropoietin level is constant over time just as that individual's red cell mass is constant. The range of normal for circulating erythropoietin varies from 1 to 100 mU/ml, or from 2 to 50 mU/ml or from 4 to 26 mU/ml.

Other useful assays, devices, and systems in determining the effectiveness of the EPIP/erythropoietin treatment include the use of a red blood cell indices device, red blood cell enzyme assay, a hematocrit measuring device, an electrophoretic hemoglobin analysis system, red blood cell counters, and reticulocyte counters, for example. Erythropoietin production can be determined using, for example, radio-immunoassay (RIA), Western Blot Analysis, Northern hybridization analysis, immunocytochemistry, enzyme-linked immunosorbent assay (ELISA), enzyme-immunoassay (EIA), or in situ hybridization.

The administration of the composition comprising an EPIP can result in the red blood cell level being between 1000 and 10,000 erythrocytes per μl of blood. The red blood cell level can also be between 4000 and 7000 erythrocytes per μl of blood. The red blood cell level can also be between 5000 and 6000 erythrocytes per μl of blood. The red blood cell level can also be at or above 1000, 2000, 3000, 4000, 5000, 6000, 7000, 8000, 9000, or 10,000 erythrocytes per μl of blood.

The compositions that cause an increase in erythropoiesis, or stimulate the proliferation of PTFBLC disclosed herein can be administered prophylactically to patients or subjects who are at risk for erythropoietin-related disorders, such as those mentioned above.

Other molecules that allow for the measurement of increase in erythropoietin production, or increase in proliferation of fibroblast cells, or increase in erythropoiesis, for example, which do not have a specific pharmaceutical function, but can be used for tracking changes within cells, can be used as tools to study the function of interstitial cells.

The disclosed compositions and methods can also be used for example as tools to isolate and test new drug candidates for a variety of diseases and disorders associated with erythropoiesis. For example, the disclosed compositions and methods can be used to assess the effectiveness and mechanisms of other compositions to stimulate the proliferation of PTFBLC or erythropoietin or both in the kidney or by cells in vitro or ex vivo. In other words, all work whereby the disclosed compositions can be utilized as "tools" to study other erythropoietin producing compounds or approaches.

f. EPIP/Erythropoietin Delivery In Vivo

In the methods described above which include the administration and uptake of EPIPs and/or erythropoietin into the cells of a subject, the disclosed compositions can be in different forms, as would be well understood by one of ordinary skill in the art. Delivery of the EPIP to cells can be via a variety of mechanisms. As one example, delivery can be the cause of a non-lethal lysosomal storage condition in proximal tubular cells associated with a proliferation of PTFBLC, which in turn lead to an increase in the production of erythropoietin by the cells. Delivery can also be achieved according to procedures standard in the art.

Various means of administration were disclosed above. Parenteral administration of the EPIP, erythropoietin, or both, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

g. In Vitro Delivery Systems

The disclosed compositions can be delivered to the target cells in a variety of ways. For example, the compositions can be delivered through electroporation. Furthermore, application can occur simply by treating the solution of the cells with an appropriate concentration of the composition. The delivery mechanism chosen will depend in part on the type of cell targeted.

The erythropoietin can be harvested from the stimulated PTFBLC directly, or the newly proliferated PTFBLC can be reintroduced into the subject. One example of collecting erythropoietin in vitro is by contacting cells in culture with an EPIP, thereby stimulating the production of erythropoietin, clarifying the medium of cell debris to yield clarified EPO-containing medium, subjecting the EPO-containing medium to ion exchange chromatography to yield partially purified EPO, subjecting the partially purified EPO to reverse phase HPLC in an organic solvent to yield pure EPO in the organic solvent, and removing the organic solvent by ion exchange chromatography.

The compositions can comprise, in addition to the disclosed molecules, such as EPIPs and erythropoietin, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, or where the diffusion of the compound or delivery of the compound from the microcapsule is designed for a specific rate or dosage After stimulation of the PTFBLC, the cells themselves can be reinfused in the subject. In one example, bone marrow cells are isolated from peripheral blood samples via standard techniques (U.S. Pat. Nos. 4,987,121, 5,104,653; hereby incorporated by reference in their entirety). The bone marrow cells are seeded in culture dishes in appropriate medium (Royet et al., U.S. Pat. No. 5,482,924). An adherent cell monolayer is formed. The non-adherent cells are removed and fresh bone marrow is re-seeded in the presence of erythropoietin (EPO) and between about 0.1 ng/ml and about 10 mg/ml of EPIP. The cells are expanded for a period of between 1 and 21 days with subsequent medium changes as required. Prior to reinfusion into the subject the cells are examined microscopically to verify the absence of contamination. The cells are rinsed to remove all traces of culture fluid, resuspended in an appropriate medium and then pelleted and rinsed several times. After the final rinse, the cells are resuspended in an appropriate medium and reinfused into a subject. Erythropoiesis is monitored by red cell count or hemoglobin concentration with time (Yu et al., U.S. Pat. No. 5,032,507; herein incorporated by reference in its entirety), or one of the other methods of monitoring discussed above Also disclosed are methods of identifying signal molecules associated with a proliferation of erythropoietin producing PTFBLC. In some forms, the disclosed method can involve administering one or more of the disclosed compositions to a subject, harvesting proximal tubular cells from the subject, and identifying signal molecules which are responsive to the composition. In one embodiment, the identification of signal molecules can involve isolating the signal molecules, and monitoring them by, for example, Western blotting, Northern blotting, EIA, ELISA, or RIA. The signal molecules can also be detected by, for example, gene array technology and multiplex cytokine protein assay or by proteomics. Once identified and isolated, the signal molecules can be used to develop drugs or molecules that modulate erythropoietin production. In another embodiment, molecules which are structurally similar to or derivatives of the signal molecule can be developed that have the ability to directly stimulate erythropoietin.

3. Methods for Making Erythropoietin

Administration of EPIPs to cells causes a lysosomal storage condition in proximal tubular cells associated with a proliferation of PTFBLC. The amount of erythropoietin produced in 24 hours from a standard culture of fibroblast cells can be 10 U-10,000 U. The amount can also be between 100 U and 1000 U.

The compositions disclosed herein and the compositions necessary to perform the disclosed methods can be made using any method known to those of skill in the art for that particular reagent or compound unless otherwise specifically noted.

Disclosed are methods of producing erythropoietin. In some forms of the methods, the disclosed compositions are used to stimulate the production of erythropoietin. The erythropoietin produced can be used where produced, as in the case of the stimulation of erythropoietin in a subject or the erythropoietin produced can be harvested, purified or isolated for use in another context. Some aspects of production of erythropoietin are disclosed elsewhere herein.

Also disclosed are compositions and methods, which can be used to isolate and identify molecules that are capable of stimulating erythropoietin production. It is disclosed herein that a key aspect in producing erythropoietin is the stimulation of the proliferation of fibroblast cells. Thus, molecules that are capable of stimulating either proliferation of fibroblast cells, or the production of erythropoietin from said cells, are molecules which are capable of increasing erythropoietin production. Therefore, disclosed are methods in which erythropoietin is produced, and harvested accordingly.

It is understood that these methods can be used with a variety of techniques known to those of skill in the art. The disclosed methods can also use various compositions as controls. For example, the effect poly-D-glutamic acid has can be used as a standard and molecules being tested or screened can be compared to the poly-D-glutamic acid for their effect, either directly or indirectly by referring to the data herein. Cells which express erythropoietin can be used as discussed herein to isolate and identify compositions that affect fibroblast proliferation, production of erythropoietin from native fibroblast cells, and/or delivery of erythropoietin to the appropriate location.

As disclosed above, the effectiveness of the EPIP and/or erythropoietin treatment can be determined by assays which are known in the art. The erythropoietin immunoassay is one example. Other useful assays, devices, anti systems in determining the effectiveness of the EPIP/erythropoietin treatment include the use of a red cell indices device, red blood cell enzyme assay, a hematocrit measuring device, an electrophoretic hemoglobin analysis system, red blood cell counters, and reticulocyte counters, for example. Western Blot Analysis can also be used to determine erythropoietin production.

Accordingly, disclosed is a method of producing substantially pure erythropoietin, involving (a) contacting cells in culture with an EPIP, thereby stimulating the production of fibroblast cells, and in turn the production of erythropoietin, (b) clarifying the medium of cell debris to yield clarified EPO-containing medium, (c) subjecting the EPO-containing medium to ion exchange chromatography to yield partially purified EPO, (d) subjecting the partially purified EPO to reverse phase HPLC in an organic solvent to yield pure EPO in the organic solvent, and (e) removing the organic solvent.

In one embodiment, step (e) is carried but by ion exchange chromatography or by solvent evaporation or solvent removal by dialysis, followed by gel filtration.

In other embodiments, following step (b), the clarified EPO-containing medium is treated to inhibit proteolytic degradation of EPO during step (c), by removal of proteases in the clarified EPO-containing medium by fractionation on a dye column, or by the addition to the clarified EPO-containing medium of a protease inhibitor.

In one embodiment, about 20%, 30%, 40%, 50%, 60%, 70%, 80%, 90%, or 100% of cells are producing erythropoietin.

It is understood that the disclosed compositions can be made by a variety of methods, and the disclosed herein are compositions produced by those methods having the properties disclosed herein.

C. Vectors and Expression Sequences

It is understood that in certain embodiments the compositions as disclosed herein can be produced intracellularly, after transfection or transformation of a cell with an appropriate expression vector for the compositions. In this way, for example, cultured interstitial fibroblasts could produce poly D glutamic acid intracellularly. The disclosed vectors and delivery systems are examples of the types of systems that can be used.

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

As used herein, plasmid or viral vectors are agents that transport the gene into the cell without degradation and include a promoter yielding expression of the gene in the cells into Which it is delivered. In a preferred embodiment vectors are derived from either a virus or a retrovirus. Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

1. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology—1985, American Society for Microbiology, pp. 229-232, Washington, (1985), which is incorporated by reference herein. Examples of methods for using retroviral vectors for gene therapy are described in U.S. Pat. Nos. 4,868, 116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new, retroviral particles, by the machinery provided in cis by the helper cell. The genomes for the machinery are not packaged because they lack the necessary signals.

2. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A preferred viral vector is one based on an adenovirus which has had the E1 gene removed and these virons are generated in a cell line such as the human 293 cell line. In another preferred embodimnent both the E1 and E3 genes are removed from the adenovirus genome.

Another type of viral vector is based on an adeno-associated virus. (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

3. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3:1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will, use an enhancer from a eukaryotic cell virus. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

It is preferred that the promoter and/or enhancer region act as a constitutive Promoter and/or enhancer to maximize expression of the region of the transcription unit to be transcribed. It is further preferred that the promoter and/or enhancer region be active in all eukaryotic cell types. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

4. Markers

The viral vectors can include nucleic acid sequence encoding a marker product. This marker product is used to determine if the gene has been delivered to the cell and once delivered is being expressed. Preferred marker genes are the *E. Coli* lacZ gene which encodes β-galactosidase and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5:410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

D. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include reagents as well as cells, discussed in certain embodiments of the methods, as well as the buffers and enzymes required to perform assays, such as screening assays.

Specific Exemplary Embodiments

In some forms, the disclosed compositions comprise erythropoietin and an erythropoietin production inducing peptide (EPIP).

In some forms, the disclosed compositions comprise an EPIP.

In some forms, the disclosed compositions comprise cells, wherein the cells can be propagated in vitro and are capable upon growth in culture of producing erythropoietin when the cells are exposed to an EPIP.

In some forms, disclosed are compositions comprising cells and an EPIP.

In some forms, the disclosed method of treatment comprises administering erythropoietin to a subject, wherein the erythropoietin is produced by the method comprising contacting cells in culture with an EPIP and harvesting erythropoietin from these cells.

In some forms, the disclosed method of treatment involves administering erythropoietin and an EPIP to a subject.

In some forms, the disclosed method of treatment involves administering an EPIP to a subject.

In some forms, the disclosed method involves testing a substance for the ability to stimulate erythropoietin production, the method comprising contacting cells with the substance and monitoring the cells for the production of erythropoietin.

In some forms, the disclosed method involves the production of erythropoietin, the method comprising contacting cells or co-cultures with an EPIP and harvesting erythropoietin from these cells.

In some forms, the disclosed method involves the production of erythropoietin, comprising administering an EPIP to a mammal and harvesting erythropoietin producing cells from the mammal.

In some forms, the disclosed method involves the production of erythropoietin comprising administering an EPIP to a mammal and harvesting proximal tubular cells from the kidney.

In some forms, the disclosed method involves identifying signal molecules associated with a proliferation of erythropoietin producing cells, comprising treating a subject with a composition; identifying signal molecules which are responsive to the composition; and screening the signal molecules individually or in combination to identify those signal molecules associated with a proliferation or erythropoietin producing cells.

The composition can comprise a therapeutically effective amount of erythropoietin and EPIP. The composition can comprise a therapeutically effective amount of an EPIP. The composition can comprise erythropoietin in the form of recombinant erythropoietin. The composition can comprise EPIP comprising at least two residues having the formula I or II

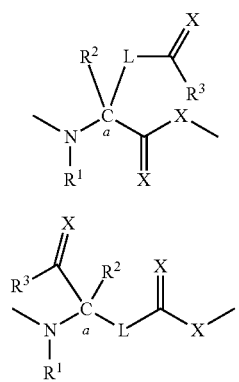

wherein each X is, independently oxygen or sulfur; L is not present or when L is present, L is oxygen, $NR^4$, or a substituted or unsubstituted methylene group, polyalkylene group, polyether group, polyamide group, polyester group, polyimino group, aryl group, or polythioether group; $R^1$, $R^2$, $R^3$ and $R^4$ are, independently, hydrogen, halide, alkyl, alkenyl, alkynyl, aryl, cycloalkyl, aralkyl, alkoxy, hydroxyalkyl, alkoxyalkyl, a keto group, an ester group, a carbonate group, an aldehyde group, or a carboxylic acid group; and the stereochemistry at carbon a is substantially R, substantially S, or a mixture thereof of R and S; wherein the residues having the formula I and II are neutral or ionic, wherein each residue can have the formula I, each of the residues can have the formula II, or the residues can be a mixture of formulas I and II.

Each X of the EPIP can be oxygen. $R^1$ and $R^2$ of the EPIP can be hydrogen. L of the EPIP can be polyalkylene group. $R^3$ of the EPIP can be hydroxyl, alkoxy, or OM, wherein M can be a cationic salt. Each X of the EPIP can be oxygen, $R^1$ and $R^2$ can be hydrogen, $R^3$ can be hydroxyl or OM, wherein M can be a cationic salt, L can be $CH_2CH_2$, and the stereochemistry at carbon a can be substantially R or substantially S. The residues of the EPIP can have the formula I. The EPIP can comprise only residues having the formula I, formula II, or a mixture thereof. The EPIP can comprise poly-D-glutamic acid or poly-L-glutamic acid or a mixture of both. The EPIP can be poly-D-glutamic acid. The EPIP can comprise at least two residues having a tethered carboxylic acid group, a tethered amide group, a tethered ester group or salt thereof. The tether can comprise a polyalkylene group, a polyether group, a polyamide group, a polyester group, a polyimino group, an aryl group, or a polythioether group. The tether can comprise a polyalkylene group.

The composition can comprise a pharmaceutically acceptable diluent, adjuvant or carrier. The preservative can comprise benzyl alcohol, a paraben and phenol, or a mixture thereof. The composition can comprise a buffering agent. The buffering agent can comprise citrate, phosphate, tartrate, succinate, adipate, maleate, lactate and acetate buffers, sodium bicarbonate, and sodium carbonate, or a mixture thereof.

The composition can comprise an isotonicity adjusting agent, wherein the isotonicity adjusting agent comprises sodium chloride, glycerol, mannitol, sorbitol, or a mixture thereof. The composition can comprise a pH adjusting agent that adjusts the pH of the solution within the range of 5-8. The composition can comprise human serum albumin. The composition can comprise an aqueous solution, a non-aqueous suspension, or a dry powder. The composition can be in oral dosage form. The oral dosage form can comprise fatty acid(s), surfactant(s), or enteric material, or a mixture thereof, wherein components are mixed in liquid phase and lyophilized. The composition can be in injectable form.

The EPIP can be poly-D-glutamic acid or poly-L-glutamic acid or a mixture of both the EPIP can be poly-D-glutamic acid. The cells can produce 100 U or more of erythropoietin per $10^6$ cells in 48 hours. The cells can produce 500 U or more of erythropoietin. The cells can produce 1000 U or more of erythropoietin. The poly-D-glutamic acid can be administered in the amount of about 50 mg/kg of body weight per day to 400 mg/kg of body weight per day.

The method of treatment can comprise treating anemia, Crohn's Disease, ulcerative colitis, acute renal disorder, chronic renal insufficiency, or end stage renal disease or any erythropoietin-responsive anemia. The method of treatment can result in angiogenesis in the kidney. The method of treatment can comprise treating organ or tissue transplantation subjects. The method of treatment can comprise enhancing wound healing. The method can comprise treating a subject. The subject can be a mammal. The subject can be a human. The erythropoietin and/or EPIP can be administered by intravenous or intramuscular or subcutaneous or intraperitoneal injection. The erythropoietin, EPIP, or erythropoietin and EPIP can be administered orally or rectally. A mechanical device can direct a stream of a therapeutically effective amount of poly-D-glutamic acid into the oral cavity of a mammal while the mammal is inhaling. The mechanical device can be selected from the group consisting of a nebulizer, a metered dose inhaler, and a powder inhaler. The administration of poly-D-glutamic acid can result in a red blood cell level of 5000 or more erythrocytes per μL of blood. The monitoring can be Western blot analysis, or SDS PAGE, immunocytochemistry or Northern hybridization or in situ hybridization or enzyme-linked immunosorbent assay (ELISA) of enzyme-immuno assay (EIA) or radioimnunoassay (RIA). The cells can produce between 100 U and 1000 U of erythropoietin. The EPIP can comprise poly-D-glutamic acid.

The erythropoietin can be harvested by steps comprising removing culture fluid from the cells; and isolating erythropoietin from the culture fluid. The erythropoietin can be isolated from the culture fluid by using HPLC. The erythropoietin can be not isolated from the cell culture. The cells can be mammalian cells. The cells can be proximal tubular cells. Co-cultures of proximal tubular cells can cause the proliferation of fibroblast cells. The cells can be kidney cells. At least 50% of the cells can produce erythropoietin. Erythropoietin can be produced by contacting cells in culture with an EPIP and harvesting erythropoietin from these cells. The composition can be EPIP. The EPIP can be poly-L-glutamic acid or poly-D-glutamic acid or a mixture of both.

The signal molecules can be monitored by Western blotting or Northern blotting or EIA or ELISA or RIA. The signal molecules can be detected by gene array technology. The signal molecules associated with a proliferation of erythropoietin can be used to identify mechanisms of erythropoietin production.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

1. Materials and Methods
   i. Animals

Sprague-Dawley rats of both sexes, weighing from 180 to 200 g, were used throughout the study. A few days before the experiment, rats were adapted to the housing conditions in a central animal facility (regular 12 hours light/dark cycles, free access to standard rat chow and tap water). In a first series of experiments designed for the conventional morphologic and histoautoradiographic examination, female rats received either saline (0.5 ml subcutaneously; controls, n=10) or poly-D-glutamic acid (250 mg/kg body wt/day in 0.5 ml saline, subcutaneously) for 1, 2, or 4 days (n=5 per group). For histoautoradiographic studies, some treated animals and controls were further injected with 300 µCi of [methyl-$^3$H]-thymidine intraperitoneally 1 hour before their deaths. In a second series of experiments focusing on ultrastructural cytochemistry of an indigenous lysosomal enzyme (arylsulfatase) or an exogenous tracer of the endocytic pathway (horseradish peroxidase), male and female rats were treated subcutaneously with poly-D-glutamic acid (250 mg/kg body wt, in 0.5 ml saline) either 3 hours (n=7) or 24 hours (n=4) before death. These rats also received intravenous injections of horseradish peroxidase (70 mg/kg body wt) 3 hours before death.

ii Conventional Morphologic and Histoautoradiographic Examinations

Animals were killed by decapitation 1 day after the last treatment with poly-D-glutamic acid or saline (controls), and their kidneys were quickly excised. One half of the right kidney was immersed in Boulin solution and processed for paraffin sections (approximately 5-µm thickness) destined for histopathologic and/or histoautoradiographic study. For histopathologic use, sections were stained with hematoxylin and eosin with or without periodic acid-Schiff reagent or with Giemsa stain. Histoautoradiographic studies were performed and the data were presented as described earlier (Kishore et al., 1992; Laurent et al., 1983). Briefly each section was examined along parallel straight lines, extending from the subcapsular to the juxtamedullary region. The number of total and labeled nuclei (S-phase cells) were counted, and the corresponding cell type was identified. For electron microscopic evaluation, small blocks (approximately 1 mm$^3$) of cortex were cut from the left kidney, immersed in ice-cold 2% glutaraldehyde buffered with 0.1 M Na cacodylate (pH 7.4), post-fixed in osmium tetroxide, dehydrated, and embedded in epoxy resins. Ultrathin plastic sections (approximately 50-nm thickness) were cut with a diamond knife, stained with uranyl acetate and lead citrate, and examined in a Zeiss EM 9 electron microscope (Carl Zeiss, Oberkochen, Germany) operating at 60 kv.

iii. Ultrastructural Cytochemistry

Rats were anesthetized with ether, and the kidneys were retrogradely perfused through the abdominal aorta. After flushing the kidneys with PBS for 3 minutes, they were fixed in situ with 1% glutaraldehyde in PBS for 3 or 10 minutes (for different grades of fixation), followed by perfusion with only PBS for 3 to 5 minutes. Kidneys were excised, and small blocks of cortical tissue were cut, embedded in molten agar (2% in PBS), chilled on ice, and sliced with a tissue chopper (100-µm nominal thickness). For peroxidase cytochemistry, slices were incubated in a medium containing diaminobenzidine and $H_2O_2$ (Graham and Karnvosky, 1966) and supplemented with 25 mM merthiolate (Courtoy, 1989) to prevent diffusion-relocation artifacts (Courtoy et al., 1983). For arylsulfatase cytochemistry, slices were first incubated in the presence of nitrocatechol sulfate and lead nitrate, then incubated in the presence of ammonium sulfide (Wall et al., 1980). After the cytochemical reaction, slices were rinsed in appropriate buffers and post-fixed in a mixture of 1% osmium tetroxide and 1% potassium ferrocyanide solution in distilled water (Karnovsky, 1971), dehydrated, and embedded in Epon or the mixture described Spurr (1969). Ultrathin sections were stained and examined in a Phillips EM 301 electron microscope (Eindhoven, the Netherlands) operating at 60 kv.

iv. Major Products

Poly-D-glutamic acid (mean molecular weight, approximately 20 kd, lots 84F-5013 and 104-50451) and horseradish peroxidase (type II) were from the Sigma Chemical Company. [Methyl-$^3$H]-thymidine (40 mCi/mmol) was from Amersham International (Buckinghamshire, United Kingdom). All other chemicals were of the highest available purity.

v. Statistical Analysis

Histoautoradiographic labeling indices were subjected to ANOVA, and the significance of the F value was determined. If the F value was significant (p<0.05), the variation among the means of different groups was considered significantly greater than expected by chance. In such cases, the differences among the means of groups were further tested by Tukey-Kramer multiple comparison test, and p values <0.05 were considered significant.

vi. Poly-D-Glutamic Acid

Poly-D-Glutamic (approx. molecular weight 20 kDa) can be purchased from Sigma Chemical Co., St. Louis, Mo.

vii. Analysis of Kidney Samples

Kidneys can be fixed for light and electron microscopy by standard methods. In situ hybridization and immunocytochemical studies can be performed by the standard methods. Primary antibodies to CD73 (5'-nucleotidase), EPO and other proteins can be purchased from Santa Cruz Biotechnology, San Diego, Calif. Secondary antibodies can be purchased either from Santa Cruz or Pierce Endogen. For in situ hybridization studies, DIG-labeled probes prepared and tested. EPO gene sequence is highly conserved between rat and mouse.

viii. Surgical Reduction of Kidney Mass in Rats

Rats can be anesthetized with sodium pentobarbital (50 mg/kg, ip). After cleaning the skin, through a right flank incision, the right kidney can be surgically removed through a right flank incision after ligating the renal blood vessels. The left kidney can be exposed through a left flank incision, and leaving the middle branch intact, the upper and lower branches of the renal artery can be isolated and ligated, and the wound closed after replacing the left kidney in place.

Sham operated rats are handled identically without ligatures and resections. Although the infarction model is characterized by hypertensive renal injury, it is preferable to the surgical resection of renal mass, because of the early development of the typical changes characteristic of human chronic renal failure, such as proteinuria and glomerulosclerosis. Post-operative analgesa (Buprenorphin 0.02 to 0.5 mg, sc, every 12 hours for 2 days) can be administered to relieve pain. Rats are allowed to recover and their kidney function (BUN) and hematocrit can be monitored for 3 to 8 weeks, during which time the rats can be injected, (sc or ip) with in vitro cultured PTFBLC cells.

ix. Detection of Apoptosis and Cell Proliferation in Kidney Tissue

Apoptotic cell death can be detected and quantified by staining for fragmented DNA by TaT-mediated deoxyuridine triphosphate nick-end labeling (TUNEL) assay using commercially available kit (Intergen Company, Purchase, N.Y.). For the detection and quantification of proliferating cells the animals can be treated with BrdU. Prior to euthanasia the kidney samples can be labeled using commercially available BrdU staining kit (Zymed Laboratories, Inc., San Francisco, Calif.).

x. Cell Culture Experiments

Culturing of proximal tubular cells, epithelial cells, and renal fibroblasts and co-cultures of epithelial cells and fibroblasts can be carried out according to the techniques established in the art.

xi. Detection of Apoptosis and Cell Proliferation in Cell Cultures

Apoptotic cell death in cultured cells can be assayed by TUNEL assay (Intergen) and quantitated by FACS. Cell proliferation in cultured cells can be assayed by MTT (3-(4,5-dimethylthiazol-2-yl)-2-5-diphenyltetrazoliume bromide) or Thiazoyl blue assay. There is an excellent linear correlation ($r=0.99$) between the cell counting methods and the MTT assay.

xii. Detection of Cytokines in Culture Media

Commercially available multi-cytokine profiling kits can be used.

xiii. EPO Assay

EPO concentration in the culture media and serum an kidney tissues can be assayed by ELISA using a commercial kit (ALPCO Diagnostics, Windham, N.H.).

B. Example 2

1. Identification of Cells as Erythropoietin Producing Fibroblasts

Male Sprague-Dawley rats were divided randomly into two groups. One group was injected with 250 mg of poly-D-glutamic acid per kg body weight per day subcutaneously for 4 days. The poly-D-glutamic acid (13,000 or 26,000 kDa; Sigma Chemical Co.) was dissolved in physiological saline (0.9% sodium chloride). Another group received comparable volumes or normal saline injections subcutaneously for 4 days. All rats were euthanized on day 5 by pentobarbital overdose. Kidneys were harvested quickly from the dead rats and one half of one kidney was immersed in 10% neutral buffered formalin. The formalin fixed kidneys were dehydrated and embedded in paraffin. Sections of 3 to 4 µM thickness were cut on a microtome. Sections were deparaffinized by standard methods and processed for immunohistochemical staining for CD73 (5'-nucleotidase) and erythropoietin (Epo) as described below.

Deparaffinized kidney sections were treated for exposure of antigenic sites and blocked for non-specific binding by standard methods. Following this they were incubated with specific antibodies to CD 73 (marker for resident fibroblasts in kidney) or Epo. Goat polyclonal antibodies to CD73 and Epo were purchased from the Santa Cruz Biotechnology, Santa Cruz, Calif. They were used at a dilution of 1:50. After washing off the unreacted primary antibodies, the sections were incubated with biotinylated anti-goat polyclonal antibody (secondary antibody), followed by incubation with avidin-biotin complex. Sections were then washed and incubated with substrate to visualize the antigen-antibody reactions. Positive labeling in the sections is seen as brownish color. Sections were then counterstained with hematoxylin to visualize the rest of the kidney structures that do not show positive immunohistochemical reaction. Sections were examined under a Reichert Microscope and digital images were captured using a Nikon Coolpix 0995 Digital Camera.

C. Example 3

1. Purification of Erythropoietin from a Cell Culture i. Clarification Concentration and Dialysis of Culture Medium Containing EPO 11.75 liters of CES9dog conditioned serum-free media, harvested from 10 liter spinner flasks and containing approximately 700 units of EPO per ml, were made 0.01% in Tween 80, and then clarified of cell debris and microcarriers by passage through a 0.5 um Pall Profile.™ filter cartridge at a flow rate of 2.5 L/minute. The pressure of the cartridge did not exceed 20 psi. The clarified media were then concentrated 10-fold and flow dialyzed into 50 mM Na Acetate, pH5.0 containing 15 mM NaCl, and 0.01% Tween 80 to a final conductivity of 6.90 mS/cm$^2$. This was accomplished with a tangential flow system: an Amicon Spiral Ultrafiltration S10Y10 cartridge having a YM 10,000 MW cutoff membrane was used at a retention flow rate of 1.5-2 L/minute, a breakthrough flow rate of 0.4-0.8 L/minute, and a back pressure maintained at 25-30 psi. The volume of the final concentrate was 970 ml, its pH was 5.0, and its conductivity 6.90 mS/cm cm$^2$. EPO recovery through these steps is greater than 90%.

ii. Ion Exchange Chromatography

A screen of ion exchange resins demonstrated that relatively high ionic strength resins are best suited for the purification of EPO. In this particular example, an S-Sepharose Fast Flow column from Pharmacia was used. A 2.5 cm×12.5 cm (60 ml) column was equilibrated at 4° C. with 50 mM Na Acetate, pH 5.0, containing 15 mM NaCl, and having a conductivity of 6.90 mS/cm$^2$. The absorbance of the column effluent was monitored at 280 nm with an in-line detector (LKB). The column was loaded with 960 ml of the concentrated media at a flow rate of 5 ml/minute (61.6 cm/hour) and the column was washed with equilibration buffer until the absorbance returned to baseline (approximately 2 column volumes). The column was eluted with a 300 ml linear salt gradient of 0.015 M to 0.4 M NaCl in 50 mM Na Acetate, pH5.0. Fractions (6 ml) were collected into tubes containing 0.15 ml of 2M Tris-HCl, pH8.8. This adjusted the pH of the effluent to approximately 8.0 and gave a final Tris concentration of 0.05 M. Finally, the column was washed with 0.05 M Tris-HCl, pH9.0, containing 2 M NaCl. EPO-containing fractions were pooled.

The S-Sepharose Fast Flow column gave an approximately 7-fold purification and a recovery of about 60%. Losses at this step are due to proteases present in the conditioned medium which are active at p5.0 (which is the optimal pH for EPO purification with this resin). (As is described below, losses at this step can be minimized by the use of immobilized dyes or protease inhibitors.)

iii. Preparative Reverse Phase HPLC

HPLC was carried out with a Waters high pressure liquid chromatography system consisting of a model 6000A solvent delivery system and a model 660 solvent programmer. A 2.2 cm.times.25 cm preparative $C_8$ column (Amicon 10 um particle size, 100 A pore size) was equilibrated at room temperature with 10 mM $NaPO_4$, pH6.0 buffer. (A column of different carbon length, e.g., $C_4$-$C_{18}$, can also be used, but are less preferred.). The pooled S-Sepharose sample was prefiltered through a 0.45 um Gelman Acrodisk filter and loaded onto the column by repeated injections using a 2 ml sample loop. The column was run at 6 ml/minute (71.0 cm/h) and the absorbance of the effluent was monitored at 280 m. Following loading the sample, the column was washed with 10 mM $NaPO_4$, pH6.0, until the absorbance returned to baseline. The column was eluted with a 2.5 h linear 0% to 40% n-propanol gradient (in 10 mM $NaPO_4$, pH6). One minute fractions (6 ml) were collected.

Figure 8:
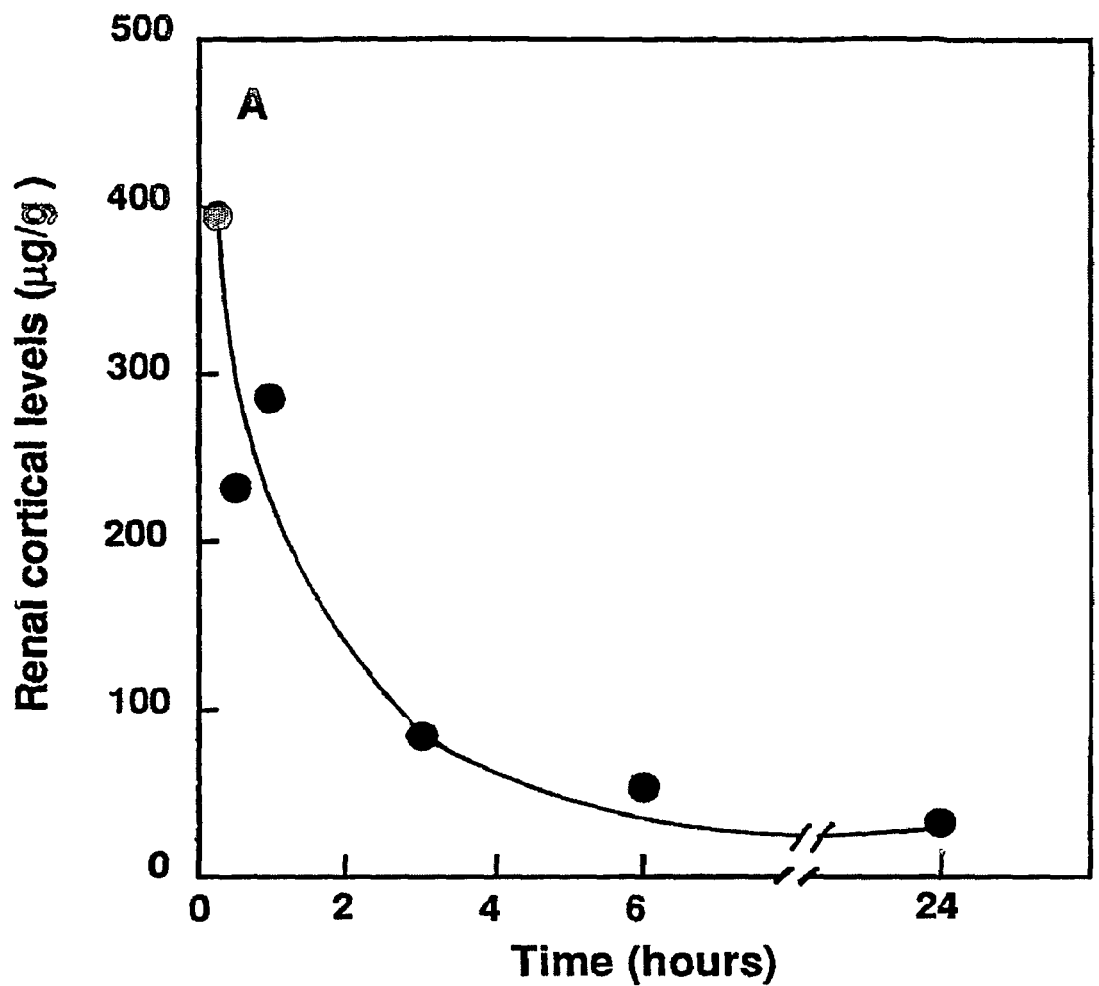
FIG. 8 shows renal cortical content of $^{14}$C-poly-D-glutamic acid. Time course of 14C-poly-D-glutamic acid association with kidney cortices after a single subcutaneous injection of 150 mg/kg body weight. Assuming flushing is exhaustive, a major fraction of the poly-D-glutamic acid taken up by kidney cortex at early stages could be released into the luminal fluid. Results are given as means for two animals.

Several small peaks of material absorbing at 280 nm were eluted between 60 minutes and 95 minutes of the gradient and a single, sharp peak eluted between 100 minutes to 110 minutes (FIG. 8). The elution peaks were analyzed by SDS PAGE. The EPO containing fractions coincided with the large peak at 100 minutes to 107 minutes (approximately 25% Propanol). A laser densitometer scan of the coomassie stained SDS gel indicated that the EPO was greater than 99% pure at this stage. In this example, the $C_8$ step gave a 2-fold purification.

The recovery of immunological and of in vitro biological activity at this step was high (83%), indicating that n-propanol had no adverse effects on the in vitro biological activity.

iv. Gel Filtration Chromatography

To ensure complete removal of the organic solvent and to elute the purified EPO in a desired physiologically compatible buffer, the $C_8$-purified material can be further fractionated by gel filtration chromatography. If the gel filtration resin is not compatible with high concentrations of organic solvents, a flow-dialysis step must be used prior to gel filtration in order to remove the majority of the organic solvent. If the resin matrix of the last column is resistant to the organic solvent used, the pooled fractions from the RP-HPLC step can be passed directly over this column under conditions where the protein binds to the resin and the organic solvent flows through. The organic solvent can then be washed out extensively with an aqueous buffer and the protein can finally be eluted from the column.

The elution pool from the $C_8$ column was made 1% mannitol and 0.5M NaCl by the addition of solid material, and then introduced into an Amicon stir cell having a YM10 (10,000 M.W. cutoff) ultrafiltration membrane. The volume was reduced approximately ten fold and then restored to the original volume with 15 mM $NaPO_4$ pH7.2, containing 0.5M NaCl and 1% mannitol. The process was repeated twice and the dialyzed pool was concentrated to a final volume of 17.5 ml. Analysis of this process for total protein using the Lowry method showed greater than 98% recovery. Fourteen ml of the dialyzed material was then fractionated by gel filtration chromatography.

A 2.5 cm×98 cm (481 ml) column of GC200 Cellufine filtration resin (Amicon) was equilibrated at 4 degrees C. with 15 mM $NaPO_4$, pH7.2 buffer containing 0.5M NaCl and 1% mannitol at a flow rate of 0.8 ml/minute (9.8 cm/hour). The 14 ml sample was loaded, the column effluent was monitored at 280 nm, and 6 ml fractions were collected. A single, symmetrical peak was eluted and SDS PAGE confirmed the peak to be EPO. No further purification of EPO was achieved at this step and the recovery was 89%.

EPO produced by the above purification method was shown to be greater than 99% pure as judged by SDS-PAGE and to have high potency in in vitro and in vivo biological assays. The overall EPO yield in this example was 41%. The yield can range from 15% to 95%. The yield can also range from 30% to 50%.

The addition of a dye column to step 1 gives some additional purification and, more importantly, removes contaminating proteases from EPO and consequently allows higher EPO recoveries at the S-Sepharose Fast Flow step. The clarified media was loaded on a Blue Trisacryl-M column (Pharmacia) equilibrated with 10 mM $NaPO_4$ pH6.0, 150 mM NaCl and eluted with a linear salt gradient of 0.15 to 2.5 M NaCl in 10 mM $NaPO_4$ pH6.0 and then flow-dialyzed into 50 mM Na Acetate, pH5.0 containing 15 mM NaCl. The recovery of EPO from the Blue Trisacryl column was almost complete and the recovery on the following S-Sepharose Fast Flow column was 86% compared to 60% in example 1. EPO containing 10× concentrated medium or partially purified step 2 material has been shown to degrade rapidly (t1/2 approx. 4 h) when incubated at 37.degree. C. under mildly acidic conditions at pH5.0. This degradation seems to be caused by proteases that are active at PH5.0. The improved yields in step 2 as illustrated in this example can be attributed to the separation of proteases from the EPO protein by the Blue Trisacryl column. (Other commercially available dyes can also be used.)

Figure 9:
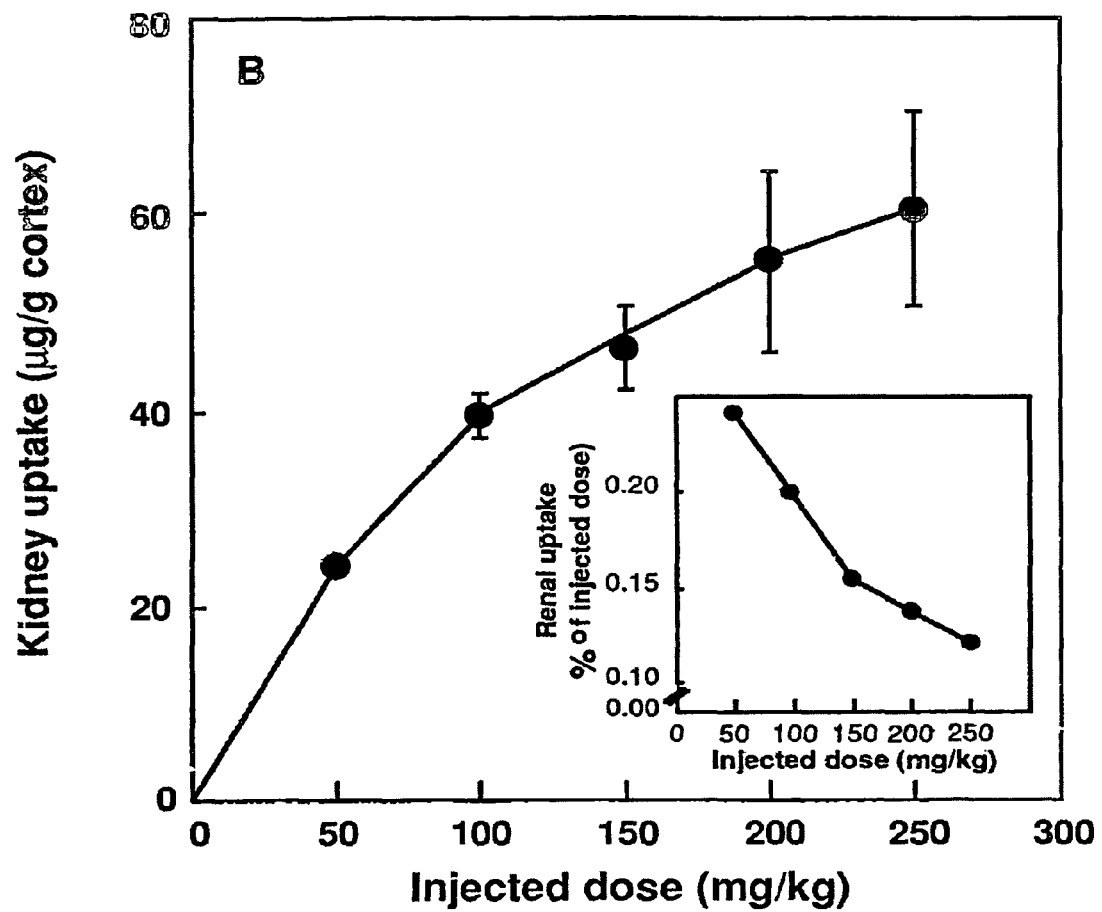
FIG. 9 shows renal cortical content of $^{14}$C-poly-D-glutamic acid as a function of dose at 18 hours after a single subcutaneous injection. Each value is the mean+/−SD for 3 rats. In accordance with saturation kinetics, an inverse relation can be seen between the injected dose and the fractional uptake.
Figure 10:
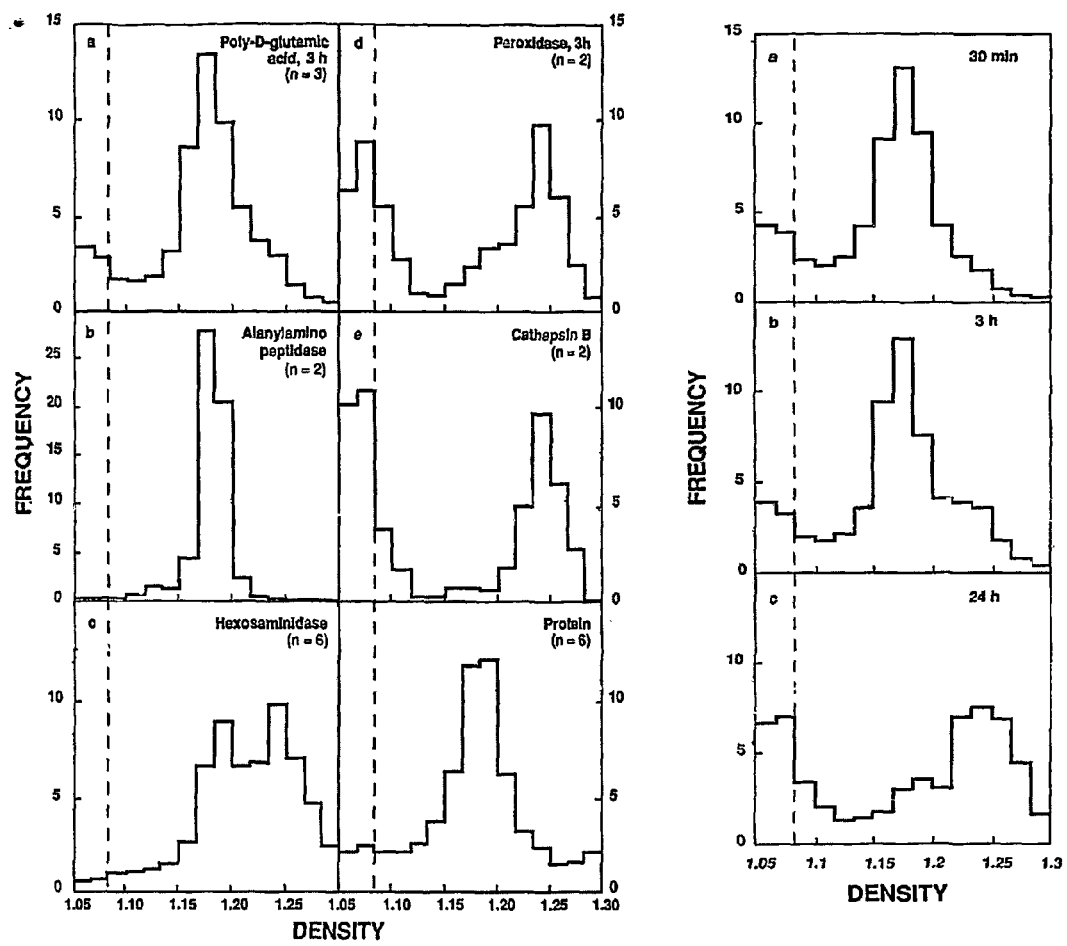
FIG. 10 shows distribution of $^{14}$C-poly-D-glutamic acid and of peroxidase in postnuclear particles after isopynic centrifugation in sucrose density gradients: comparison with marker enzymes. Distribution of $^{14}$C radioactivity (a) and peroxidase activity (d) in postnuclear particles of renal cortical homgenates obtained from rats injected with 150 mg/kg body weight of $^{14}$C-poly-D-glutamic acid subcutaneously and 70 mg/kg body weight of horseradish peroxidase intravenously 3 hours before their deaths. Postnuclear particles were equilibrated in linear sucrose density gradients. Distributions are the average of 2 to 6 gradients.
Figure 11:
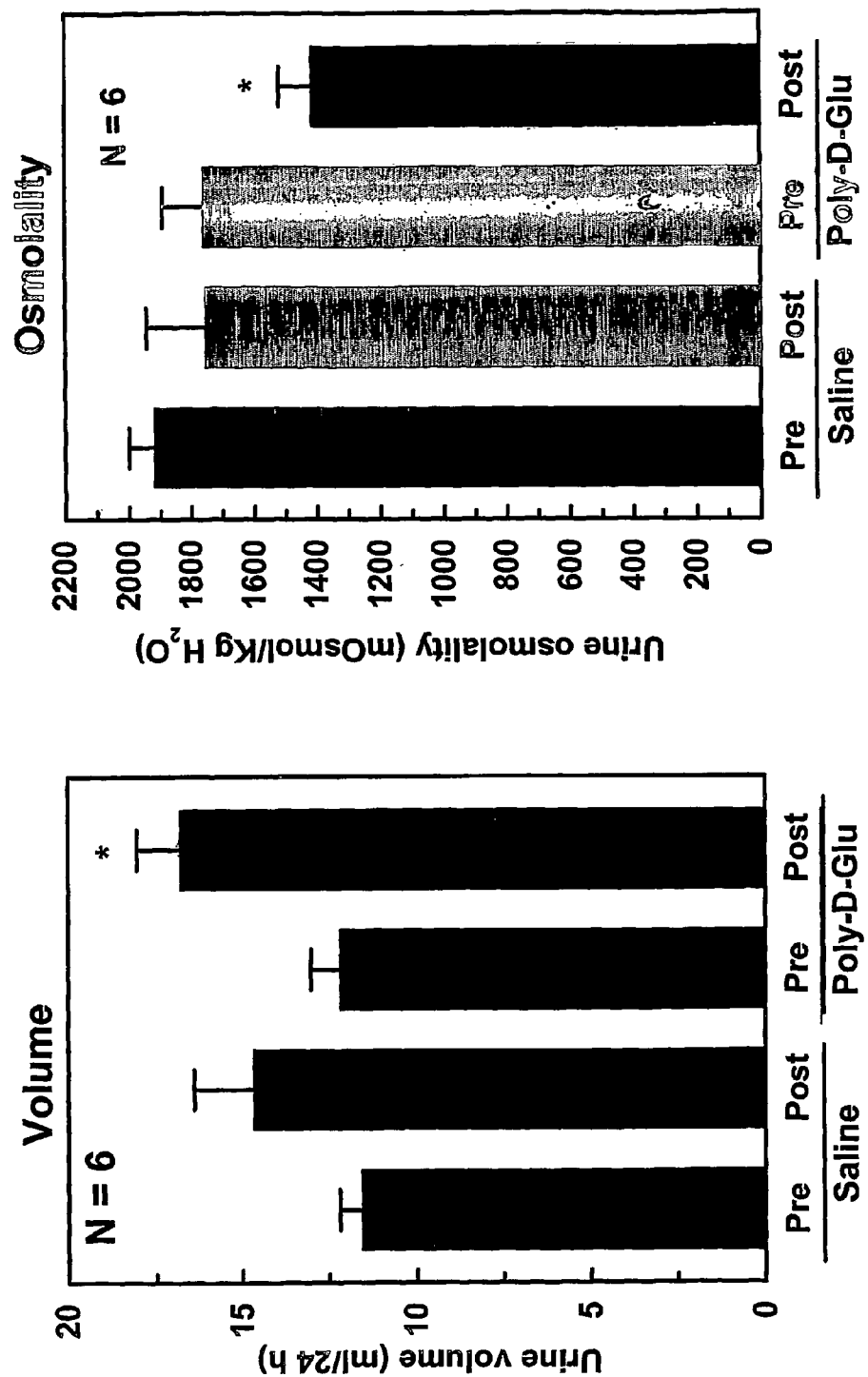
FIG. 11 shows that administration of poly-D-glutamic acid to rats does not cause marked abnormalities (i) in the excretion of water as assessed by 24 hour urine volume (A) and (ii) the ability of kidneys to concentrate urine as assessed by urine osmolality (B). Panel (A) shows the urine volumes in saline or poly-D-glutamic acid treated rats before (Pre) or after (Post) treatment. Panel (B) shows the urine osmolalities in saline or poly-D-glutamic acid treated rats before (Pre) or after (Post) treatment.
Figure 12:
FIG. 12 shows a western blot showing no detectable changes in the protein abundance of aquaporin-1 water channel in kidney cortex. Water absorption in the kidney is mediated by specialized pores or water channels, collectively known as aquaporins. Majority of filtered water (70-80%) is reabsorbed in the proximal tubules (the same renal segments that showed poly-D-glutamic acid-induced morphological alterations—see slides 14 to 26). Aquaporin-1 is abundantly expressed in this renal tubular segment, and accounts for the rapid reabsorption of water.
Figure 13:
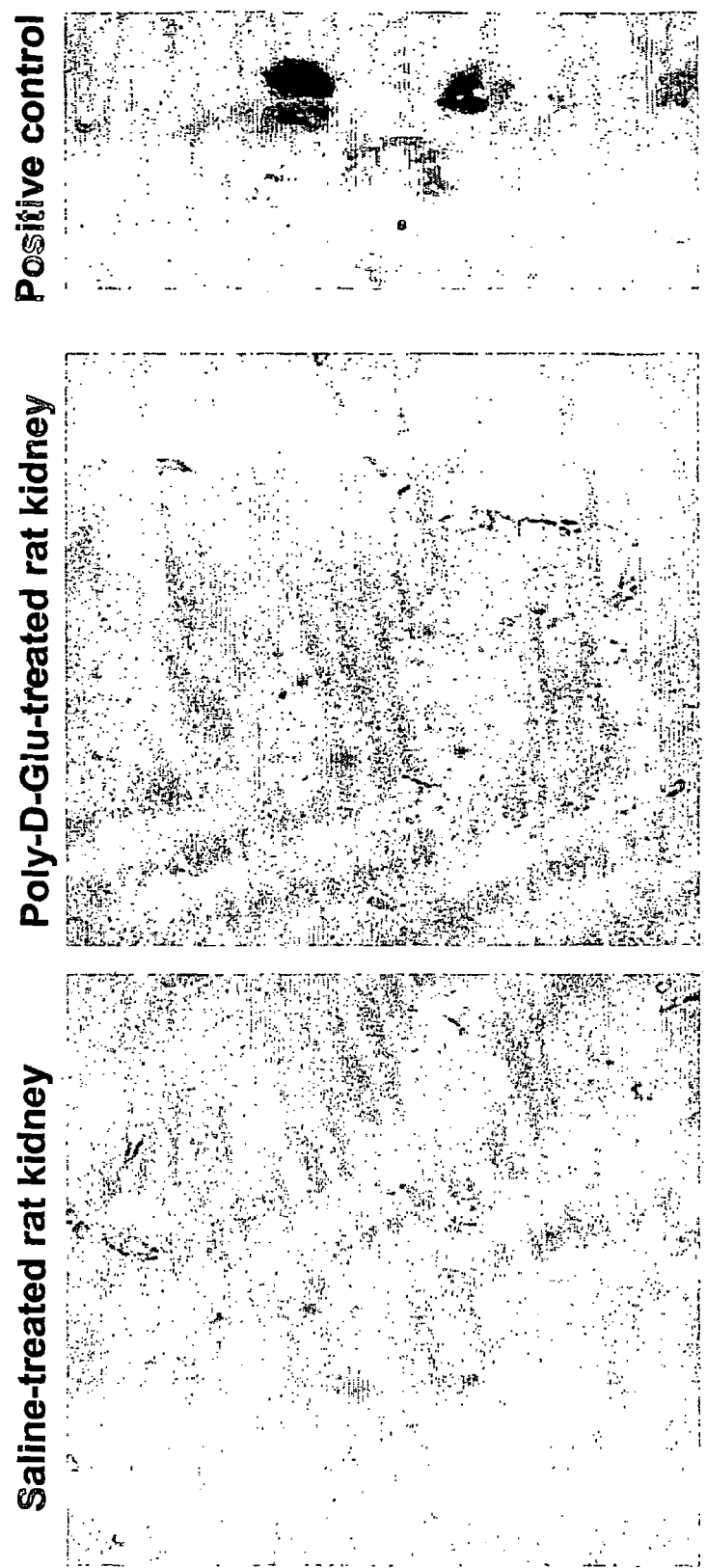
FIG. 13 shows that administration of poly-D-glutamic acid to rats does not cause apoptotic cell death in the renal cortex Poly-D-glutamic acid accumulates in renal cortical proximal tubular lysosomes.
Figure 14:
FIG. 14 shows that using a simple technique of Trichrome staining on paraffin sections of kidneys from rats treated with either saline (A) or poly-D-glutamic acid (B), whether administration of poly-D-glutamic acid results in fibrotic changes in the kidney was examined. The results show that there is not much fibrotic reaction in the kidney.
Figure 14:
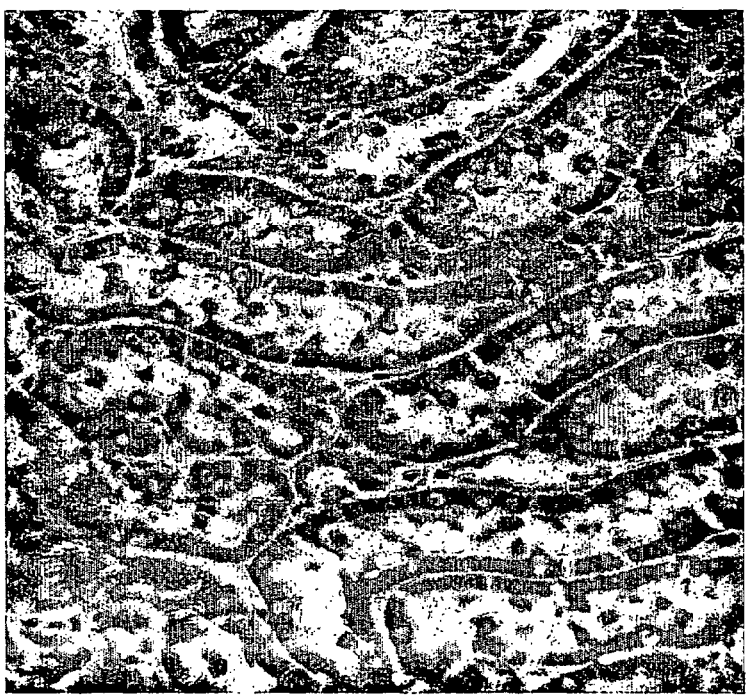
Figure 15:
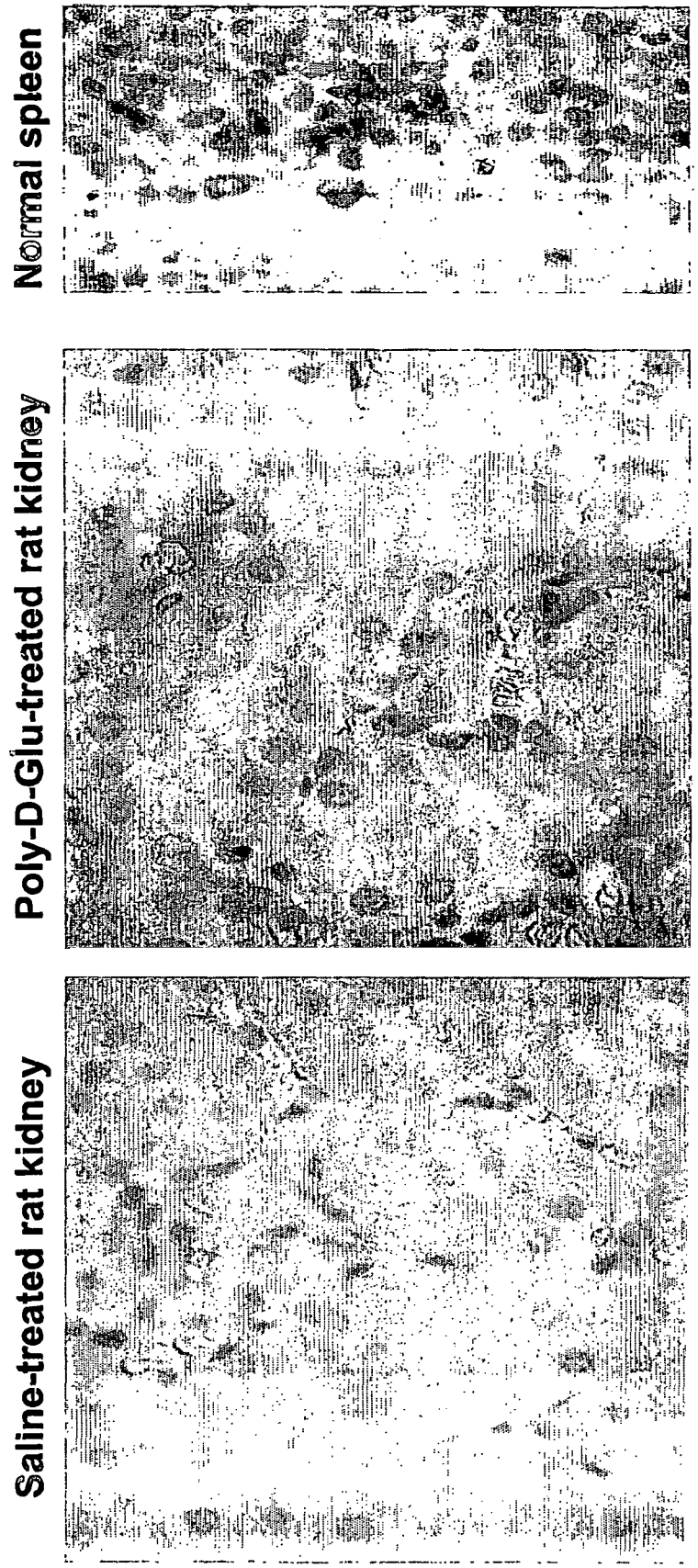
FIG. 15 shows an immunohistochemical staining using a specific antibody to Vimetin, a marker for mesenchymal reaction or changes. The immunohistochemical methods are standard and routinely used in many research and clinical labs. The results show that poly-D-glutamic acid treatment causes detectable mesenchymal changes (B). The right panel (A) shows mesenchymal labeling in normal rat spleen (positive control).
Figure 16:
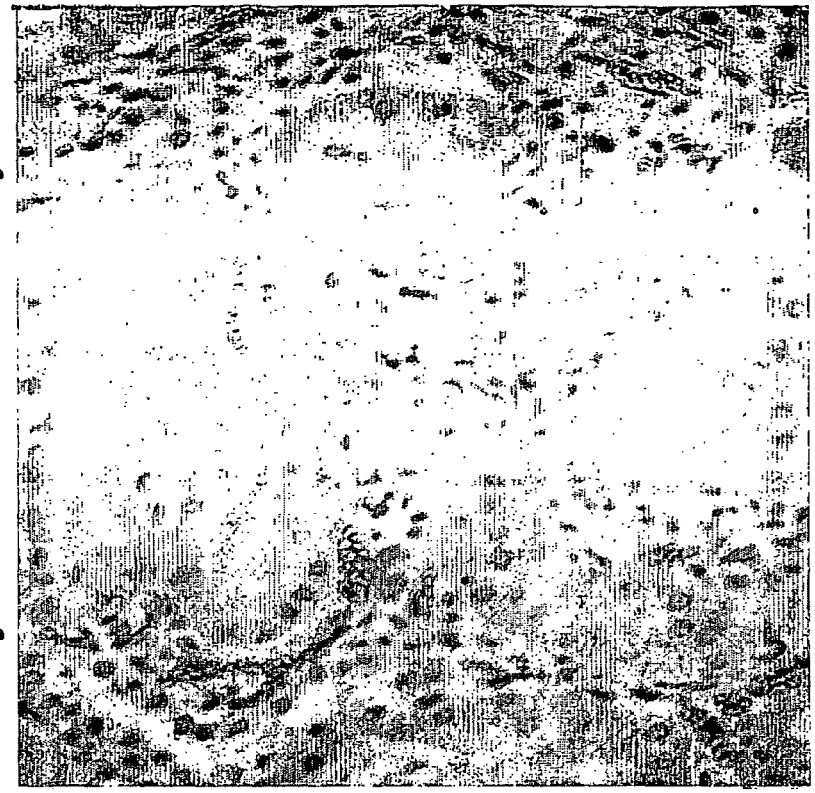
FIG. 16 shows hematoxylin and eosin staining of paraffin sections of kidneys from rats treated with either saline or with poly-D-glutamic acid. Poly-D-glutamic acid treatment causes an enormous increase in the number of interstitial cells (dots between the tubules in panel B).
Figure 16:
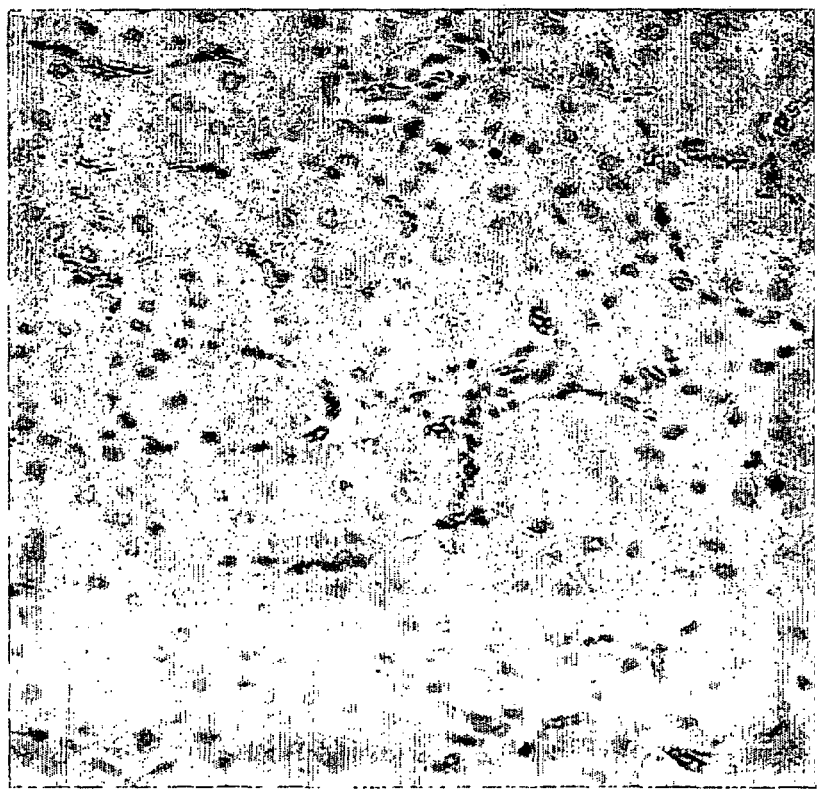
Figure 17:
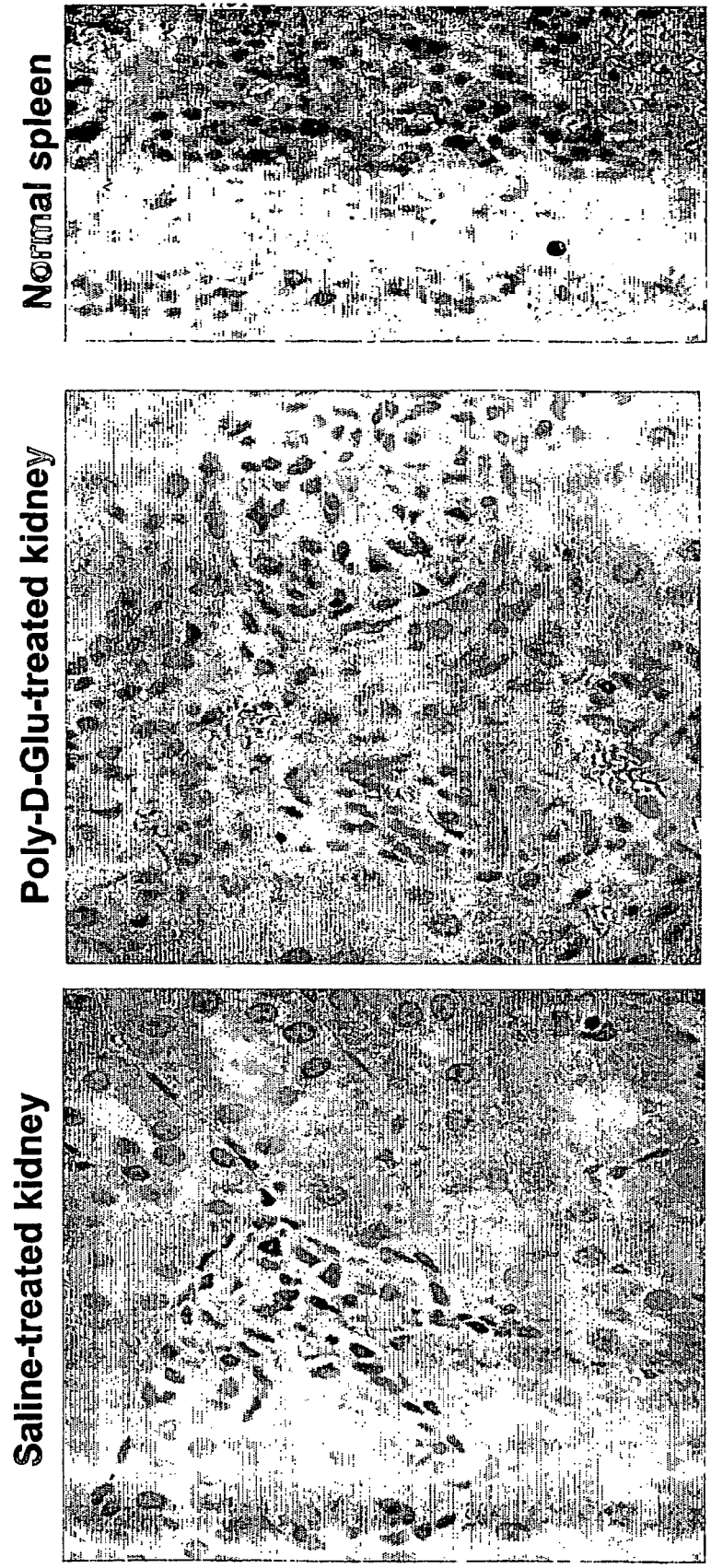
FIG. 17 shows a specific antibody to CD68 surface antigen, excluding the possibility that the interstitial cells in poly-D-glutamic acid treated rats are not macrophages or monocytes. Panel (C) shows positive labeling in rat spleen as a control for staining.
Figure 18:
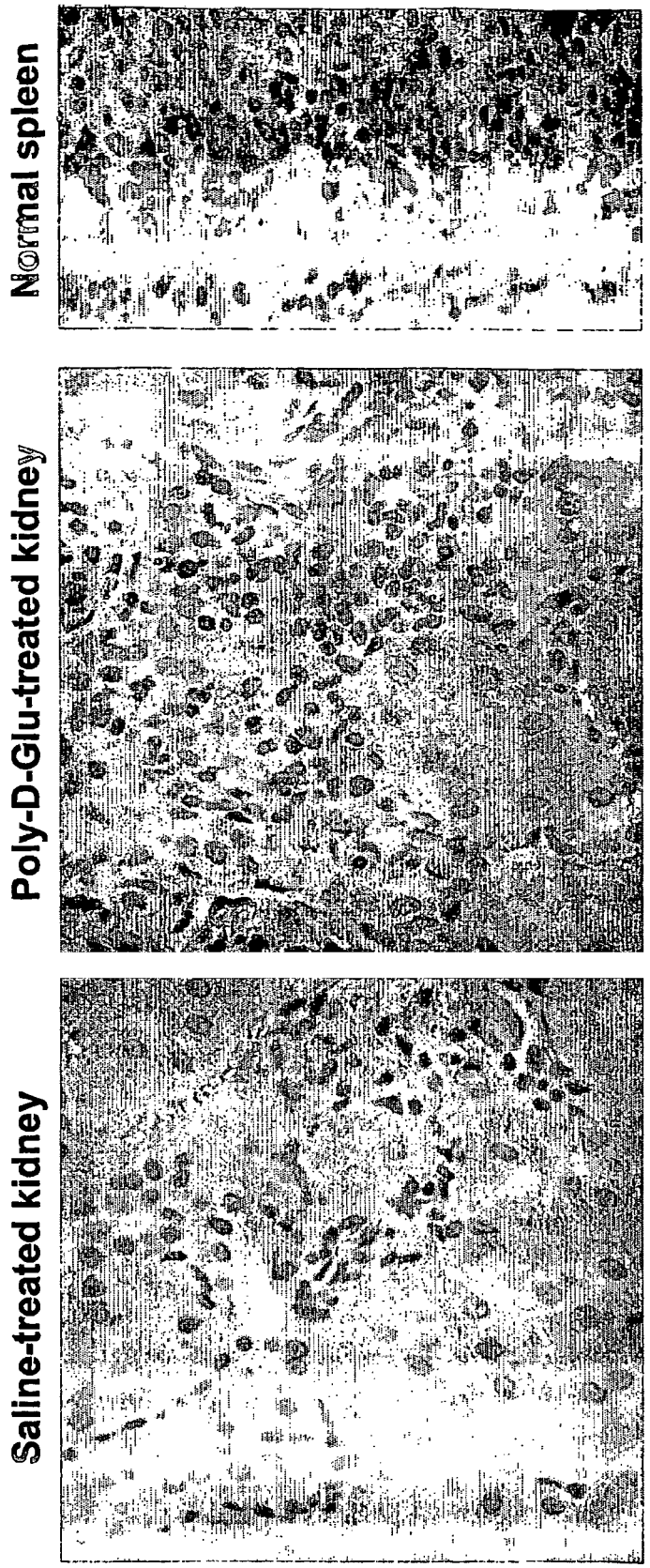
FIG. 18 shows a specific antibody to CD45 surface marker, excluding the possibility that the interstitial cells in poly-D-glutamic acid treated rats are not leukocytes. The right panel shows positive labeling in rat spleen as a control for staining.
Figure 19:
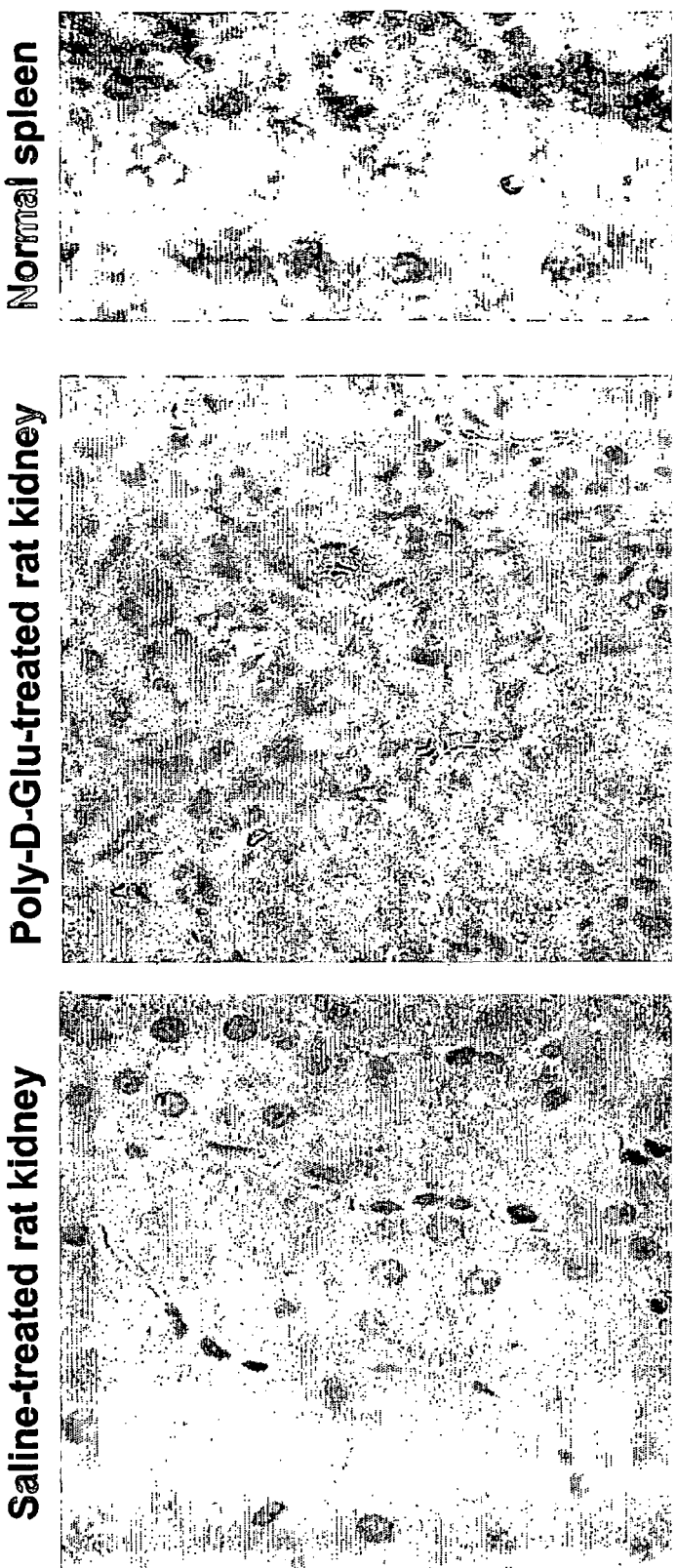
FIG. 19 shows a specific antibody to CD20 surface antigen, excluded the possibility that the interstitial cells in poly-D-glutamic acid treated rats are not B-lymphocytes. Panel (C) shows positive labeling in rat spleen as a control for staining.
Figure 20:
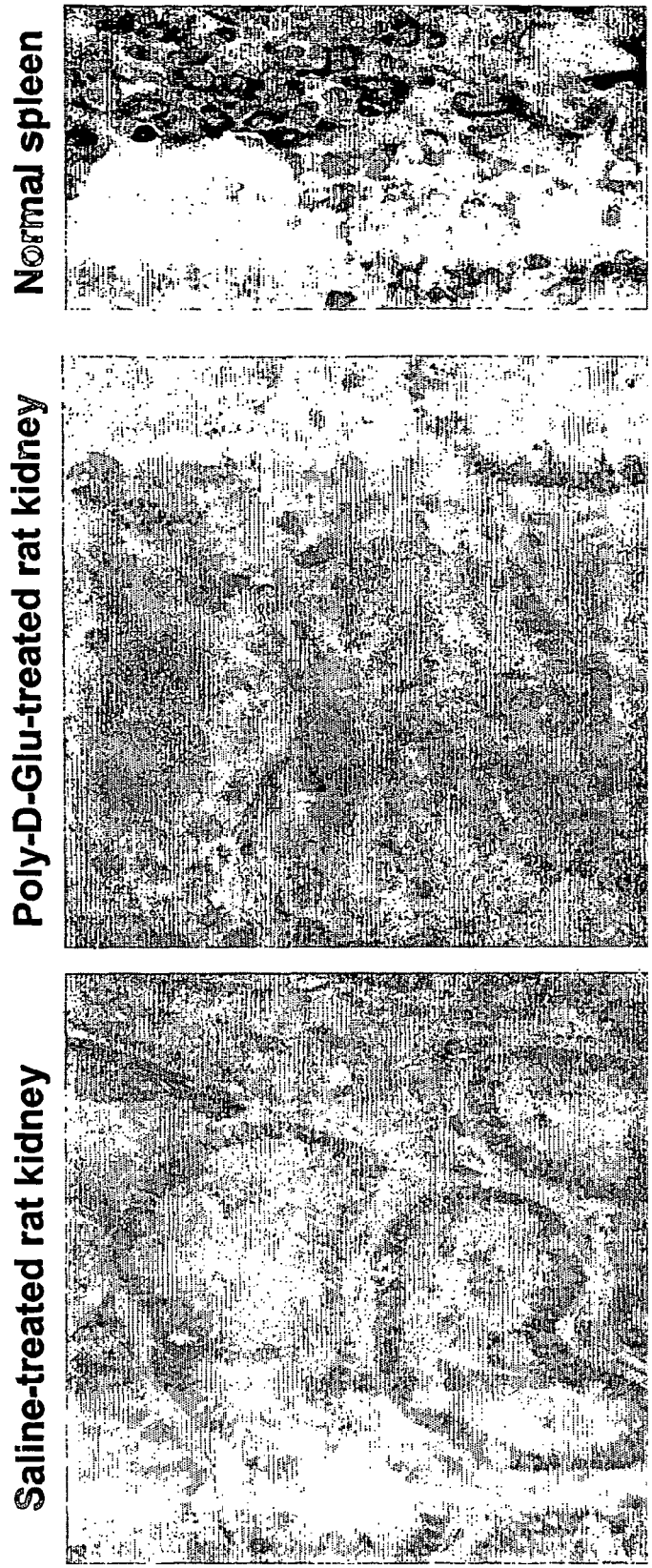
FIG. 20 shows a specific antibody to CD3 surface antigen, excluding the possibility that the interstitial cells in poly-D-glutamic acid treated rats are not T-lymphocytes. The right panel shows positive labeling in rat spleen as a control for staining. Some non-specific labeling on the tubules of both saline and poly-D-glutamic acid treated rat kidney can be seen, but no labeling could be seen on the interstitial cells.
Figure 21B:
Figure 22A:
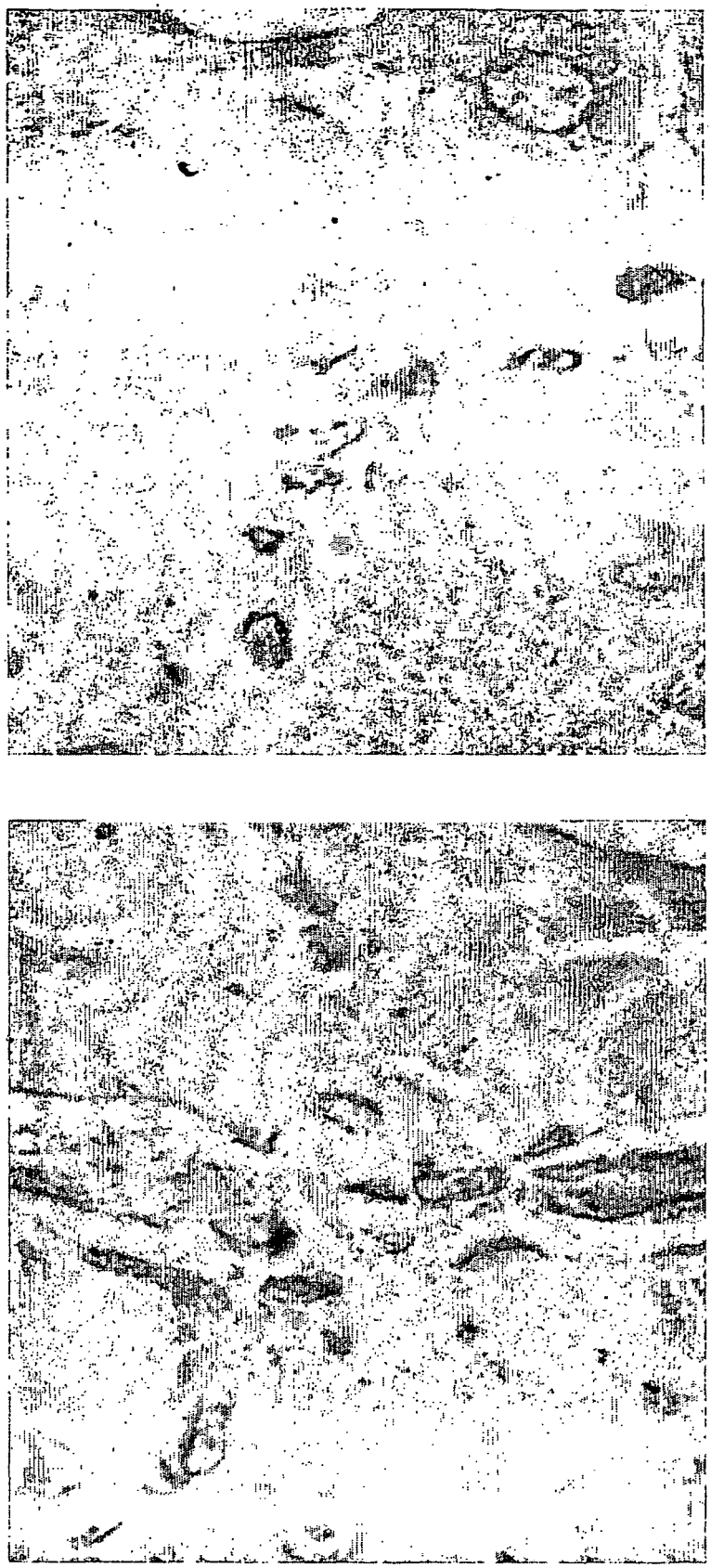
FIGS. 22A and 22B show two more profiles of CD73 positive interstitial cells in poly-D-glutamic acid treated rat kidneys.
Figure 22B:
Figure 23:
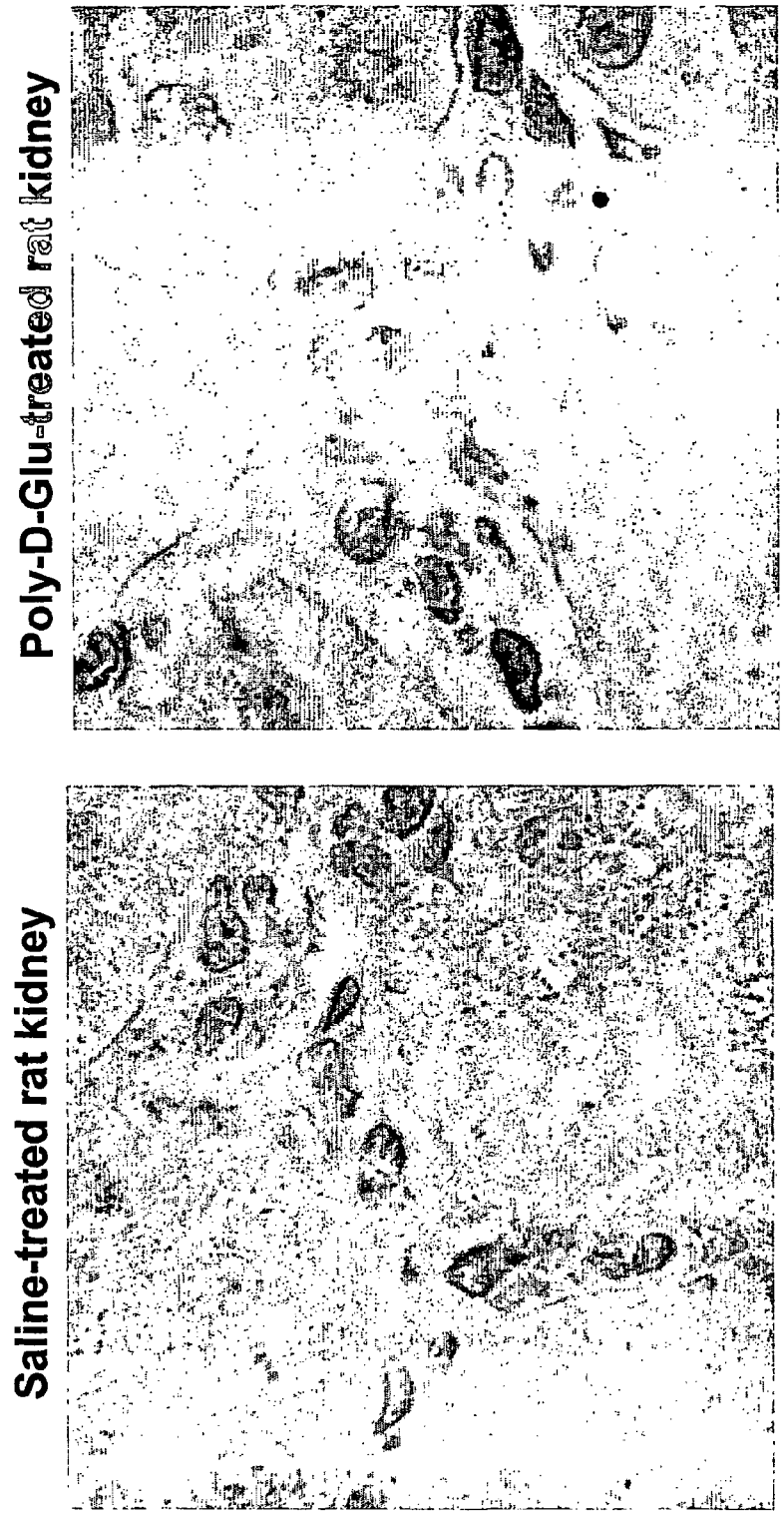
FIG. 23 shows that the proliferating cells express erythropoietin. Erythropoietin is synthesized by a subset of resident fibroblasts. Specific antibody to erythropoietin was used and it was found that the proliferating interstitial cells in poly-D-glutamic acid treated rats strongly stain for erythropoietin. Panel (A) shows labeling of resident fibroblasts in saline treated rat kidneys.
Figure 24:
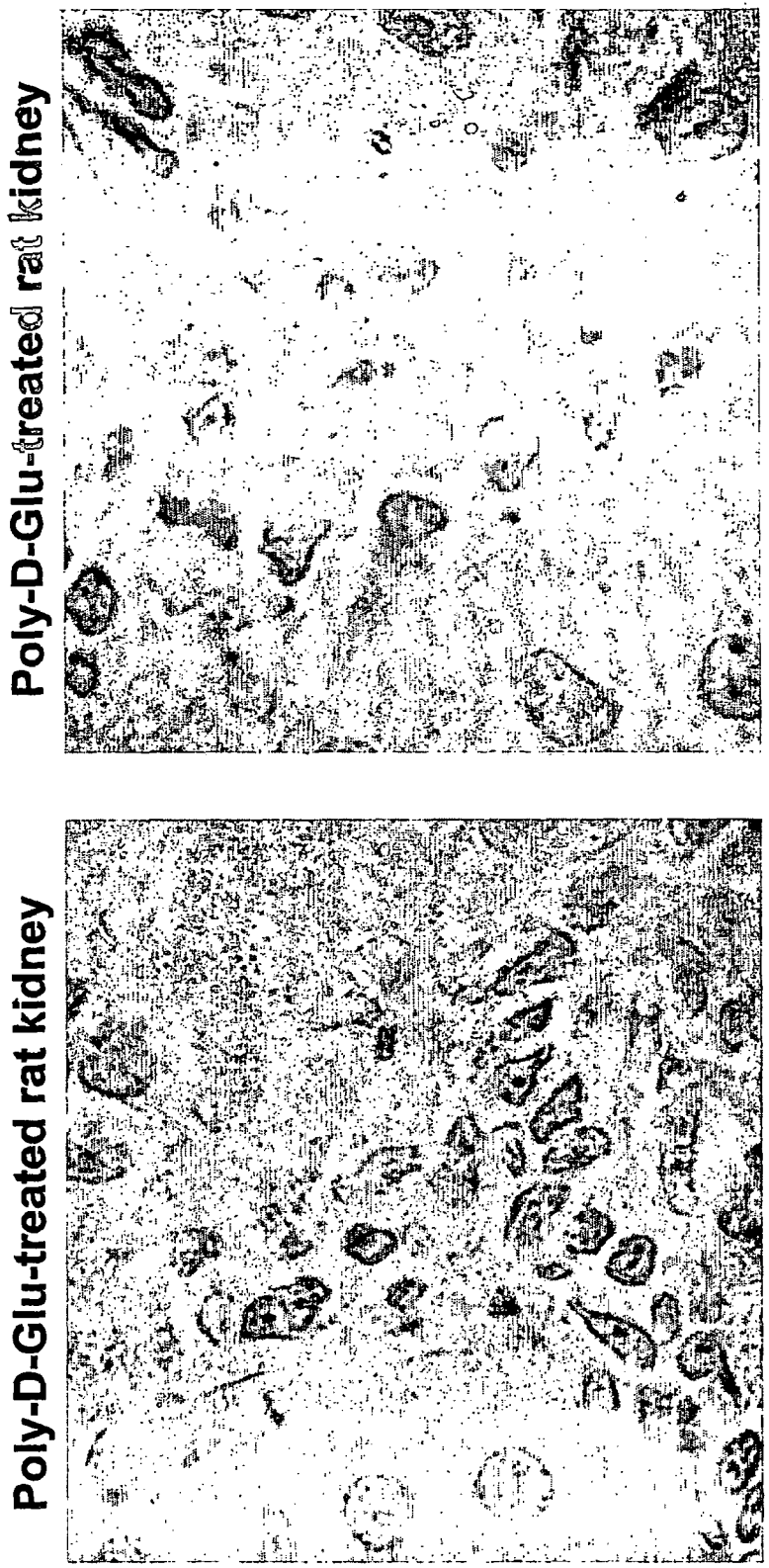
FIG. 24 shows two more profiles of erythropoietin positive interstitial cells in poly-D-glutamic acid treated rat kidneys.
Figure 25:
FIG. 25 shows two different panels both of which show angiogenesis in the renal cortex of poly-D-glutamic acid-treated rat kidney.
Figure 25:
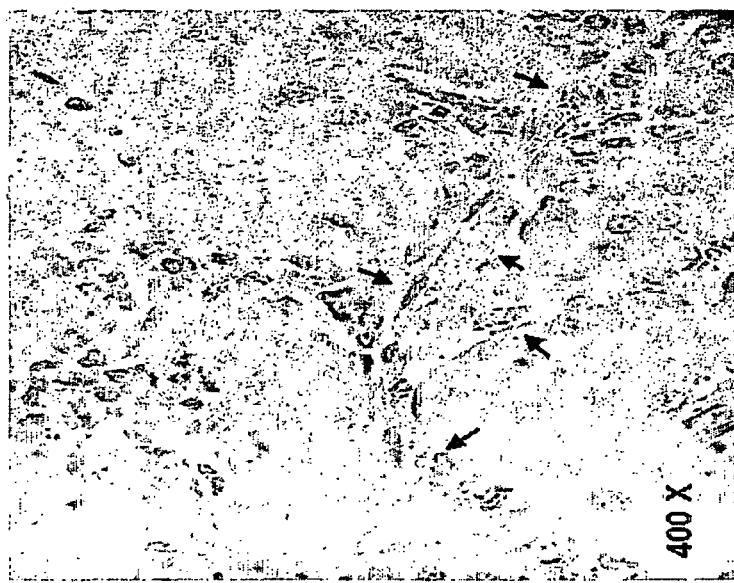
Figure 26:
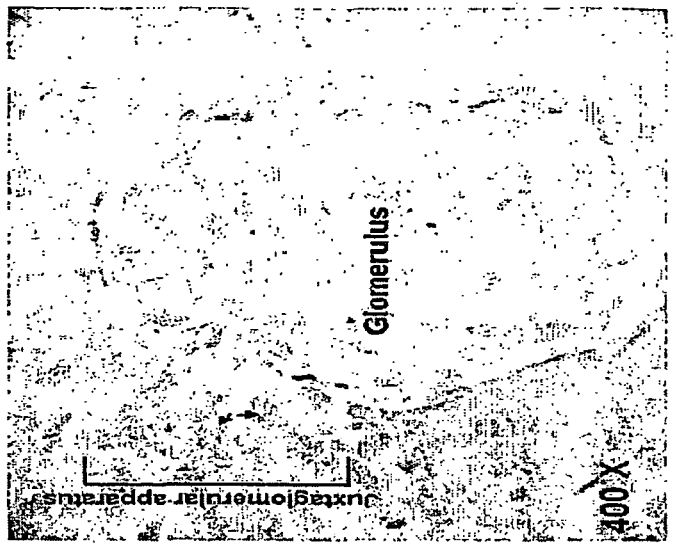
FIG. 26 shows two different panels, both of which show erythropoietin expression in the juxtaglomerular apparatus of a poly-D-glutamic acid treated rat kidney.
Figure 26:
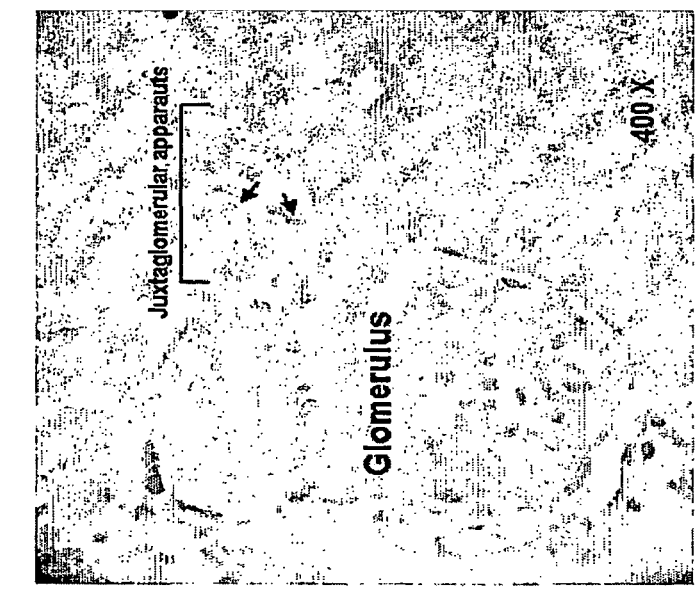
Figure 27:
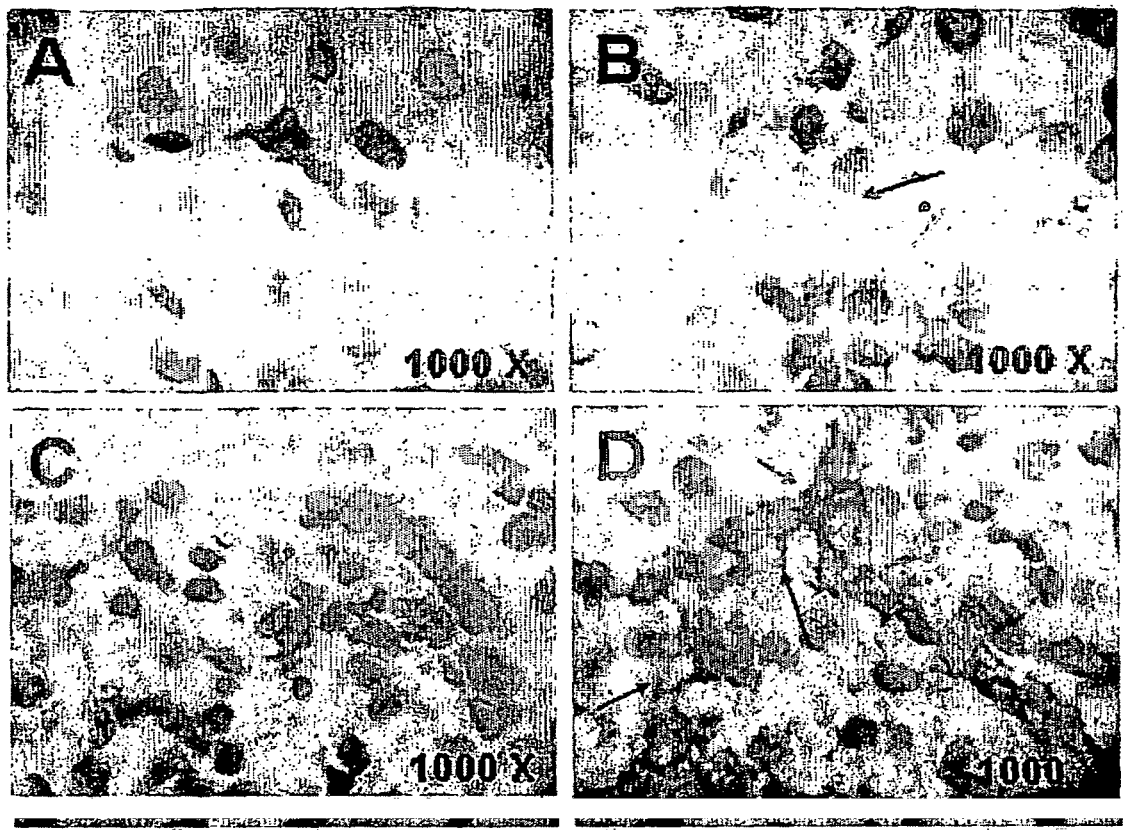
FIGS. 27 A-D show localization of erythropoietin mRNA in peritubular interstitial cells by in situ hybridization. Formalin-fixed, paraffin-embedded kidneys from saline and Poly-D-Glu-treated rats (250 mg/kg/day for 4 days) were processed for in situ hybridization of EPO mRNA. Messenger RNA in the sections was hybridized using digoxygenin-labeled riboprobes that correspond to EPO gene sequence. The length of these riboprobes was 338 bp. Sites of hybridization were visualized by incubating with peroxidase-labeled antidigoxygenin antibody followed by color reaction with diaminebenzidine (DAB).

Protease inhibitors can also be added to the conditioned medium in order to improve EPO yields. Several commercially available protease inhibitors were tested to see if they could prevent EPO degradation at pH5.0. 10× concentrated (Step 1) EPO medium was diluted 1:10 in 50 mM Na Acetate, pH5.0 and then incubated at 37° C. with or without protease inhibitors at a concentration of 5 micrograms/ml. Aliquots were taken over a period of 29 hours and assayed by RIA. This experiment-showed that pepstatin (Sigma) had a significant stabilizing effect on EPO immunoactivity over this time period at pH5.0. Pepstatin was then tested to determine the minimum concentration at which it is effective. Under the same conditions as described above, pepstatin was included into 10× concentrated medium over range of 0.0005 to 1 ug/ml and incubated at 37° C. for 25 hours. The $IC_{50}$ (the concentration at which 50% of the proteases are inhibited) of Pepstatin is approximately 0.02 ug/ml (FIG. 9). To test the effect of pepstatin in the purification process, 0.2 ug/ml of pepstatin was added to the 10× concentrated medium and to the buffers for the S-Sepharose column. Under these conditions, 97% of EPO was recovered from the S-Sepharose Fast Flow column compared to approximately 60% without the use of a protease inhibitor.

The gel filtration chromatography step (Step 4, above) can be replaced by an S Sepharose Fast Flow ion exchange step to remove organic solvents. Fractions containing EPO eluted from the $C_8$ column at approximately 25% propanol can be pooled, the pH was lowered to 5.0 by dilution with nine volumes of 0.05M Na Acetate buffer, pH5.0 and then applied to a S-Sepharose Fast Flow column equilibrated in 50 mM Na Acetate pH5.0 containing 15 mM NaCl. The column was washed with several volumes of this buffer and EPO was then eluted with PBS pH8.0. EPO recovery at this step was quantitative and the final product was found to be free of residual propanol.

D. Example 4

1. Mechanism of Poly-D-Glutamic Acid Induced Acute Lysosomal Storage Condition in Proximal Tubular Cells The mechanism of Poly-D-Glu-induced acute lysosomal storage condition in proximal tubular cells was addressed. After a single intravenous injection, $^{14}$C-poly-D-glutamic acid was rapidly cleared from the plasma and appeared in the urine. Yet, a small, but sizeable fraction of the injected polymer was taken up by the kidney cortex through a saturable process (Kuptake, 150 mg/kg body wt; uptakemax, 96 μg/g cortex). Analytical subcellular fractionation of cortex homogenates demonstrated that at initial stages, the $^{14}$C label was predominantly associated with subcellular particles of intermediate size and low equilibrium density (brush border membrane and enocytic vesicles), and was slowly transferred to larger particles equilibrating at high density, which co-distribute with lysosomal hyrolases. At a concentration of 10 mg/ml (equivalent to its estimated concentration in lysosomes), Poly-D-glutamic acid formed micronic aggregates ($\geq 10$ μm) when brought to a solution at pH$\leq 6$ (pKa of lateral chains of Poly-D-glutamic acid ~4.25). Finally, one day after the injection of Poly-D-glutamic acid, the activities of several lysosomal enzymes (hexoseaminidase, cathepsin B, acid sphigomyelinase, and sulfatase B), but not of all of them (e.g. acid phosphatase), were increased in the kidney cortex. Based on these observations, Poly-D-glutamic acid reaches lysosomes by adsorptive endocytosis and becomes concentrated within these organelles because it withstands hydrolysis until it forms aggregates or precipitates, causing a decrease in the fluidity or the deformability ("gelling") of the lysosomal matrix. This alters the dynamics of intercommunication of these organelles by impairing their fission without a proportionate effect on their fusion properties.

E. Example 5

1. Persistence of EPO-Producing Peritubuiar Cells in Rat Kidney Even After the Cessation of Poly-D-Glutamic Acid Treatment As shown in FIG. 28, even 6 days after the cessation of a 4-day treatment with Poly-D-glutamic acid (250 mg/kg/day), there is persistence of EPO-producing peritubular cells in the rat kidney, which appear to be qualitatively and quantitatively similar to the one observed immediately after a 4-day treatment with Poly-D-glutamic acid. The persistently large number of EPO-producing peritubular cells in Poly-D-glutamic acid-treated rats is due to persistent proliferation or continued survival of the already proliferated cells. The former does not seem to be a possibility, as in earlier studies a significant proliferative response of peritubular cells 7 days after the cessation of Poly-D-glutamic acid treatment as assessed by $^3$H-thymidine incorporation into nuclear DNA of S-phase cells could not be observed. The $^3$H-thymidine incorporation approach only measures the "proliferating cells" but not the total "number of cells" present in the interstitium. In view of these observations the Poly-D-glutamic acid administration alters the phenotype of the peritubular cells, making them perisistently produce EPO without further need for the Poly-D-glutamic acid-induced signaling.

F. Example 6 i. The Ability of the In Vivo Proliferating, EPO-Producing Peritubular Cells to Grow and Produce EPO In Vitro in Culture Alterations in the peritubular fibroblasts (PTFBLC) that Poly-D-glutamic acid administration elicits, via its storage in adjacent proximal tubular cell lysosomes in vivo, i.e., augmented EPO expression and proliferation and potentially increased cell survival, are sustained when cells are isolated from the kidney and placed in culture in the absence of Poly-D-glutamic acid-loaded proximal tubular cells. Continued and spontaneous proliferation and/or EPO expression can be observed, indicating that signals induced by Poly-D-glutamic acid in proximal tubular cells cause permanent alterations in the PTFBLC phenotype. Only human hepatoma cell lines, HepG2 and HepB3, maintain physiologically regulated EPO synthesis in culture and have thus been essential for most investigations on EPO expression and secretion. This experiment specifically examines whether PTFBLC isolated from Poly-D-Glu-treated rat kidney, when placed into culture, maintains EPO expression and continue to proliferate and produce EPO; 2) The nature of phenotypic alteration induced in the PTFBLC by Poly-D-glutamic acid administration. PTFBLC is also monitored to assess its ability to transdifferentiate into myfibroblasts by immunostaining for desmin, α-smooth muscle actin, and TGF-β receptor. TGF-β1 is the most potent inducer of mesenchymal transformation. Other candidates for the induction of mesenchymal transformation are EGF, FGF-2 and IL-1.

For the in vitro studies PTFBLC can be isolated from kidney cortices of Poly-D-glutamic acid treated rats. Poly-D-glutamic acid is administered subcutaneously at a dose of 250 mg/kg body wt/day for 4 consecutive days. Growth curves of PTFBLC can be generated, using the MTT or Thiazoyl assay and direct cell counting. Cellular EPO and 5'-nucleotidase expression (mRNA and protein) and EPO secretion into the media (EIA) is monitored at defined time points. The PTFBLC can also be monitored for myofibroblast transdifferentiation by immunostaining for desmin and α-smooth muscle actin.

To examine the nature of the phenotypic alteration induced in the PTFBLC, low ambient oxygen tension, or Desferroxamine, an iron chelator, or CoCl2, can be used to test whether EPO expression can be stimulated in regulated fashion. In parallel HepG2 and HelB3 cells can be subjected to similar experimental manipulations as positive controls for regulated EPO production. If these maneuvers fail stimulate EPO production in PTFBLC, this indicates that EPO production in these cells is constitutive.

G. Example 7 i. Replication of Proliferation of EPO-Producing Cells In Vitro Using Co-Cultures of Poly-D-Glutamic Acid-Loaded Proximal Tubular Cells and Renal Fibroblasts It is well known that a fine and complex cytokine network exists in the tubulointerstitial microenvironment, which can be perturbed in abnormal or disease conditions. In fact, progression of renal diseases has been ascribed to the damaging effect of some of the released cytokines (e.g. TFGβ). The apparently non-lethal lysosomal storage condition induced by Poly-D-glutamic acid in proximal tubular cells can result in the release of a variety of cytokines or other signaling molecules, one or more of which specifically stimulate the spectacular proliferation of EPO-producing peritubular cells.

Conditioned media co-cultures: To examine the possibility of a paracrine signaling mechanism in the induction of EPO-producing cells, PTFBLC and proximal tubular cells from controls and Poly-D-glutamic acid-treated animals are co-cultured using transwells. In this approach proximal tubular cells are grown in the bottom wells and PTFBLC from the corresponding group of rats are grown on top of the transwell that is immersed in the medium shared by both cell types. Thus the effect of media conditioned by the proximal tubular cells on the growth and EPO-producing ability of PTFBLC can be studied, which provides information about the existence of any paracrine effect. Growth curves of PTFBLC from control and experimental animals can be generated, using the MTT or Thiazoyl blue assay. Cellular EPO and 5'-nucleotidase expression (mRNA and protein) and EPO secretion into the media (ELISA) can be monitored at defined time points.

Figure 29:
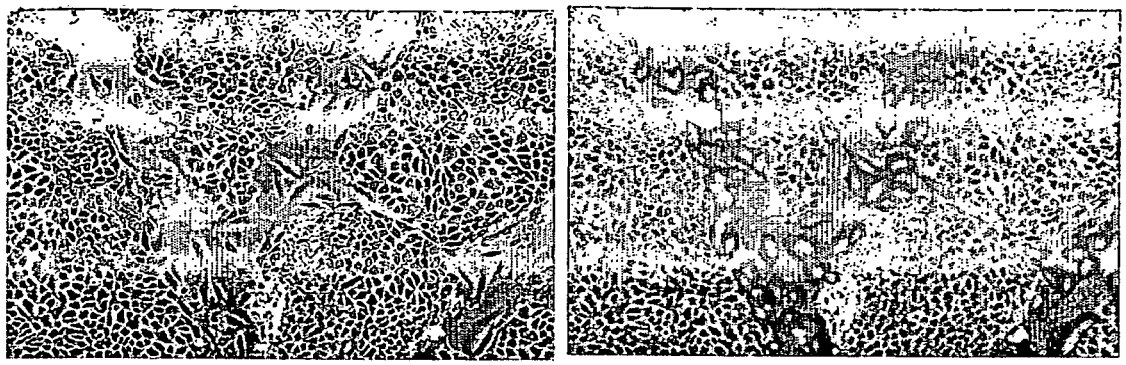
FIG. 29 shows rat renal fibroblasts in co-culture with rat proximal tubular cells in which rat renal fibroblasts are either untagged (left panel) or tagged with CFDA cell tracker (right panel). Proximal tubular cell monolayer was scraped with a sterile pipette tip and fibroblasts were then placed into the media, from where they migrate into the open areas, attach and integrate.

Direct co-cultures: PTFBLC and proximal tubular cells can be placed in direct co-culture as illustrated in FIG. 29. The Figure shows confocal microscopy images of rat proximal tubular cells, cobble stone pattern, and renal fibroblasts, spindle shaped, in co-culture. Renal fibroblasts are either untagged (left panel) or tagged with the CFDA cell tracker (right panel). In this experiment a proximal tubular cell monolayer was scraped with a sterile pipette tip and PTFBLC were then placed into the media, from where they migrate into the open areas, attach and make contact with proximal tubular cells. In the co-culture system employed (FIG. 29), control and experimental proximal tubular cells can be grown to ~50% subconfluence and then PTFBLC are added to the media. Fibroblasts are labeled with the green fluorescent CFDA cell tracker in order to easily identify their location in co-culture. EPO release into the media (ELISA), EPO expression (in situ hybridization and immunocytochemistry), cell proliferation of fibroblast cells (BrdU labeling) and apoptosis (TUNNEL assay) can be monitored under these direct co-culture conditions.

If exposure of fibroblasts to conditioned media from experimental or control proximal tubular cells, as defined above, stimulate their proliferation and EPO-expression, the temporal relationship between exposure to conditioned media and cellular responses can be defined, i.e., onset and offset, after adding or removing conditioned media, respectively.

The permanent or transient nature of the in vivo changes induced in PTFBLC by Poly-D-glutamic acid loading of proximal tubular lysosomes can be defined in these culture studies by monitoring, overtime, the stability of phenotypic characteristics of PTFBLC, as observed in vivo. The in vitro induceability and involved signals that mediate phenotypic changes of PTFBLC can be examined by showing that conditioned media obtained from Poly-D-glutamic acid-loaded proximal tubular cells alone or direct cell-to-cell contact in a co-culture system are effective in sustaining or re-inducing EPO expression and cytokine responses. The general effectiveness and oxygen-independence of these novel, fibroblast-stimulating and EPO-inducing signals, when inducing a constitutive EPO expression pattern and suppressing regulated EPO expression in these cells, can indicate a transcriptional EPO regulatory mechanism.

Establishment of the Poly-D-glutamic acid model in mice: As an extension of the above in vitro mechanistic studies to in vivo conditions, a Poly-D-glutamic acid model can be established in mice. Successful establishment of Poly-D-glutamic acid model in mice provide the opportunity for a battery of molecular genetic studies using the numerous transgenic and gene knockout mice that are currently available, such as cytokine receptor transgenics. The use of Poly-D-glutamic acid in the genetically altered mice throws light on the genomic regulation of EPO production. FVB/N mice are used, and injected with Poly-D-glutamic acid subcutaneously at a dose of 250 mg/kg body wt/day for 4 days, just as in the rat model. Control mice canreceive daily saline injections subcutaneously. On day 5, the mice can be euthanized, kidneys harvested and processed for light and electron microscopy, and protein and mRNA assays. Poly-D-glutamic acid-induced lysosomal overload can be assessed by the above methods. Proliferation of peritubular cells can be confirmed by light microscopy and BrdU labeling. Expression of EPO protein and mRNA by the proliferating peritubular cells can be assessed by immunohistochemistry and in situ hybridization, respectively by the methods established herein. Since rat and mouse are both rodents, the Poly-D-glutamic acid model can be successfully established in the mouse model It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout this application, various publications are referenced in parentheses. The disclosures of these publications in their entireties are hereby incorporated by reference into this application in order to more fully describe the state of the art to which this invention pertains.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Abbate M, and Remuzzi G. Proteinuria as a mediator of tubulointerstitial injury. Kidney Blood Press Res 22: 37-46, 1999.
2. Anagnostou A, Vercellotti G, Barone J, Fried W. Factors which affect erythropoiesis in partially nephrectomized and sham-operated rats. Blood 48:425-433, 1976.
3. Bachmann S, Le Hir M. and Eckardt K. Co-localization of erythropoietin messenger RNA and ecto-5'-nucleotidase iimmunoreactivity in peritubular cells of rat renal cortex indicates that fibroblasts produce erythropoietin. J Histochem Cytochem 41:335-341, 1993.

4. Bellizzi V, Sabbatini M, Fuiano G, Sansone G, Magri P, Uccello F, Andreucci M, De Nicola L, and Cianciaruso B. The impact of early normalization of haematocrit by erythropoietin on renal damage in the remnant kidney model. Nephrol Dial ransplant 13:2210-2215, 1998.

5. Burton C, and Harris K P G. The role of proteinuria in the progression of chronic renal failure. Am J Kidney Dis 27:765-775, 1996.

6. Carlini R, Reyes A, and Rothstein M. Recombinant human erythropoietin stimulates angiogenesis in vitro. Kidney Int 47:740-745, 1995.

7. Dendorfer U. Molecular biology of cytokines. Artif Organs 20:437-444, 1996.

8. Donnelly S. Why erythropoietin is made in the kidney? The kidney functions as a crimeter. Am J Kidney Dis 38:415-425, 2001.

9. Eddy A A. Interstitial nephritis induced by protein overload proteinuria. Am J Pathol 135:719-733, 1989.

10. Eddy A A. Expression of genes that promote renal interstitial fibrosis in rats with proteinuria Kidney Int 49:S49-S54, 1996.

11. Eddy A A. Molecular basis of renal fibrosis. Pediatr Nephrol 15:290-301, 2000.

12. Eddy A A. Role of cellular infiltrates in response to proteinuria Am J Kidney Dis 37:S25-S29, 2001.

13. Ferrara N. Molecular and biological properties of vascular endothelial growth factor J Mole Med 77:527-543, 1999.

14. Gandhi R, Le Hir M, and Kaissling B. Immunolocalization of ecto-5'-nucleotidase in the kidney by a monoclonal antibody. Histochemistry 95:165-174, 1990.

15. Ghielli M, Verstrepen W, de Greef K, Vercauteren S, Ysebaert D, Nouwen E, and de Broe M. inflammatory cells in renal pathology. Nephrologie 19:59-67, 1998.

16. Gleadle J M, and Ratcliffe P J. Induction of hypoxia-inducible factor-1, erythropoietin, vascular endothelial growth factor, and glucose transporter-1 by hypoxia: evidence against a regulatory role for Src kinase. Blood 89:503-509, 1997.

17. Ivan M, Kondo K, Yang H, Kim W, Valiando J, Ohh M, Salic A, Asara J M, Lane W S, and Kaelin W G Jr. HIFα targeted for VHL-mediated destruction by proline hydroxylation: implications for O2 sensing. Science 292:646-648, 2001.

18. Jaakkola P, Mole D R, Tian Y-M, Wilson M I, Gielbert J, Gaskell S J, Kriegsheim A, Heberstreit H F, Mukerji M, Schofiled C J, Maxwell P H, Pugh C W, and Ratcliffe P J. Targeting of HIFα to the von Hippel-Lindau urbiquitylation complex by O2-regulated prolyl hydroxylation Science 292:468-472, 2001.

19. Jelkmann W. Erythropoietin: structure, control of production, and function. Physio Rev 72:449-48, 1992.

20. Johnson D W, Saunders H J, Brew B K, Ganesan A, Baxter R C, Poronnik P, Cook D I, Gyory A Z, Filed M J, and Pollock C A. Human renal fibroblasts modulate proximal tubule cell growth and transport via the IGF-1 axis. Kidney Int 52:1486-1496, 1997.

21. Kaissling B, Heg I, Loffing J and Le Hir M. Morphology of interstitial cells in the healthy kidney. Anat Embryol 193:303-318, 1996.

22. Keane W F. Proteinuria: its clinical importance and role in progressive renal disease. Am J Kidney Dis 35:S97-S105, 2000.

23. Kendall R G. Erythropoietin. Clin Lab Hematol 23:71-80, 2001.

24. Kishore B K, Fuming L, Maldague P, Tulkens P M, and Courtoy P J. Mechanism of the thesaurismosis and altered lysosomal dynamics induced by poly-D-glutamic acid in kidney proximal tubular cells. Lab Invest 74:1025-1037, 1996b.

25. Kishore B K, Ibrahim S, Lambricht P, Laurent G, Maldague P, and Tulkens P M. Comparative assessment of poly-L-aspartic and poly-L-glutamic acids against gentamicin-induced renal lysosomal phospholipidosis, phospholipduria, and cell proliferation in rats, J Pharmacol Exp Ther 262:424-432, 1990

26. Kishore B K, Krane C M, Dilulio D, Menon A G, and Cacini W. Expressionl of renal aquaporins 1, 2, and 3 in a rat model of cisplatin-induced polyuria. Kidney Int 58:701-711, 2000.

27. Kishore B K, Lambricht P, Laurent G, Maldague P, Wagner R, and Tulkens P M. Mechanism of protection afforded by polyaspartic acid against gentamicin-induced phospholipidosis. II. Comparative in vitro and in vivo studies with poly-L-aspartic, poly-L-glutamic and poly-D-glutamic acids. J Pharmacol Exp Ther 255:875-885, 1990b.

28. Kishore B K, Maldague P, Tulkens P M, and Courtoy P J. Poly-D-glutamic acid induces an acute lysosomal the saurismosis of proximal tubules and a marked proliferation of interstitium in rat kidney. Lab Invest 74:1013-1023, 1996a.

29. Koury S, Bondurant M, and Koury M. Localization of erythropoietin synthesizing cells in murine kidneys by in situ hybridization. Blood 71:524-527, 1988.

30. Koury S, Koury M, Bondurant M, Caro J, and Graber S. Quntitation of erythropoietin-producing cells in kidneys of mice by in situ hybridization. Correlation with hematocrit, renal erythropoietin mRNA and serum erythropoietin concentration. Blood 74:645-651, 1989.

31. Krantz S. Erythropoietin. Blood 77:419-434, 1991.

32. Lacombe C, and Maveux P. The molecular biology of erythropoietin, Nephrol Dial Transplant 14:22-28, 1999.

33. Lando D F, Peet D J, Whelan D A, Forman J J, and Whitelae M L. Aspargine hydroxylation of HIFα transactivation domain: a hypoxic switch. Science 295:858-861, 2002.

34. Le Hir M, and Kaisslini B. Distribution of 5'-nucleotidase in the renal interstitium of the rat. Cell Tissue Res 258: 177-182, 1989.

35. Maxwell P, Feguson L G, Nicholls L G, Johsnson M H, and Ratcliff P J. The interstitial response to renal injury: fibroblast-like cells show phenotypic changes and have reduced potential for erythropoietin gene expression. Kidney Int 52:715-724, 1997.

36. Maxwell P, Osmond M, Pugh C W, Heryet A, Nicholls L G, Tan C C, Doe B G, Ferguson D J, Johsnson M H, and Ratcliffe P J. Identification of the renal erythropoietin-producing cells using transgenic mice. Kidney Int 44:1149-1162, 1993.

37. Priyadarshi A, Periyasamy S, Burke T J, Britton S L, Malhotra D, and Shapiro J I. Effects of reduction of renal mass on renal oxygen tension and erythropoietin production in the rat. Kidney Int 61:542-546, 2002.

38. Ribatti D, Presta M, Vacca A, Rial R, Giuliani R, Dell'Era P, Nico B, Roncali L, and Dammacco F. Human erythropoietin induces a pro-angiogenic phenotype in cultured endothelial cells and stimulates neovasculization in vivo. Blood 93:2627-2636, 1999.

39. Schena F P. Cytokine network and resident renal cells in glomerular diseases. Nephrol Dial Transplant 14 Suppl1: 22-26, 1999.

40. Schuster S, Koury S, Bohrer M, Salceda S, and Caro J. Cellular sites of extra renal and renal erythropoietin production in anaemic rats. Brit J Hemat 81:153-159, 1992

41. Shih S C, and Claffey K P. Hypoxia-mediated regulation of gene expression in mammalian cells, In J Exp Pathol 79:347-357, 1998.
42. von Kooten C Langers A M J, Brujin J A, and Daha M R. Role of tubular cells in progressive renal disease. Kidney Blood Press Res 22:53-61, 1999,
43. Westenfelder C. Unexpected renal actions of erythropoietin. Exp Nephrol 10:294-298, 2002.
44. Wetenfelder C, and Baranowski R L. Erythropoietin stimulates proliferation of human renal carcinoma cells. Kidney Int 58:647-657, 2000
45. Westenfelder C, and Baranowski R L. Erythropoietin treatment ameliorates ischemic acute renal failure in rats by its anti-apoptotic, motogenic and mitogenic actions. J Am Soc Nephrol 12:793A, 2001.
46. Westenfelder C, Biddle D L, and Baranowsli R L. Human, rat and mouse kidney cells express fuctional erythropoietin receptors. Kidney Int 55:808-820, 1999.
47. Westenfelder C, Joseph A, Swenson L, Isaac J, and Baranowski R L. Dual roles of NFkB in ischemic acute renal failure in rats: (1) mediates maladaptive suppression of erythropoietin (EPO) gene, (2) mediates EPO's anti-apoptotic effects in proximal tubular cells. Abstract # T323 accepted for presentation at the World Congress of Nephrology, Berlin, Jun. 8-12, 2003.
48. Wolf G, and Neilson E G. Molecular mechanisms of tubulointerstitial hypertrophy and hyperplasia. Kidney Int 39:401-420, 1991.
49. Youssoufian H, Longmore G, Neumann D, Yoshimura A, and Lodish H F. *Structure, function, and activation of the erythropoietin receptor.* Blood 81:2223-2236, 1993.
50. Zoja C, Benigni A, and Remuzzi G. Protein overload activates proximal tubular cells to release vasoactive and inflammatory mediators. Exp Nephrol 7:420-428, 1999.

We claim:

1. A pharmaceutical composition comprising an erythropoietin production inducing peptide (EPIP), wherein the EPIP is selected from the group consisting of poly-D-glutamic acid, poly-L-glutamic acid, poly-D-aspartic acid and poly-L-aspartic acid;
   erythropoietin; and
   a pharmaceutically acceptable diluent, adjuvant or carrier.

2. The pharmaceutical composition of claim 1, comprising a therapeutically effective amount each of the erythropoietin and the EPIP.

3. The pharmaceutical composition of claim 1, comprising a therapeutically effective amount of the EPIP.

4. The pharmaceutical composition of claim 1, wherein the erythropoietin is recombinant.

5. The pharmaceutical composition of claim 1, wherein the EPIP is poly-D-glutamic acid.

6. The pharmaceutical composition of claim 1, further comprising a preservative, wherein the preservative comprises benzyl alcohol, a paraben and phenol, or a mixture thereof.

7. The pharmaceutical composition of claim 1, further comprising a buffering agent.

8. The pharmaceutical composition of claim 7, wherein the buffering agent comprises citrate, phosphate, tartrate, succinate, adipate, maleate, lactate and acetate buffers, sodium bicarbonate, and sodium carbonate, or a mixture thereof.

9. The pharmaceutical composition of claim 1, further comprising an isotonicity adjusting agent, wherein the isotonicity adjusting agent comprises sodium chloride, glycerol, mannitol, sorbitol, or a mixture thereof.

10. The pharmaceutical composition of claim 1, further comprising a pH adjusting agent that adjusts the pH of the solution within the range of 5-8.

11. The pharmaceutical composition of claim 1, further comprising human serum albumin.

12. The pharmaceutical composition of claim 1, wherein the pharmaceutical composition is an aqueous solution, a non-aqueous suspension, or a dry powder.

13. The pharmaceutical composition of claim 1, wherein the pharmaceutical composition is in an oral dosage form.

14. The pharmaceutical composition of claim 1, further comprising a fatty acid, a surfactant, enteric material, or a mixture thereof.

15. The pharmaceutical composition of claim 1, wherein the pharmaceutical composition is an in an injectable form.

16. A method for treating a condition selected from the group consisting of anemia, Crohn's Disease, ulcerative colitis, chronic renal insufficiency, end stage renal disease and wound healing, comprising:
   administering a therapeutically effective amount a pharmaceutical composition comprising an erythropoietin production inducing peptide (EPIP), wherein the EPIP is selected from the group consisting of poly-D-glutamic acid, poly-L-glutamic acid, poly-D-aspartic acid and poly-L-aspartic acid;
   erythropoietin; and
   a pharmaceutically acceptable diluent, adjuvant or carrier, to a subject in need thereof.

17. The method of claim 16, wherein the EPIP is poly-D-glutamic acid.

18. The method of claim 17, wherein the administration of the poly-D-glutamic acid results in a red blood cell level of 5000 or more erythrocytes per µL of blood.

19. The method of claim 16, wherein the method of treatment results in angiogenesis of a kidney of the subject.

20. The method of claim 16, wherein the subject is a mammal.

21. The method of claim 16, wherein the subject is human.

22. The method of claim 16, wherein the pharmaceutical composition is administered by intravenous or intramuscular or subcutaneous or intraperitoneal injection.

23. The method of claim 16, wherein pharmaceutical composition is administered orally or rectally.

24. The method of claim 16, the pharmaceutical composition is administered by inhalant.

25. The method of claim 24, wherein the administration by inhalant is via a spraying or droplet mechanism.

* * * * *

```
SEQUENCE LISTING

<160> NUMBER OF SEQ ID NOS: 2

<210> SEQ ID NO 1
<211> LENGTH: 193
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 1

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Gln Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 2
<211> LENGTH: 3398
<212> TYPE: DNA
<213> ORGANISM: Artificial Sequence
```

<220> FEATURE:
<223> OTHER INFORMATION: Description of Artificial Sequence; Note = synthetic construct

<400> SEQUENCE: 2

```
agcttctggg cttccagacc cagctacttt gcggaactca gcaacccagg catctctgag      60
tctccgccca agaccgggat gcccccagg aggtgtccgg gagcccagcc tttcccagat     120
agcagctccg ccagtcccaa gggtgcgcaa ccggctgcac tccctcccg cgacccaggg     180
cccgggagca gccccatga cccacacgca cgtctgcagc agcccgtca gccccggagc     240
ctcaacccag gcgtcctgcc cctgctctga cccccgggtgg cccctacccc tggcgacccc     300
tcacgcacac agcctctccc ccaccccac ccgcgcacgc acacatgcag ataacagccc     360
cgaccccgg ccagagccgc agagtccctg ggccaccccg gccgctcgct gcgctgcgcc     420
gcaccgcgct gtcctcccgg agccggaccg gggccaccgc gcccgctctg ctccgacacc     480
gcgccccctg gacagccgcc ctctcctcca ggcccgtggg gctggccctg caccgccgag     540
cttcccggga tgagggcccc cggtgtggtc accggcgcc ccaggtcgct gagggacccc     600
ggccaggcgc ggagatgggg gtgcacggtg agtactcgcg ggctgggcgc tcccgcccgc     660
ccgggtccct gtttgagcgg ggatttagcg ccccggctat tggccaggag gtggctgggt     720
tcaaggaccg gcgacttgtc aaggaccccg gaaggggag ggggtgggg cagcctccac     780
gtgccagcgg ggacttgggg gagtccttgg ggatggcaaa aacctgacct gtgaagggga     840
cacagtttgg gggttgaggg gaagaaggtt tgggggtttc tgctgtgcca gtggagagga     900
agctgataag ctgataacct gggcgctgga gccaccactt atctgccaga ggggaagcct     960
ctgtcacacc aggattgaag tttggccgga gaagtggatg ctggtagcct gggggtgggg    1020
tgtgcacacg gcagcaggat tgaatgaagg ccagggaggc agcacctgag tgcttgcatg    1080
gttgggaca ggaaggacga gctggggcag agacgtgggg atgaaggaag ctgtccttcc    1140
acagccaccc ttctccctcc ccgcctgact ctcagcctgg ctatctgttc tagaatgtcc    1200
tgcctggctg tggcttctcc tgtccctgct gtcgctccct ctgggcctcc cagtcctggg    1260
cgccccacca cgcctcatct gtgacagccg agtcctgcag aggtacctct tggaggccaa    1320
ggaggccgag aatatcacgg tgagaccccct tccccagcac attccacaga actcacgctc    1380
agggcttcag ggaactcctc ccagatccag gaacctggca cttggttgg ggtggagttg    1440
ggaagctaga cactgccccc ctacataaga ataagtctgg tggccccaaa ccatacctgg    1500
aaactaggca aggagcaaag ccagcagatc ctacgcctgt ggccagggcc agagccttca    1560
gggacccttg actccccggg ctgtgtgcat ttcagacggg ctgtgctgaa cactgcagct    1620
tgaatgagaa tatcactgtc ccagacacca agttaatttt ctatgcctgg aagaggatgg    1680
aggtgagttc ctttttttt ttttttcctt tcttttggag aatctcattt gcgagcctga    1740
ttttggatga aagggagaat gatcgaggga aaggtaaaat ggagcagcag agatgaggct    1800
gcctgggcgc agaggctcac gtctataatc ccaggctgag atggccgaga tgggagaatt    1860
gcttgagccc tggagtttca gaccaaccta ggcagcatag tgagatcccc catctctaca    1920
aacatttaaa aaattagtc aggtgaagtg gtgcatggtg gtagtcccag atatttggaa    1980
ggctgaggcg ggaggatcgc ttgagcccag gaatttgagg ctgcagtgag ctgtgatcac    2040
accactgcac tccagcctca gtgacagagt gaggccctgt ctcaaaaaag aaaagaaaaa    2100
agaaaaataa tgagggctgt atggaatacg ttcattattc attcactcac tcactcactc    2160
attcattcat tcattcattc aacaagtctt attgcatacc ttctgtttgc tcagcttggt    2220
```

```
gcttggggct gctgaggggc aggagggaga gggtgacatc cctcagctga ctcccagagt    2280
ccactccctg taggtcgggc agcaggccgt agaagtctgg cagggcctgg ccctgctgtc    2340
ggaagctgtc ctgcggggcc aggccctgtt ggtcaactct tcccagccgt gggagcccct    2400
gcagctgcat gtggataaag ccgtcagtgg ccttcgcagc ctcaccactc tgcttcgggc    2460
tctgggagcc caggtgagta ggagcggaca cttctgcttg ccctttctgt aagaagggga    2520
gaagggtctt gctaaggagt acaggaactg tccgtattcc ttccctttct gtggcactgc    2580
agcgacctcc tgttttctcc ttggcagaag gaagccatct cccctccaga tgcggcctca    2640
gctgctccac tccgaacaat cactgctgac actttccgca aactcttccg agtctactcc    2700
aatttcctcc ggggaaagct gaagctgtac acaggggagg cctgcaggac aggggacaga    2760
tgaccaggtg tgtccacctg ggcatatcca ccacctccct caccaacatt gcttgtgcca    2820
caccctcccc cgccactcct gaaccccgtc gaggggctct cagctcagcg ccagcctgtc    2880
ccatggacac tccagtgcca ccaatgacat ctcaggggcc agaggaactg tccagagagc    2940
aactctgaga tctaaggatg tcacagggcc aacttgaggg cccagagcag gaagcattca    3000
gagagcagct ttaaactcag ggacagaccc atgctgggaa gacgcctgag ctcactcggc    3060
accctgcaaa attgatgcca ggacacgctt tggaggcgat ttacctgttt tcgcacctac    3120
catcagggac aggatgacct ggagaactta ggtggcaagc tgtgacttct ccaggtctca    3180
cgggcatggg cactcccttg gtggcaagag cccccttgac accggggtgg tgggaaccat    3240
gaagacagga tgggggctgg cctctggctc tcatggggtc caacttttgt gtattcttca    3300
acctcattga caagaactga aaccaccaat atgactcttg gcttttctgt tttctgggaa    3360
cctccaaatc ccctggctct gtcccactcc tggcagca                           3398
```